US008158364B2

(12) United States Patent  (10) Patent No.: US 8,158,364 B2
Sarkar et al.  (45) Date of Patent: Apr. 17, 2012

(54) METHODS AND COMPOSITIONS INVOLVING NUCLEOTIDE REPEAT DISORDERS

(75) Inventors: Partha Sarkar, League City, TX (US); Tetsuo Ashizwa, Gainesville, FL (US); Weidong Xu, San Diego, CA (US)

(73) Assignee: The Board of Regents of The University of Texas System, Austin, TX (US)

( * ) Notice: Subject to any disclaimer, the term of this patent is extended or adjusted under 35 U.S.C. 154(b) by 150 days.

(21) Appl. No.: 12/296,846

(22) PCT Filed: Apr. 11, 2007

(86) PCT No.: PCT/US2007/066470
§ 371 (c)(1),
(2), (4) Date: May 7, 2010

(87) PCT Pub. No.: WO2007/121272
PCT Pub. Date: Oct. 25, 2007

(65) Prior Publication Data
US 2011/0033480 A1  Feb. 10, 2011

Related U.S. Application Data

(60) Provisional application No. 60/791,071, filed on Apr. 11, 2006.

(51) Int. Cl.
*G01N 33/53* (2006.01)
*C12Q 1/68* (2006.01)
*C12Q 1/00* (2006.01)

(52) U.S. Cl. .............................. 435/7.1; 435/4; 435/6.1

(58) Field of Classification Search .......................... None
See application file for complete search history.

(56) References Cited

U.S. PATENT DOCUMENTS

| | | | |
|---|---|---|---|
| 7,015,012 B2 | 3/2006 | Housman et al. | 435/29 |
| 2007/0054259 A1* | 3/2007 | Kim et al. | 435/4 |

OTHER PUBLICATIONS

Wu et al., SEL-10 Is an Inhibitor of Notch Signaling That Targets Notch for Ubiquitin-Mediated Protein Degradation, Nov. 2001, Molecular and Cellular Biology, vol. 21, No. 21, p. 7403-7415.*
Luo et al, Isolation and Functional Analysis of a cDNA for Human Jagged2, a Gene Encoding a Ligand for the Notch1 Receptor, Oct. 1997, Molecular and Cellular Biology,vol. 17, No. 10, p. 6057-6067.*
Takeuchi et al., Skeletrophin, a Novel RING Molecule Controlled by the Chromatin Remodeling Complex, Is Downregulated in Malignant Melanoma, DNA and Cell Biology, vol. 24, No. 5, 2005, pp. 339-344.*
Haltiwanger et al., Modulation of receptor signaling by glycosylation: fringe is an O-fucose-h1,3-N-acetylglucosaminyltransferase, Biochimica et Biophysica Acta 1573 (2002) 328-335.*
Furling et al., Viral vector producing antisense RNA restores myotonic dystrophy myoblast functions, Gene Therapy (2003) 10, 795-802.*
Artavanis-Tsakonas, "Notch Signaling: Cell Fate Control and Signal Integration in Development" Science, Apr. 30, 1999, vol. 284, pp. 770-776.*
Alves-Rodrigues et al., "Ubiquitin, cellular inclusions and their role in neurodegeneration" Trends Neurosci. (1998) 21, 516-520.*
Timchenko et al. "Novel proteins with binding specificity for DNA CTG repeats and RNA CUG repeats: implications for myotonic dystrophy" Human Molecular Genetics, 1996, vol. 5, No. 1 115-121.*
Ono et al., "Immunohistochemical study of intracytoplasmic inclusion bodies of the thalamus in myotonic dystrophy," Journal of the Neurological Sciences 140 ( 1996) 96-100.*
Miller et al., "Recruitment of human muscleblind proteins to (CUG)n expressions associated with myotnic dystrophy," The EMBO Journal, vol. 19 No. 17 pp. 4439-4448, 2000.*
Laroia et al., "Ubiquitin-dependent mechanism regulates rapid turnover of AU-rich cytokine mRNAs," PNAS, vol. 99, No. 4, pp. 1842-1846, 2002.*
Ranum et al., "Myotonic Dystrophy: RNA Pathogenesis Comes into Focus," Am. J. Hum. Genet. 74:793-804, 2004.*
Gatchel et al., "Diseases of unstable repeat expansion: Mechanisms and common principles," Nature Reviews, vol. 6, pp. 743-755, 2005.*
Udd et al., "140th ENMC International Workshop: Myotonic Dystrophy DM2/PROMM and other mytonic dystrophies with guidelines on management" Neuromuscular Disorders 16 (2006) 403-413.*
Haro et al., "MBNL1 and CUGBP1 modify expanded CUG-induced toxicity in a *Drosophila* model of myotonic dystrophy type 1," Human Molecular Genetics, 2006, vol. 15, No. 13 2138-2145.*
Ranum et al., "RNA-Mediated Neuromuscular Disorders," Annu. Rev. Neurosci. 2006.29:259-277.*
Takeuchi et al., "A ubiquitin ligase, skeletrophin, is a negative regulator of melanoma invasion," Oncogene (2006) 25, 7059-7069.*
Robinson et al., "Ubuiquitin-protein ligase," Journal of Cell Science 117, 2004, 51191-5194.*
Everett et al.,"Trinucleotide repeats and neurodegenerative disease" Brain (2004), 127, 2385-2405.*
Sandri et al., "Foxo transcription factors induce the atrophy-related ubiquitin ligase atrogin-1 and cause skeletal muscle atrophy," Cell 2004; 117:399-412.*
Mammucari et al., "FoxO3 controls autophagy in skeletal muscle in vivo," Cell Metab 2007; 6:458-71.*
Orengo et al., "Expanded CTG repeats within the DMPK 30 UTR causes severe skeletal muscle wasting in an inducible mouse model for myotonic dystrophy," Proc Natl Acad Sci USA 2008;105:2646-51.*
Bodine et al., "Identification of ubiquitin ligases required for skeletal muscle atrophy" Science 2001;294:1704-8.*
Antonarakis and Cooper, "Mutations in human genetic disease," Encyclopedia of the Human Genome, Macmillian Publishers Ltd., Nature Publishing Group, 1-34, 2003.

(Continued)

*Primary Examiner* — Jennifer Dunston
*Assistant Examiner* — Reza Ghafoorian

(57) ABSTRACT

The present invention concerns the methods and compositions involving nucleic acids with long repeat sequences. In some embodiments of the invention, there are methods for generating such a nucleic acid, and in other methods, there are methods for using such a nucleic acid to screen for candidate therapeutic compounds. Furthermore the present invention relates to methods of screening for Notch inhibitors and other substances that may be used to treat muscle loss and wasting.

5 Claims, 7 Drawing Sheets

OTHER PUBLICATIONS

Bates, "The molecular genetics of Huntington disease—a history," *Nature Review Genetics*, 6:766-773, 2005.

Brooks and Fischbeck, "Spinal and bulbar muscular atrophy: a trinucleotide-repeat expansion neurodegenerative disease," *TINS*, 18:459-461, 1995.

Day and Ranum, "RNA pathogenesis of the myotonic dystrophies," *Neuromuscul. Disord.*, 15:5-16, 2005.

Gatchel and Zoghbi, "Disease of unstable repeat expansion: mechanisms and common principles," *Nature Reviews Genetics*, 6:743-755, 2005.

Hashem et al., "Genetic assays for measuring rates of (CAG).(CTG) repeat instability in *Escherichia coli*," *Mutat. Res.*, 502:25-37, 2002.

Hashem et al., "Instability of repeated DNAs during transformation in *Escherichia coli*," *Mutat. Res.*, 502:39-46, 2002.

Hsieh et al., "Truncated mammalian Notch1 activates CBF1/RBPJk-repressed genes by a mechanism resembling that of Epstein-Barr virus EBNA2," *Mol. Cell. Biol.*, 16:952-959, 1996.

Jiang et al., "Myotonic dystrophy type 1 is associated with nuclear foci of mutant RNA, sequestration of muscleblind proteins and deregulated alternative splicing in neurons," *Hum. Mol. Genet.*, 13:3079-3088, 2004.

Kanadia et al., "A muscleblind knockout model for myotonic dystrophy," *Science*, 302:1978-1980, 2003.

Kremer et al., "Mapping of DNA instability at the fragile X to a trinucleotide repeat sequence p(CCG)$_n$," *Science*, 252:1711-1714, 1991.

La Spada et al., "Androgen receptor gene mutations in X-linked spinal and bulbar muscular atrophy," *Nature*, 352:77-79, 1991.

Lalioti et al., "Dodecamer repeat expansion in cystatin B gene in progressive myoclonus epilepsy," *Nature*, 386:847-851, 1997.

Liguori et al., "Myotonic dystrophy type 2 caused by a CCTG expansion in intron 1 of *ZNF9*," *Science*, 293, 864-867, 2001.

Mankodi et al., "Expanded CUG repeats trigger aberrant splicing of ClC-1 chloride channel pre-mRNA and hyperexcitability of skeletal muscle in myotonic dystrophy," *Mol. Cell.*, 10:35-44, 2002.

Mankodi et al., "Myotonic dystrophy in transgenic mice expressing an expanded CUG repeat," *Science*, 289:1769-1773, 2000.

Mankodi et al., "Ribonuclear inclusions in skeletal muscle in myotonic dystrophy types 1 and 2," *Ann. Neurol.*, 54:760-768, 2003.

Margolis et al., "Trinucleotide repeat expansion and neuropsychiatric disease," *Arch. Gen. Psychiatry*, 56:1019-1031, 1999.

Matsuura et al., "Large expansion of the ATTCT pentanucleotide repeat in spinocerebellar ataxia type 10," *Nature Genetics*, 26:191-194, 2000.

Miller et al., "Recruitment of human muscleblind proteins to (CUG)$_n$ expansions associated with myotonic dystrophy," *EMBO J.*, 19:4439-4448, 2000.

Mitas, "Trinucleotide repeats associated with human disease," *Nucleic Acids Research*, 25:2245-2253, 1997.

Oberlé et al., "Instability of a 500-base pair DNA segment and abnormal methylation in fragile X syndrome," *Science*, 252:1097-1102, 1991.

Ranum and Day, "Myotonic dystrophy: clinical and molecular parallels between myotonic dystrophy type 1 and type 2," *Curr. Neurol. Neurosci. Rep.*, 2:465-470, 2002.

Ranum and Day, "Pathogenic RNA repeats: an expanding role in genetic disease," *TRENDS in Genetics*, 20:506-512, 2004.

Richards and Sutherland, "Dynamic mutation: possible mechanisms and significance in human disease," *TIBS*, 22:432-436, 1997.

Richards, "Dynamic mutations: a decade of unstable expanded repeats in human genetic disease," *Human Molecular Genetics*, 10:2187-2194, 2001.

Sarkar et al., "CTG repeats show bimodal amplification in *E. coli*," *Cell*, 95:531-540, 1998.

Shearman et al., "L-685,458, an aspartyl protease transition state mimic, is a potent inhibitor of amyloid beta-protein precursor gamma-secretase activity," *Biochemistry*, 39:8698-8704, 2000.

Sobczak et al., "RNA structure of trinucleotide repeats associated with human neurological diseases," *Nucleic Acids Research*, 31:5469-5482, 2003.

Tang et al., "High-level and erythroid-specific expression of human glucose-6-phosphate dehydrogenase in transgenic mice," *J. Biol. Chem.*, 268:9522-9525, 1993.

Yu et al., "Human chromosomal fragile site *FRA16B* is an amplified AT-rich minisatellite repeat," *Cell*, 88:367-374, 1997.

\* cited by examiner

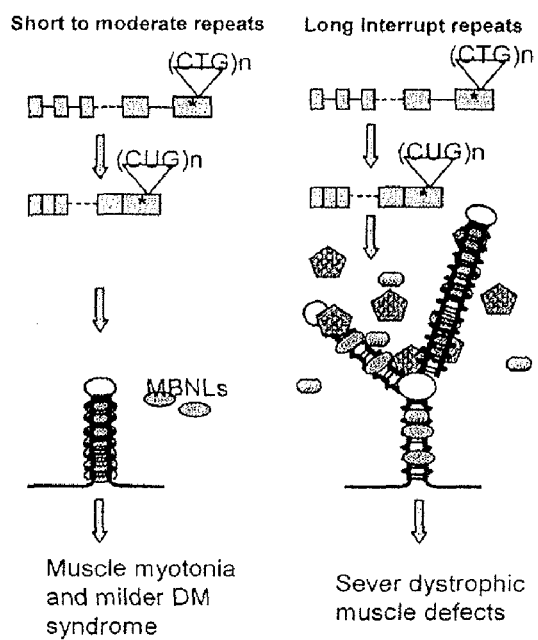
FIG. 1.
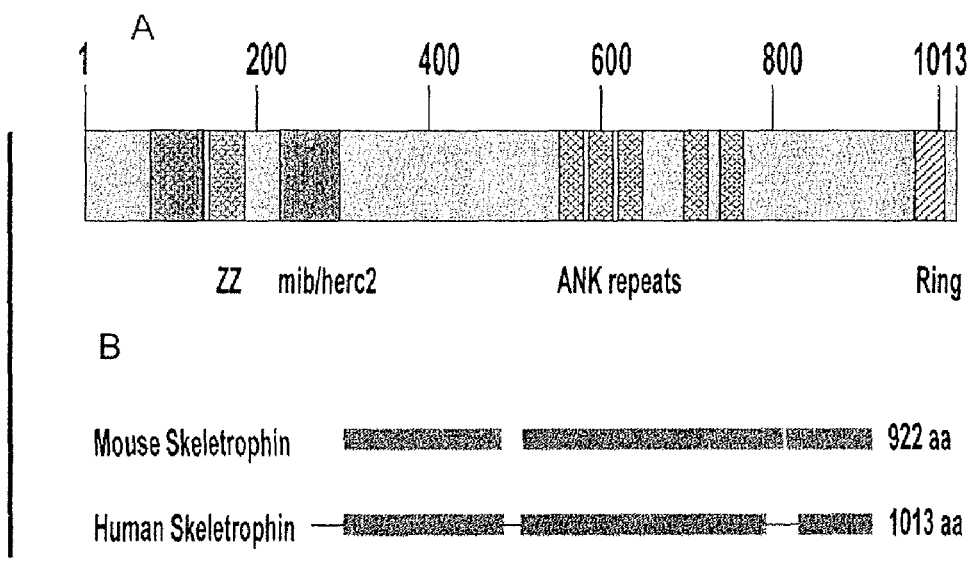
FIG. 2A–B

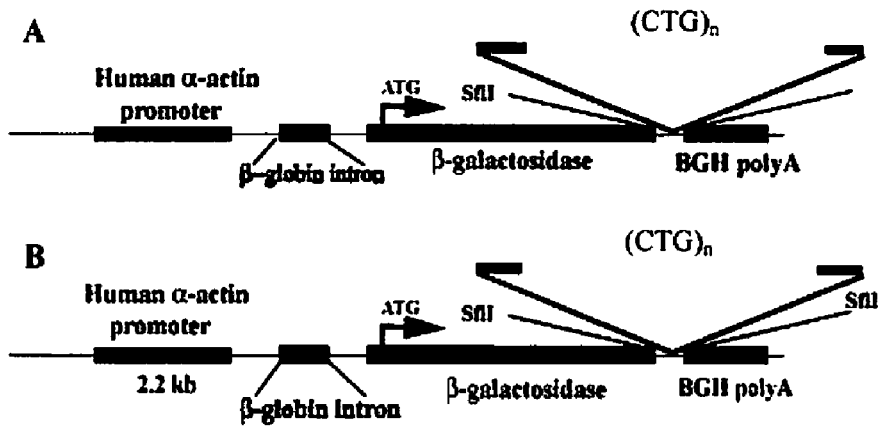
FIGs. 3A-B.
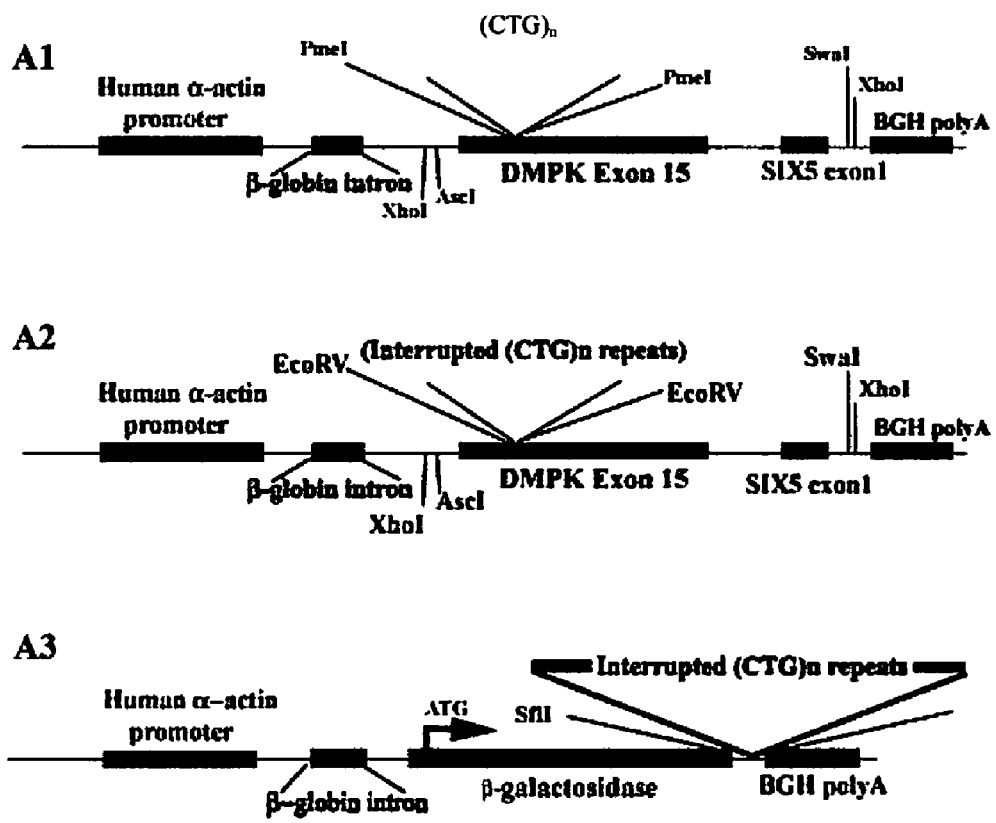
FIGs. 4A1-4A3.

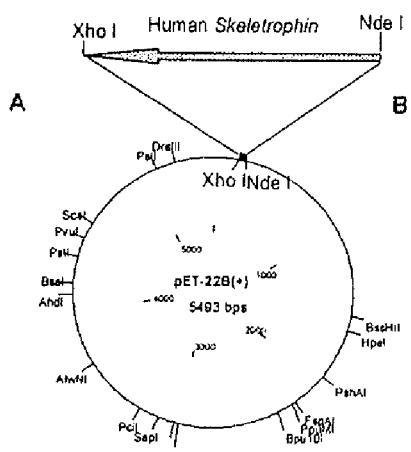
FIG. 5.
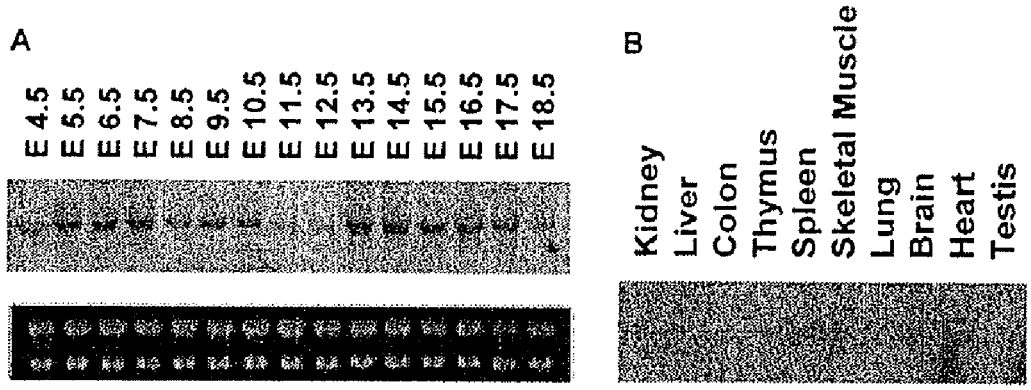
FIG. 6A-B.

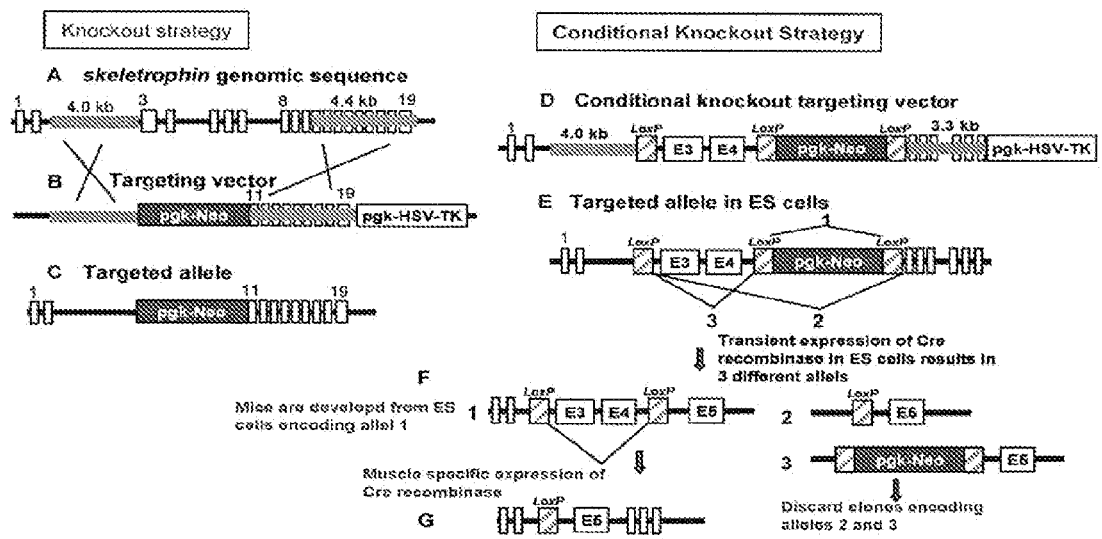
FIGs. 7A-G
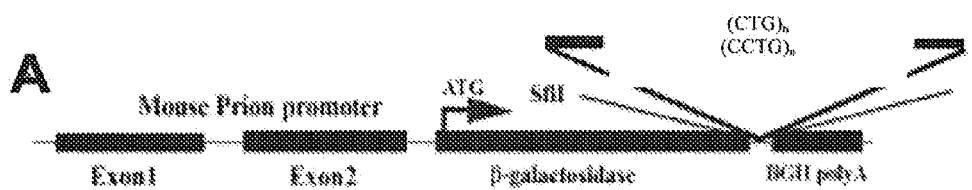
FIG. 8
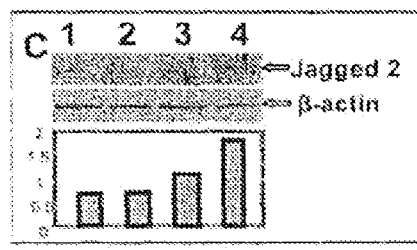
FIG. 9.

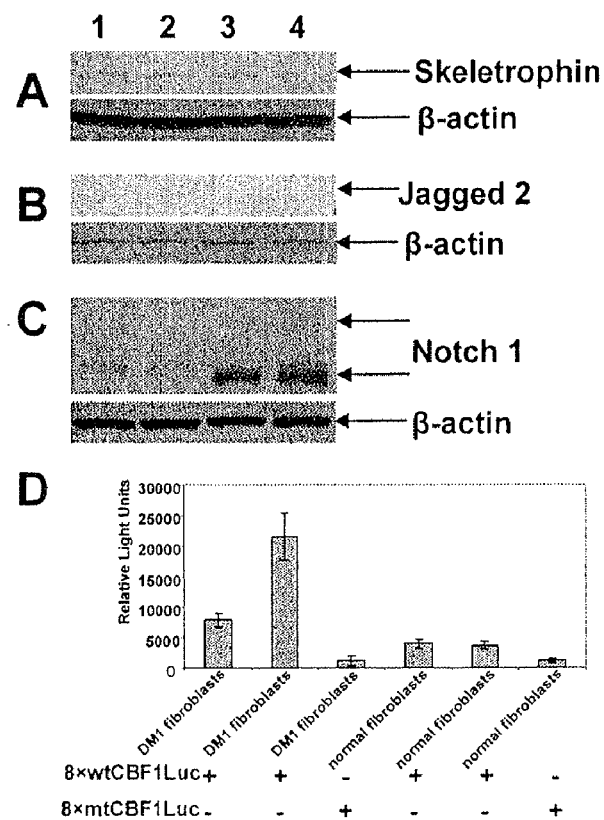
FIG. 10A-D
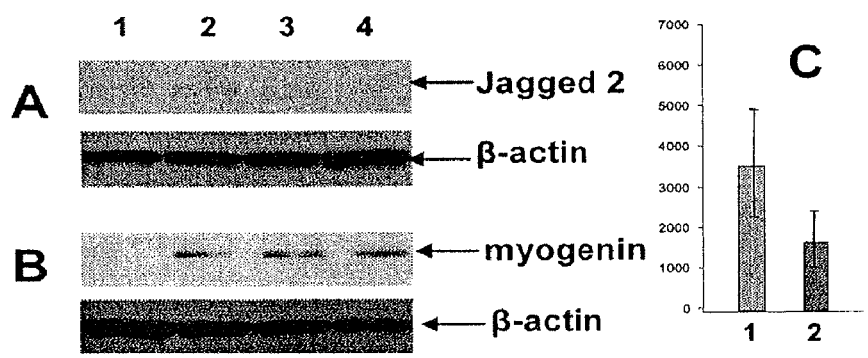
FIG. 11A-C

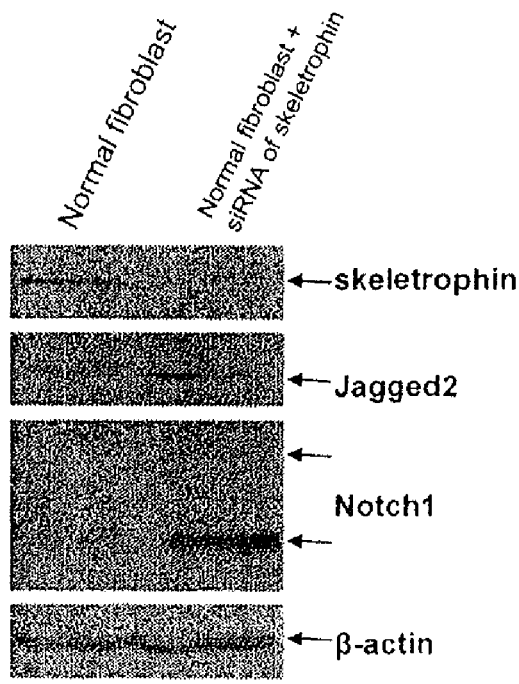
FIG. 12
1. Targeting vector for the development of *Skeletrophin* knockout mice
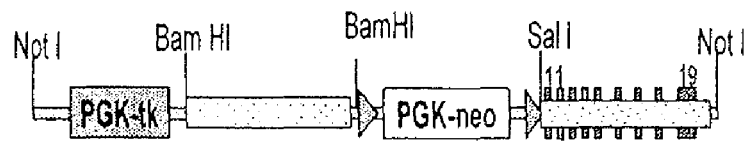
2. Targeting vector for the development of *Skeletrophin* conditional knockout mice
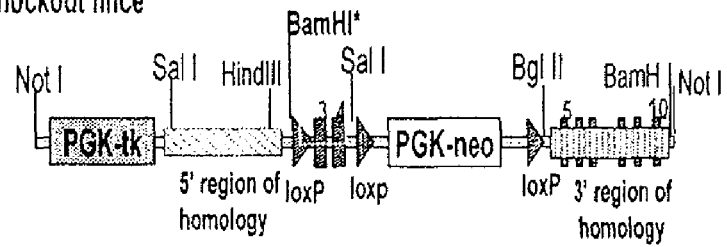
FIG. 13

SEQUENCE LISTING

```
<160> NUMBER OF SEQ ID NOS: 6

<210> SEQ ID NO 1
<211> LENGTH: 2726
<212> TYPE: DNA
<213> ORGANISM: Homo sapiens
<220> FEATURE:
<221> NAME/KEY: CDS
<222> LOCATION: (128)..(2002)

<400> SEQUENCE: 1
ggggacagcc agggacaggc agacatgcag ccagggctcc agggcctgga cagggctgc       60 caggccctgt gacaggagga ccccgagccc ccggcccggg gaggggccat ggtgctgcct      120 gtccaac atg tca gcc gag gtg cgg ctg agg cgg ctc cag cag ctg gtg       169
        Met Ser Ala Glu Val Arg Leu Arg Arg Leu Gln Gln Leu Val
        1               5                   10 ttg gac ccg ggc ttc ctg ggg ctg gag ccc ctc gac ctt ctc ctg           217
Leu Asp Pro Gly Phe Leu Gly Leu Glu Pro Leu Leu Asp Leu Leu Leu
15                  20                  25                  30 ggc gtc cac cag gag ctg ggc gcc tcc gaa ctg gcc cag gac aag tac       265
Gly Val His Gln Glu Leu Gly Ala Ser Glu Leu Ala Gln Asp Lys Tyr
                35                  40                  45 gtg gcc gac ttc ttg cag tgg gcg gag ccc atc gtg gtg agg ctt aag       313
Val Ala Asp Phe Leu Gln Trp Ala Glu Pro Ile Val Val Arg Leu Lys
            50                  55                  60
```

-continued

```
gag gtc cga ctg cag agg gac gac ttc gag att ctg aag gtg atc gga      361
Glu Val Arg Leu Gln Arg Asp Asp Phe Glu Ile Leu Lys Val Ile Gly
         65                  70                  75 cgc ggg gcg ttc agc gag gta gcg gta gtg aag atg aag cag acg ggc      409
Arg Gly Ala Phe Ser Glu Val Ala Val Val Lys Met Lys Gln Thr Gly
 80                  85                  90 cag gtg tat gcc atg aag atc atg aac aag tgg gac atg ctg aag agg      457
Gln Val Tyr Ala Met Lys Ile Met Asn Lys Trp Asp Met Leu Lys Arg
 95                 100                 105                 110 ggc gag gtg tcg tgc ttc cgt gag gag agg gac gtg ttg gtg aat ggg      505
Gly Glu Val Ser Cys Phe Arg Glu Glu Arg Asp Val Leu Val Asn Gly
                115                 120                 125 gac cgg cgg tgg atc acg cag ctg cac ttc gcc ttc cag gat gag aac      553
Asp Arg Arg Trp Ile Thr Gln Leu His Phe Ala Phe Gln Asp Glu Asn
            130                 135                 140 tac ctg tac ctg gtc atg gag tat tac gtg ggc ggg gac ctg ctg aca      601
Tyr Leu Tyr Leu Val Met Glu Tyr Tyr Val Gly Gly Asp Leu Leu Thr
        145                 150                 155 ctg ctg agc aag ttt ggg gag cgg att ccg gcc gag atg gcg cgc ttc      649
Leu Leu Ser Lys Phe Gly Glu Arg Ile Pro Ala Glu Met Ala Arg Phe
    160                 165                 170 tac ctg gcg gag att gtc atg gcc ata gac tcg gtg cac cgg ctt ggc      697
Tyr Leu Ala Glu Ile Val Met Ala Ile Asp Ser Val His Arg Leu Gly
175                 180                 185                 190 tac gtg cac agg gac atc aaa ccc gac aac atc ctg ctg gac cgc tgt      745
Tyr Val His Arg Asp Ile Lys Pro Asp Asn Ile Leu Leu Asp Arg Cys
                195                 200                 205 ggc cac atc cgc ctg gcc gac ttc ggc tct tgc ctc aag ctg cgg gca      793
Gly His Ile Arg Leu Ala Asp Phe Gly Ser Cys Leu Lys Leu Arg Ala
            210                 215                 220 gat gga acg gtg cgg tcg ctg gtg gct gtg ggc acc cca gac tac ctg      841
Asp Gly Thr Val Arg Ser Leu Val Ala Val Gly Thr Pro Asp Tyr Leu
        225                 230                 235 tcc ccc gag atc ctg cag gct gtg ggc ggt ggg cct ggg aca ggc agc      889
Ser Pro Glu Ile Leu Gln Ala Val Gly Gly Gly Pro Gly Thr Gly Ser
    240                 245                 250 tac ggg ccc gag tgt gac tgg tgg gcg ctg ggt gta ttc gcc tat gaa      937
Tyr Gly Pro Glu Cys Asp Trp Trp Ala Leu Gly Val Phe Ala Tyr Glu
255                 260                 265                 270 atg ttc tat ggg cag acg ccc ttc tac gcg gat tcc acg gcg gag acc      985
Met Phe Tyr Gly Gln Thr Pro Phe Tyr Ala Asp Ser Thr Ala Glu Thr
                275                 280                 285 tat ggc aag atc gtc cac tac aag gag cac ctc tct ctg ccg ctg gtg     1033
Tyr Gly Lys Ile Val His Tyr Lys Glu His Leu Ser Leu Pro Leu Val
            290                 295                 300 gac gaa ggg gtc cct gag gag gct cga gac ttc att cag cgg ttg ctg     1081
Asp Glu Gly Val Pro Glu Glu Ala Arg Asp Phe Ile Gln Arg Leu Leu
        305                 310                 315 tgt ccc ccg gag aca cgg ctg ggc cgg ggt gga gca ggc gac ttc cgg     1129
Cys Pro Pro Glu Thr Arg Leu Gly Arg Gly Gly Ala Gly Asp Phe Arg
    320                 325                 330 aca cat ccc ttc ttc ttt ggc ctc gac tgg gat ggt ctc cgg gac agc     1177
Thr His Pro Phe Phe Phe Gly Leu Asp Trp Asp Gly Leu Arg Asp Ser
335                 340                 345                 350 gtg ccc ccc ttt aca ccg gat ttc gaa ggt gcc acc gac aca tgc aac     1225
Val Pro Pro Phe Thr Pro Asp Phe Glu Gly Ala Thr Asp Thr Cys Asn
                355                 360                 365 ttc gac ttg gtg gag gac ggg ctc act gcc atg gag aca ctg tcg gac     1273
Phe Asp Leu Val Glu Asp Gly Leu Thr Ala Met Glu Thr Leu Ser Asp
            370                 375                 380
```

-continued

| | | | | | | | | | | | | | | | | |
|---|---|---|---|---|---|---|---|---|---|---|---|---|---|---|---|---|
| att | cgg | gaa | ggt | gcg | ccg | cta | ggg | gtc | cac | ctg | cct | ttt | gtg | ggc | tac | 1321 |
| Ile | Arg | Glu | Gly | Ala | Pro | Leu | Gly | Val | His | Leu | Pro | Phe | Val | Gly | Tyr | |
| | | 385 | | | | 390 | | | | 395 | | | | | | |
| tcc | tac | tcc | tgc | atg | gcc | ctc | agg | gac | agt | gag | gtc | cca | ggc | ccc | aca | 1369 |
| Ser | Tyr | Ser | Cys | Met | Ala | Leu | Arg | Asp | Ser | Glu | Val | Pro | Gly | Pro | Thr | |
| | 400 | | | | 405 | | | | | 410 | | | | | | |
| ccc | atg | gaa | gtg | gag | gcc | gag | cag | ctg | ctt | gag | cca | cac | gtg | caa | gcg | 1417 |
| Pro | Met | Glu | Val | Glu | Ala | Glu | Gln | Leu | Leu | Glu | Pro | His | Val | Gln | Ala | |
| 415 | | | | 420 | | | | | 425 | | | | | 430 | | |
| ccc | agc | ctg | gag | ccc | tcg | gtg | tcc | cca | cag | gat | gaa | aca | gct | gaa | gtg | 1465 |
| Pro | Ser | Leu | Glu | Pro | Ser | Val | Ser | Pro | Gln | Asp | Glu | Thr | Ala | Glu | Val | |
| | | | 435 | | | | 440 | | | | | 445 | | | | |
| gca | gtt | cca | gcg | gct | gtc | cct | gca | gca | gag | gct | gag | gcc | gag | gtg | acg | 1513 |
| Ala | Val | Pro | Ala | Ala | Val | Pro | Ala | Ala | Glu | Ala | Glu | Ala | Glu | Val | Thr | |
| | | 450 | | | | 455 | | | | 460 | | | | | | |
| ctg | cgg | gag | ctc | cag | gaa | gcc | ctg | gag | gag | gag | gtg | ctc | acc | cgg | cag | 1561 |
| Leu | Arg | Glu | Leu | Gln | Glu | Ala | Leu | Glu | Glu | Glu | Val | Leu | Thr | Arg | Gln | |
| | 465 | | | | 470 | | | | 475 | | | | | | | |
| agc | ctg | agc | cgg | gag | atg | gag | gcc | atc | cgc | acg | gac | aac | cag | aac | ttc | 1609 |
| Ser | Leu | Ser | Arg | Glu | Met | Glu | Ala | Ile | Arg | Thr | Asp | Asn | Gln | Asn | Phe | |
| 480 | | | | 485 | | | | | 490 | | | | | | | |
| gcc | agt | caa | cta | cgc | gag | gca | gag | gct | cgg | aac | cgg | gac | cta | gag | gca | 1657 |
| Ala | Ser | Gln | Leu | Arg | Glu | Ala | Glu | Ala | Arg | Asn | Arg | Asp | Leu | Glu | Ala | |
| 495 | | | | 500 | | | | | 505 | | | | | 510 | | |
| cac | gtc | cgg | cag | ttg | cag | gag | cgg | atg | gag | ttg | ctg | cag | gca | gag | gga | 1705 |
| His | Val | Arg | Gln | Leu | Gln | Glu | Arg | Met | Glu | Leu | Leu | Gln | Ala | Glu | Gly | |
| | | | 515 | | | | 520 | | | | | 525 | | | | |
| gcc | aca | gct | gtc | acg | ggg | gtc | ccc | agt | ccc | cgg | gcc | acg | gat | cca | cct | 1753 |
| Ala | Thr | Ala | Val | Thr | Gly | Val | Pro | Ser | Pro | Arg | Ala | Thr | Asp | Pro | Pro | |
| | | 530 | | | | 535 | | | | | 540 | | | | | |
| tcc | cat | cta | gat | ggc | ccc | cgg | gcc | gtg | gct | gtg | ggc | cag | tgc | ccg | ctg | 1801 |
| Ser | His | Leu | Asp | Gly | Pro | Pro | Ala | Val | Ala | Val | Gly | Gln | Cys | Pro | Leu | |
| | 545 | | | | 550 | | | | | 555 | | | | | | |
| gtg | ggg | cca | ggc | ccc | atg | cac | cgc | cgc | cac | ctg | ctc | ctc | cct | gcc | agg | 1849 |
| Val | Gly | Pro | Gly | Pro | Met | His | Arg | Arg | His | Leu | Leu | Leu | Pro | Ala | Arg | |
| 560 | | | | | 565 | | | | | 570 | | | | | | |
| gtc | cct | agg | cct | ggc | cta | tcg | gag | gcg | ctt | tcc | ctg | ctc | ctg | ttc | gcc | 1897 |
| Val | Pro | Arg | Pro | Gly | Leu | Ser | Glu | Ala | Leu | Ser | Leu | Leu | Leu | Phe | Ala | |
| 575 | | | | | 580 | | | | | 585 | | | | | 590 | |
| gtt | gtt | ctg | tct | cgt | gcc | gcc | gcc | ctg | ggc | tgc | att | ggg | ttg | gtg | gcc | 1945 |
| Val | Val | Leu | Ser | Arg | Ala | Ala | Ala | Leu | Gly | Cys | Ile | Gly | Leu | Val | Ala | |
| | | | | 595 | | | | 600 | | | | | 605 | | | |
| cac | gcc | ggc | caa | ctc | acc | gca | gtc | tgg | cgc | cgc | cca | gga | gcc | gcc | cgc | 1993 |
| His | Ala | Gly | Gln | Leu | Thr | Ala | Val | Trp | Arg | Arg | Pro | Gly | Ala | Ala | Arg | |
| | | | 610 | | | | | 615 | | | | 620 | | | | |
| gct | ccc | tga | acctagaac | tgtcttcgac | tccggggccc | cgttggaaga | | | | | | | | | | 2042 |
| Ala | Pro | | | | | | | | | | | | | | | | ctgagtgccc gggccagca cagaagccgc gcccaccgcc tgccagttca caaccgctcc 2102 gagcgtgggt ctccgcccag ctccagtcct gtgatccggg cccgcccct agcggccggg 2162 gagggagggg ccgggtccgc ggccggcgaa cggggctcga aggtccttg tagccgggaa 2222 tgctgctgct gctgctgctg ctgctgctgc tgctgggggg atcacagacc atttctttct 2282 ttcggccagg ctgaggccct gacgtggatg ggcaaactgc aggcctggga aggcagcaag 2342 ccgggccgtc cgtgttccat cctccacgca cccccaccta tcgttggttc gcaaagtgca 2402 aagctttctt gtgcatgacg ccctgctctg gggagcgtct ggcgcgatct ctgcctgctt 2462 actcgggaaa tttgcttttg ccaaaccccgc ttttttcgggg atcccgcgcc ccctcctca 2522 cttgcgctgc tctcggagcc ccagccggct ccgccgcctt cggcggtttg gatatttatt 2582

```
gacctcgtcc tccgactcgc tgacaggcta caggaccccc aacaacccca atccacgttt    2642
tggatgcact gagaccccga cattcctcgg tatttattgt ctgtcccccac ctaggacccc    2702 caccccgac cctcgcgaat aaaa    2726
```

<210> SEQ ID NO 2
<211> LENGTH: 624
<212> TYPE: PRT
<213> ORGANISM: Homo sapiens

<400> SEQUENCE: 2

```
Met Ser Ala Glu Val Arg Leu Arg Arg Leu Gln Gln Leu Val Leu Asp
 1               5                  10                  15

Pro Gly Phe Leu Gly Leu Glu Pro Leu Leu Asp Leu Leu Leu Gly Val
                20                  25                  30

His Gln Glu Leu Gly Ala Ser Glu Leu Ala Gln Asp Lys Tyr Val Ala
            35                  40                  45

Asp Phe Leu Gln Trp Ala Glu Pro Ile Val Val Arg Leu Lys Glu Val
        50                  55                  60

Arg Leu Gln Arg Asp Asp Phe Glu Ile Leu Lys Val Ile Gly Arg Gly
    65                  70                  75                  80

Ala Phe Ser Glu Val Ala Val Val Lys Met Lys Gln Thr Gly Gln Val
                85                  90                  95

Tyr Ala Met Lys Ile Met Asn Lys Trp Asp Met Leu Lys Arg Gly Glu
            100                 105                 110

Val Ser Cys Phe Arg Glu Glu Arg Asp Val Leu Val Asn Gly Asp Arg
        115                 120                 125

Arg Trp Ile Thr Gln Leu His Phe Ala Phe Gln Asp Glu Asn Tyr Leu
    130                 135                 140

Tyr Leu Val Met Glu Tyr Tyr Val Gly Gly Asp Leu Leu Thr Leu Leu
145                 150                 155                 160

Ser Lys Phe Gly Glu Arg Ile Pro Ala Glu Met Ala Arg Phe Tyr Leu
                165                 170                 175

Ala Glu Ile Val Met Ala Ile Asp Ser Val His Arg Leu Gly Tyr Val
            180                 185                 190

His Arg Asp Ile Lys Pro Asp Asn Ile Leu Leu Asp Arg Cys Gly His
        195                 200                 205

Ile Arg Leu Ala Asp Phe Gly Ser Cys Leu Lys Leu Arg Ala Asp Gly
    210                 215                 220

Thr Val Arg Ser Leu Val Ala Val Gly Thr Pro Asp Tyr Leu Ser Pro
225                 230                 235                 240

Glu Ile Leu Gln Ala Val Gly Gly Gly Pro Gly Thr Gly Ser Tyr Gly
                245                 250                 255

Pro Glu Cys Asp Trp Trp Ala Leu Gly Val Phe Ala Tyr Glu Met Phe
            260                 265                 270

Tyr Gly Gln Thr Pro Phe Tyr Ala Asp Ser Thr Ala Glu Thr Tyr Gly
        275                 280                 285

Lys Ile Val His Tyr Lys Glu His Leu Ser Leu Pro Leu Val Asp Glu
    290                 295                 300

Gly Val Pro Glu Glu Ala Arg Asp Phe Ile Gln Arg Leu Leu Cys Pro
305                 310                 315                 320

Pro Glu Thr Arg Leu Gly Arg Gly Gly Ala Gly Asp Phe Arg Thr His
                325                 330                 335

Pro Phe Phe Phe Gly Leu Asp Trp Asp Gly Leu Arg Asp Ser Val Pro
            340                 345                 350
```

```
Pro Phe Thr Pro Asp Phe Glu Gly Ala Thr Asp Thr Cys Asn Phe Asp
        355                 360                 365

Leu Val Glu Asp Gly Leu Thr Ala Met Glu Thr Leu Ser Asp Ile Arg
    370                 375                 380

Glu Gly Ala Pro Leu Gly Val His Leu Pro Phe Val Gly Tyr Ser Tyr
385                 390                 395                 400

Ser Cys Met Ala Leu Arg Asp Ser Glu Val Pro Gly Pro Thr Pro Met
                405                 410                 415

Glu Val Glu Ala Glu Gln Leu Leu Glu Pro His Val Gln Ala Pro Ser
                420                 425                 430

Leu Glu Pro Ser Val Ser Pro Gln Asp Glu Thr Ala Glu Val Ala Val
            435                 440                 445

Pro Ala Ala Val Pro Ala Ala Glu Ala Glu Ala Glu Val Thr Leu Arg
        450                 455                 460

Glu Leu Gln Glu Ala Leu Glu Glu Val Leu Thr Arg Gln Ser Leu
465                 470                 475                 480

Ser Arg Glu Met Glu Ala Ile Arg Thr Asp Asn Gln Asn Phe Ala Ser
                485                 490                 495

Gln Leu Arg Glu Ala Glu Ala Arg Asn Arg Asp Leu Glu Ala His Val
            500                 505                 510

Arg Gln Leu Gln Glu Arg Met Glu Leu Leu Gln Ala Glu Gly Ala Thr
        515                 520                 525

Ala Val Thr Gly Val Pro Ser Pro Arg Ala Thr Asp Pro Pro Ser His
        530                 535                 540

Leu Asp Gly Pro Pro Ala Val Ala Val Gly Gln Cys Pro Leu Val Gly
545                 550                 555                 560

Pro Gly Pro Met His Arg His Leu Leu Leu Pro Ala Arg Val Pro
                565                 570                 575

Arg Pro Gly Leu Ser Glu Ala Leu Ser Leu Leu Leu Phe Ala Val Val
            580                 585                 590

Leu Ser Arg Ala Ala Ala Leu Gly Cys Ile Gly Leu Val Ala His Ala
        595                 600                 605

Gly Gln Leu Thr Ala Val Trp Arg Arg Pro Gly Ala Ala Arg Ala Pro
        610                 615                 620

<210> SEQ ID NO 3
<211> LENGTH: 2562
<212> TYPE: DNA
<213> ORGANISM: Homo sapiens
<220> FEATURE:
<221> NAME/KEY: CDS
<222> LOCATION: (29)..(2488)

<400> SEQUENCE: 3
ctgctgcaag aagcacgggc tgcgggggg atg cgc tgg aag tgc cgt gtg tgc        52
                                 Met Arg Trp Lys Cys Arg Val Cys
                                  1               5 ctg gac tac gac ctc tgc acg cag tgc tac atg cac aac aag cat gag       100
Leu Asp Tyr Asp Leu Cys Thr Gln Cys Tyr Met His Asn Lys His Glu
     10                  15                  20 ctc gcc cac gcc ttc gac cgc tac gag acc gct cac tcg cgc cct gtc       148
Leu Ala His Ala Phe Asp Arg Tyr Glu Thr Ala His Ser Arg Pro Val
 25                  30                  35                  40 aca ctg agt ccc cgc cag ggc ctc ccg agg atc cca cta agg ggc atc       196
Thr Leu Ser Pro Arg Gln Gly Leu Pro Arg Ile Pro Leu Arg Gly Ile
                 45                  50                  55 ttc cag gga gcg aag gtg gtg cga ggc ccc gac tgg gag tgg ggc tca       244
```

```
                                                                -continued

Phe Gln Gly Ala Lys Val Val Arg Gly Pro Asp Trp Glu Trp Gly Ser
                 60                  65                  70 cag gat gga ggg gaa ggg aaa ccg ggc cgt gtg gtg gac atc cgt ggc        292
Gln Asp Gly Gly Glu Gly Lys Pro Gly Arg Val Val Asp Ile Arg Gly
         75                  80                  85 tgg gat gtg gag aca ggc cgg agt gtg gcc agc gtg acg tgg gct gat        340
Trp Asp Val Glu Thr Gly Arg Ser Val Ala Ser Val Thr Trp Ala Asp
 90                  95                 100 ggt acc acc aat gtg tac cgt gtg ggc cac aag ggc aag gtg gac ctc        388
Gly Thr Thr Asn Val Tyr Arg Val Gly His Lys Gly Lys Val Asp Leu
105                 110                 115                 120 aag tgt gtg ggc gag gca gcg ggc ggc ttc tac tat aag gac cac ctc        436
Lys Cys Val Gly Glu Ala Ala Gly Gly Phe Tyr Tyr Lys Asp His Leu
                125                 130                 135 cca agg ctc ggc aag ccg gcg gag ctg cag cgc agg gtg agt gct gac        484
Pro Arg Leu Gly Lys Pro Ala Glu Leu Gln Arg Arg Val Ser Ala Asp
            140                 145                 150 agc cag ccc ttc cag cac ggg gac aag gtc aag tgt ctg ctg gac act        532
Ser Gln Pro Phe Gln His Gly Asp Lys Val Lys Cys Leu Leu Asp Thr
                155                 160                 165 gat gtc ctg cgg gag atg cag gaa ggc cac ggc ggc tgg aac ccc agg        580
Asp Val Leu Arg Glu Met Gln Glu Gly His Gly Gly Trp Asn Pro Arg
170                 175                 180 atg gcg gag ttt atc gga cag acg ggc acc gtg cat cgt atc acg gac        628
Met Ala Glu Phe Ile Gly Gln Thr Gly Thr Val His Arg Ile Thr Asp
185                 190                 195                 200 cgc ggg gac gtg cgc gtg cag ttc aac cac gag acg cgc tgg acc ttc        676
Arg Gly Asp Val Arg Val Gln Phe Asn His Glu Thr Arg Trp Thr Phe
                205                 210                 215 cac ccc ggg gcg ctc acc aag gcc ctg ggc cgc gtc ggg aag gtg gtg        724
His Pro Gly Ala Leu Thr Lys Ala Leu Gly Arg Val Gly Lys Val Val
            220                 225                 230 aaa gtg ttt gga gac ggg aac ctg cgt gta gca gtc gct ggt cag cgg        772
Lys Val Phe Gly Asp Gly Asn Leu Arg Val Ala Val Ala Gly Gln Arg
                235                 240                 245 tgg acc ttc agc ccc tcc tgc ctg gtg gcc tac cgg ccc gag gag gat        820
Trp Thr Phe Ser Pro Ser Cys Leu Val Ala Tyr Arg Pro Glu Glu Asp
250                 255                 260 gcc aac ctg gac gtg gct gag cgc gcc cgg gag aac aaa agc tca ctg        868
Ala Asn Leu Asp Val Ala Glu Arg Ala Arg Glu Asn Lys Ser Ser Leu
265                 270                 275                 280 agc gtg gcc ctg gac aag ctt cgg gcc cag aag agt gac cca gag cac        916
Ser Val Ala Leu Asp Lys Leu Arg Ala Gln Lys Ser Asp Pro Glu His
                285                 290                 295 ccg gga agg ctg gtg gtg gag gtg gcg ctg ggt aac gca gcc cgg gct        964
Pro Gly Arg Leu Val Val Glu Val Ala Leu Gly Asn Ala Ala Arg Ala
            300                 305                 310 ctg gac ctg ctg cgg agg cgc cca gag cag gtg gac acc aag aac caa       1012
Leu Asp Leu Leu Arg Arg Arg Pro Glu Gln Val Asp Thr Lys Asn Gln
                315                 320                 325 ggc agg acc gct ctg caa gtg gct gcc tac ctg ggc cag gtg gag ttg       1060
Gly Arg Thr Ala Leu Gln Val Ala Ala Tyr Leu Gly Gln Val Glu Leu
330                 335                 340 ata cgg ctg ctg cta caa gcc agg gcg ggc gtg gac ctg ccg gac gac       1108
Ile Arg Leu Leu Leu Gln Ala Arg Ala Gly Val Asp Leu Pro Asp Asp
345                 350                 355                 360 gag ggc aac acg gca ctg cac tac gcg gcc ctg ggg aac cag ccc gag       1156
Glu Gly Asn Thr Ala Leu His Tyr Ala Ala Leu Gly Asn Gln Pro Glu
                365                 370                 375 gcc acc agg gtg ctc ctg agt gct ggg tgc cgg gcg gac gcc atc aac       1204
```

-continued

```
                Ala Thr Arg Val Leu Ser Ala Gly Cys Arg Ala Asp Ala Ile Asn
                                380                 385                 390 agc acc cag agc aca gca ctg cac gtg gcc gtg cag agg ggc ttc ctg        1252
Ser Thr Gln Ser Thr Ala Leu His Val Ala Val Gln Arg Gly Phe Leu
            395                 400                 405 gag gtg gtg cgg gcc ctg tgt gag cgc ggc tgt gac gtc aac ctg ccc        1300
Glu Val Val Arg Ala Leu Cys Glu Arg Gly Cys Asp Val Asn Leu Pro
        410                 415                 420 gac gcc cac tcg gac acg ccc ctg cac tcc gcc atc tcg gcg ggc act        1348
Asp Ala His Ser Asp Thr Pro Leu His Ser Ala Ile Ser Ala Gly Thr
425                 430                 435                 440 gga gcc agc ggc att gtc gag gtc ctc acg gag gtg cca aac atc gat        1396
Gly Ala Ser Gly Ile Val Glu Val Leu Thr Glu Val Pro Asn Ile Asp
                445                 450                 455 gtt acc gcc acc aac agc cag ggt ttc acc ctg ctg cac cat gcc tcc        1444
Val Thr Ala Thr Asn Ser Gln Gly Phe Thr Leu Leu His His Ala Ser
            460                 465                 470 ctc aag ggt cac gcg cta gct gtg aga aag att ctg gct cgg gcg cgg        1492
Leu Lys Gly His Ala Leu Ala Val Arg Lys Ile Leu Ala Arg Ala Arg
        475                 480                 485 cag ctg gtg gac gcc aag aag gag gac ggc ttc acg gcg ctg cat ctg        1540
Gln Leu Val Asp Ala Lys Lys Glu Asp Gly Phe Thr Ala Leu His Leu
490                 495                 500 gct gcc ctc aac aac cac cgc gag gtg gcc cag atc ctc atc cgg gag        1588
Ala Ala Leu Asn Asn His Arg Glu Val Ala Gln Ile Leu Ile Arg Glu
505                 510                 515                 520 ggc cgc tgt gac gtg aac gtg cgc aac cgg aag ctg cag tcc ccg ctg        1636
Gly Arg Cys Asp Val Asn Val Arg Asn Arg Lys Leu Gln Ser Pro Leu
                525                 530                 535 cat ctc gcc gtg caa cag gcc cac gtg ggg ctg gtg ccg cta ctg gtg        1684
His Leu Ala Val Gln Gln Ala His Val Gly Leu Val Pro Leu Leu Val
            540                 545                 550 gac gct ggg tgc agt gtc aac gcc gag gac gag gag ggg gac aca gcc        1732
Asp Ala Gly Cys Ser Val Asn Ala Glu Asp Glu Glu Gly Asp Thr Ala
        555                 560                 565 ctg cac gtg gcg ctg cag cgt cat cag ctg ctg ccc ctg gtg gct gat        1780
Leu His Val Ala Leu Gln Arg His Gln Leu Leu Pro Leu Val Ala Asp
570                 575                 580 ggg gcc ggg ggg gac cca ggg ccc ttg cag ctg ctg tcc agg cta cag        1828
Gly Ala Gly Gly Asp Pro Gly Pro Leu Gln Leu Leu Ser Arg Leu Gln
585                 590                 595                 600 gcc tcg ggc ctc ccc ggc agc gcg gag ctg acg gtg ggc gcg gcg gtc        1876
Ala Ser Gly Leu Pro Gly Ser Ala Glu Leu Thr Val Gly Ala Ala Val
                605                 610                 615 gcc tgc ttc ctg gcg ctg gag ggc gcc gac gtg agc tac acc aac cac        1924
Ala Cys Phe Leu Ala Leu Glu Gly Ala Asp Val Ser Tyr Thr Asn His
            620                 625                 630 cgc ggt cgg agc ccg ctg gac ctg gcc gcc gag ggt cgc gtg ctc aag        1972
Arg Gly Arg Ser Pro Leu Asp Leu Ala Ala Glu Gly Arg Val Leu Lys
        635                 640                 645 gcc ctt cag ggc tgc gcc cag cgc ttc cgg gag cgg cag gcg ggc ggg        2020
Ala Leu Gln Gly Cys Ala Gln Arg Phe Arg Glu Arg Gln Ala Gly Gly
650                 655                 660 ggc gcg gcc ccg ggc ccc agg caa acg ctc ggg acc ccc aac acc gtg        2068
Gly Ala Ala Pro Gly Pro Arg Gln Thr Leu Gly Thr Pro Asn Thr Val
665                 670                 675                 680 acg aac ctg cac gtg ggc gcc gcg ccg ggg ccc gag gcc gct gag tgc        2116
Thr Asn Leu His Val Gly Ala Ala Pro Gly Pro Glu Ala Ala Glu Cys
                685                 690                 695 ctg gtg tgc tcc gag ctg gcg ctg ctg gtg ctg ttc tcg ccg tgc cag        2164
```

```
Leu Val Cys Ser Glu Leu Ala Leu Leu Val Leu Phe Ser Pro Cys Gln
            700                 705                 710 cac cgc acc gtg tgt gag gag tgc gcg cgc agg atg aag aag tgc atc     2212
His Arg Thr Val Cys Glu Glu Cys Ala Arg Arg Met Lys Lys Cys Ile
        715                 720                 725 agg tgc cag gtg gtc gtc agc aag aaa ctg cgc cca gac ggc tct gag     2260
Arg Cys Gln Val Val Val Ser Lys Lys Leu Arg Pro Asp Gly Ser Glu
    730                 735                 740 gtg gcg agc gcc gcc ccc gcc ccc ggc ccg ccg cgc cag ctg gtg gag     2308
Val Ala Ser Ala Ala Pro Ala Pro Gly Pro Pro Arg Gln Leu Val Glu
745                 750                 755                 760 gag ctg cag agc cgc tac cgg cag atg gag gaa cgc atc acc tgc ccc     2356
Glu Leu Gln Ser Arg Tyr Arg Gln Met Glu Glu Arg Ile Thr Cys Pro
                765                 770                 775 atc tgc atc gac agc cac atc cgc ctc gtg ttc cag tgc ggc cac ggc     2404
Ile Cys Ile Asp Ser His Ile Arg Leu Val Phe Gln Cys Gly His Gly
            780                 785                 790 gca tgc gcc ccc tgc ggc tcc gcg ctc agc gcc tgc ccc atc tgc cgc     2452
Ala Cys Ala Pro Cys Gly Ser Ala Leu Ser Ala Cys Pro Ile Cys Arg
        795                 800                 805 cag ccc atc cgc gac cgc atc cag atc ttc gtg tga gccgcgccgt          2498
Gln Pro Ile Arg Asp Arg Ile Gln Ile Phe Val
    810                 815 ccgccgcgcc cgagctgcct tcgcgtgccc ccgccctgtg ttttataaaa agaaagattc   2558
tcgg                                                                 2562

<210> SEQ ID NO 4
<211> LENGTH: 819
<212> TYPE: PRT
<213> ORGANISM: Homo sapiens

<400> SEQUENCE: 4

Met Arg Trp Lys Cys Arg Val Cys Leu Asp Tyr Asp Leu Cys Thr Gln
1               5                   10                  15

Cys Tyr Met His Asn Lys His Glu Leu Ala His Ala Phe Asp Arg Tyr
            20                  25                  30

Glu Thr Ala His Ser Arg Pro Val Thr Leu Ser Pro Arg Gln Gly Leu
        35                  40                  45

Pro Arg Ile Pro Leu Arg Gly Ile Phe Gln Gly Ala Lys Val Val Arg
    50                  55                  60

Gly Pro Asp Trp Glu Trp Gly Ser Gln Asp Gly Gly Glu Gly Lys Pro
65                  70                  75                  80

Gly Arg Val Val Asp Ile Arg Gly Trp Asp Val Glu Thr Gly Arg Ser
                85                  90                  95

Val Ala Ser Val Thr Trp Ala Asp Gly Thr Thr Asn Val Tyr Arg Val
            100                 105                 110

Gly His Lys Gly Lys Val Asp Leu Lys Cys Val Gly Glu Ala Ala Gly
        115                 120                 125

Gly Phe Tyr Tyr Lys Asp His Leu Pro Arg Leu Gly Lys Pro Ala Glu
    130                 135                 140

Leu Gln Arg Arg Val Ser Ala Asp Ser Gln Pro Phe Gln His Gly Asp
145                 150                 155                 160

Lys Val Lys Cys Leu Leu Asp Thr Asp Val Leu Arg Glu Met Gln Glu
                165                 170                 175

Gly His Gly Gly Trp Asn Pro Arg Met Ala Glu Phe Ile Gly Gln Thr
            180                 185                 190

Gly Thr Val His Arg Ile Thr Asp Arg Gly Asp Val Arg Val Gln Phe
```

```
                195                 200                 205
Asn His Glu Thr Arg Trp Thr Phe His Pro Gly Ala Leu Thr Lys Ala
            210                 215                 220

Leu Gly Arg Val Gly Lys Val Lys Val Phe Gly Asp Gly Asn Leu
225                 230                 235                 240

Arg Val Ala Val Ala Gly Gln Arg Trp Thr Phe Ser Pro Ser Cys Leu
                245                 250                 255

Val Ala Tyr Arg Pro Glu Glu Asp Ala Asn Leu Asp Val Ala Glu Arg
            260                 265                 270

Ala Arg Glu Asn Lys Ser Ser Leu Ser Val Ala Leu Asp Lys Leu Arg
            275                 280                 285

Ala Gln Lys Ser Asp Pro Glu His Pro Gly Arg Leu Val Glu Val
        290                 295                 300

Ala Leu Gly Asn Ala Ala Arg Ala Leu Asp Leu Leu Arg Arg Arg Pro
305                 310                 315                 320

Glu Gln Val Asp Thr Lys Asn Gln Gly Arg Thr Ala Leu Gln Val Ala
                325                 330                 335

Ala Tyr Leu Gly Gln Val Glu Leu Ile Arg Leu Leu Gln Ala Arg
            340                 345                 350

Ala Gly Val Asp Leu Pro Asp Asp Glu Gly Asn Thr Ala Leu His Tyr
            355                 360                 365

Ala Ala Leu Gly Asn Gln Pro Glu Ala Thr Arg Val Leu Leu Ser Ala
            370                 375                 380

Gly Cys Arg Ala Asp Ala Ile Asn Ser Thr Gln Ser Thr Ala Leu His
385                 390                 395                 400

Val Ala Val Gln Arg Gly Phe Leu Glu Val Val Arg Ala Leu Cys Glu
                405                 410                 415

Arg Gly Cys Asp Val Asn Leu Pro Asp Ala His Ser Asp Thr Pro Leu
            420                 425                 430

His Ser Ala Ile Ser Ala Gly Thr Gly Ala Ser Gly Ile Val Glu Val
            435                 440                 445

Leu Thr Glu Val Pro Asn Ile Asp Val Thr Ala Thr Asn Ser Gln Gly
450                 455                 460

Phe Thr Leu Leu His His Ala Ser Leu Lys Gly His Ala Leu Ala Val
465                 470                 475                 480

Arg Lys Ile Leu Ala Arg Ala Arg Gln Leu Val Asp Ala Lys Lys Glu
                485                 490                 495

Asp Gly Phe Thr Ala Leu His Leu Ala Ala Leu Asn Asn His Arg Glu
            500                 505                 510

Val Ala Gln Ile Leu Ile Arg Glu Gly Arg Cys Asp Val Asn Val Arg
            515                 520                 525

Asn Arg Lys Leu Gln Ser Pro Leu His Leu Ala Val Gln Gln Ala His
            530                 535                 540

Val Gly Leu Val Pro Leu Leu Val Asp Ala Gly Cys Ser Val Asn Ala
545                 550                 555                 560

Glu Asp Glu Glu Gly Asp Thr Ala Leu His Val Ala Leu Gln Arg His
                565                 570                 575

Gln Leu Leu Pro Leu Val Ala Asp Gly Ala Gly Asp Pro Gly Pro
            580                 585                 590

Leu Gln Leu Leu Ser Arg Leu Gln Ala Ser Gly Leu Pro Gly Ser Ala
            595                 600                 605

Glu Leu Thr Val Gly Ala Ala Val Ala Cys Phe Leu Ala Leu Glu Gly
            610                 615                 620
```

```
Ala Asp Val Ser Tyr Thr Asn His Arg Gly Arg Ser Pro Leu Asp Leu
625                 630                 635                 640

Ala Ala Glu Gly Arg Val Leu Lys Ala Leu Gln Gly Cys Ala Gln Arg
            645                 650                 655

Phe Arg Glu Arg Gln Ala Gly Gly Ala Ala Pro Gly Pro Arg Gln
            660                 665                 670

Thr Leu Gly Thr Pro Asn Thr Val Thr Asn Leu His Val Gly Ala Ala
            675                 680                 685

Pro Gly Pro Glu Ala Ala Glu Cys Leu Val Cys Ser Glu Leu Ala Leu
690                 695                 700

Leu Val Leu Phe Ser Pro Cys Gln His Arg Thr Val Cys Glu Glu Cys
705                 710                 715                 720

Ala Arg Arg Met Lys Lys Cys Ile Arg Cys Gln Val Val Val Ser Lys
                725                 730                 735

Lys Leu Arg Pro Asp Gly Ser Glu Val Ala Ser Ala Ala Pro Ala Pro
                740                 745                 750

Gly Pro Pro Arg Gln Leu Val Glu Glu Leu Gln Ser Arg Tyr Arg Gln
                755                 760                 765

Met Glu Glu Arg Ile Thr Cys Pro Ile Cys Ile Asp Ser His Ile Arg
770                 775                 780

Leu Val Phe Gln Cys Gly His Gly Ala Cys Ala Pro Cys Gly Ser Ala
785                 790                 795                 800

Leu Ser Ala Cys Pro Ile Cys Arg Gln Pro Ile Arg Asp Arg Ile Gln
                805                 810                 815

Ile Phe Val

<210> SEQ ID NO 5
<211> LENGTH: 44
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

His Ser Asn Ser Cys Ala Gly Cys Arg Lys Glu His Ile Val Met Arg
 1               5                  10                  15

Trp Lys Cys Arg Val Cys Leu Asp Tyr Asp Leu Cys Thr Gln Cys Tyr
            20                  25                  30

Met His Lys His Glu Leu Ala His Ala Phe Asp Arg
        35                  40

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 6 ctawwwwtar                                                      10
```

METHODS AND COMPOSITIONS INVOLVING NUCLEOTIDE REPEAT DISORDERS

This application is a national phase application under 35 U.S.C. §371 of International Application No. PCT/US2007/066470 filed Apr. 11, 2007, which claims benefit of priority to U.S. Provisional Application Ser. No. 60/791,071, filed Apr. 11, 2006, both of which are incorporated by reference in their entirety.

BACKGROUND OF THE INVENTION

1. Field of the Invention

The present invention relates generally to the fields of molecular biology and medicine. More particularly, it concerns methods and compositions for identifying candidate therapeutic and preventative agents and for treating or preventing diseases, disorders and conditions involving trinucleotide repeats.

2. Description of Related Art

Myotonic dystrophy, the most common adult-onset muscular dystrophy in humans, is characterized by the severe dysfunction of skeletal and smooth muscle structure and function (Harper, 2001; Groenen and Wiering a, 1998; Mankodi and Thornton, 2002; Amack and Mahadevan, 2004). Delayed muscle differentiation and hypotonia are the predominant features in congenital myotonic dystrophy type 1 (DM1) whereas myotonia, atrophy and weakness of skeletal muscle are the features in adult onset DM1 (Harper, 2001; Sarnat and Silbert, 1976; Farkas-Bargeton et al., 1988; Sahgal et al., 1983). Several dystrophic changes of smooth muscles are also common in DM1 (Lenard et al., 1977; Brunner et al., 1992; Ronnblom et al., 1999; Ronnblom et al., 2002). DM1 genetic mutation is the expansion of a CTG repeat in the 3' un-translated region of DMPK on chromosome 19q13.3 and DM2 (myotonic dystrophy type 2) genetic mutation is the expansion of a CCTG repeat in the first intron of ZNF9 located on chromosome 3q21.3 (Fu et al, 1992; Brook et al., 1992; Mahadevan et al., 1992; Liguori et al., 2001.

In DM1, the length of the CTG repeat shows a strong correlation with the complexity and severity of disease phenotypes; short to moderate expansion causes milder muscle defects whereas expansions larger than 3 kb cause more severe dystrophic muscle defects (Harper, 2001; Monckton and Ashizawa, 2004; Nagamitsu and Ashizawa, 2002). In contrast, DM2 phenotypes are more subtle and DM2 patients do not develop congenital muscle defects in spite of very large repeat expansion (Day et al., 1999; Day et al., 2003). In DM1, transcription of the mutant DMPK allele produces mRNA encoding expanded CUG sequences; in DM2, the transcription of ZNF9 produces mRNA that carries expanded CCUG sequences. The CUG and CCUG RNA cause cellular toxicity, but the mechanism by which expanded CUG and CCUG RNA cause such cellular toxicity has not been elucidated completely (Mankodi et al., 2003; Kanadia et al., 2003; Jiang et al., 2004; Day and Ranum, 2005; Ranum L P, Day, 2004). Transgenic mice expressing short stretches of CUG repeats (approximately 250 repeats) in skeletal muscle develop myotonia and several structural defects reminiscent of DM1 (Mankodi et al., 2000) Sequestration of muscle-blind proteins by expanded CUG RNA was found to be the pathogenic mechanism in the muscle defects found in the CUG transgenic mice (Mankodi et al., 2002). Subsequent studies with muscle-blind (Mbnl1) knockout mice confirmed that the loss of muscle-blind function is indeed one of the important mechanistic steps required to inflict muscle defects in DM1 (Kanadia et al., 2003). Importantly, neither Mbnl1 knockout mice nor the available CUG transgenic mice develop dystrophic muscle defects, the hallmark clinical features of adult onset and congenital DM1 (Kanadia et al., 2003; Mankodi et al., 2000). These complex muscle defects include severe muscle weakness, wasting, degeneration of muscle fibers and developmental abnormalities of skeletal muscle fibers.

Therefore, there remains a need to recapitulate the physiological context of DM1 in order to identify key proteins involved in DM1, and thus allow for the identification and development of appropriate therapeutic and preventative agents for the disease.

Moreover, DM1 represents an example of a disease associated with repeat sequences in nucleic acid molecules. Many other diseases, as well as conditions and disorders, do not have cures, cannot be prevented, or are not effectively treated. These would benefit from compositions and methods that would elucidate the mechanisms behind their pathologies so as to lead to the identification and development of candidate drugs. Consequently, there is a need for methods and compositions that would provide information regarding other diseases, conditions, and disorders associated with repeat sequences.

SUMMARY OF THE INVENTION

The present invention is based on a number of scientific advancements related to nucleic acids with long stretches of nucleotide repeats and the disorders and diseases associated with such nucleic acids. Such nucleic acids are characterized by a region of 50 or more contiguous repeats of two or more nucleotide sequences. Consequently, the present invention is directed to general methods and compositions involving these nucleic acids and particular methods and compositions concerning the prevention and/or treatment of disorders, conditions, and diseases associated with repeats in nucleic acids, such as DM1.

In some embodiments of the invention, there are compositions including nucleic acids having nucleotide repeat sequences, including extensive nucleotide repeat sequences, and/or capable of expressing such sequences. A nucleotide repeat will generally be understood to be a repeat that is at least two residues. The repeat can have, have at least, or have at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more residues that constitute a repeat sequence, or any range derivable therein. In certain embodiments, repeat is a trinucleotide repeat or a quadruple- or di-nucleotide repeat. The term "extensive nucleotide repeat sequences" refers to a region with at least 500 nucleotide repeats. It is contemplated that nucleic acids of the invention have between 100 and 5000 nucleotide repeats, meaning they may have at least, at most, or between 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, or 10000 repeats, or any range derivable therein. It is noted that nucleic acids of the invention will not be exactly, for instance, 100 repeats, but that it may be any integer falling within a specified range. Moreover, because various conditions and diseases involve repeats with different numbers of nucleotides, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 or more nucleotides in a single repeat, the number of nucleotides constituting the region will similarly vary. In some embodiments of the invention, the region is characterized as at least, at most, or as having 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 11100, 11200, 11300, 11400, 11500, 11600, 11700, 11800, 11900, 12000, 12100, 12200, 12300, 12400, 12500, 12600, 12700, 12800, 12900, 13000, 13100, 13200, 13300, 13400, 13500, 13600, 13700, 13800, 13900, 14000, 14100, 14200, 14300, 14400, 14500, 14600, 14700, 14800, 14900, 15000, 15100, 15200, 15300, 15400, 15500, 15600, 15700, 15800, 15900, 16000, 16100, 16200, 16300, 16400, 16500, 16600, 16700, 16800, 16900, 17000, 17100, 17200, 17300, 17400, 17500, 17600, 17700, 17800, 17900, 18000, 18100, 18200, 18300, 18400, 18500, 18600, 18700, 18800, 18900, 19000, 19100, 19200, 19300, 19400, 19500, 19600, 19700, 19800, 19900, 20000, 21000, 21100, 21200, 21300, 21400, 21500, 21600, 21700, 21800, 21900, 22000, 22100, 22200, 22300, 22400, 22500, 22600, 22700, 22800, 22900, 23000, 23100, 23200, 23300, 23400, 23500, 23600, 23700, 23800, 23900, 24000, 24100, 24200, 24300, 24400, 24500, 24600, 24700, 24800, 24900, 25000, 25100, 25200, 25300, 25400, 25500, 25600, 25700, 25800, 25900, 26000, 26100, 26200, 26300, 26400, 26500, 26600, 26700, 26800, 26900, 27000, 27100, 27200, 27300, 27400, 27500, 27600, 27700, 27800, 27900, 28000, 28100, 28200, 28300, 28400, 28500, 28600, 28700, 28800, 28900, 29000, 29100, 29200, 29300, 29400, 29500, 29600, 29700, 29800, 29900, or 30000 nucleotides, or any range derivable therein. Any embodiments involving nucleic acids with nucleotide repeats may be characterized as discussed in this paragraph.

Such nucleic acids may be RNA or DNA. It is specifically contemplated that nucleic acids with the repeats discussed above may be RNA transcripts or DNA encoding such transcripts. Moreover, DNA encoding such transcripts are vectors in certain embodiments of the invention. In particular embodiments, the vector is a plasmid, such as one that can be replicated in bacteria. The present invention overcomes previous problems with producing plasmids encoding nucleic acids with extensive nucleotide repeat sequences because of the instability of such plasmids in bacteria. Therefore, the present invention concerns compositions comprising DNA plasmids encoding RNA transcripts with extensive nucleotide repeat sequences, as well as methods of producing such DNA plasmids, particularly in useful quantities.

In certain embodiments, the RNA molecules of the invention are transcripts from a dystrophia myotonica protein kinase (DMPK) gene or coding sequence. It is particularly contemplated that the RNA molecules are transcripts from a mutant DMPK gene, which is generally understood to be a gene with at least 40 repeats since 1 to 40 repeats typically yields a normal phenotype. The DMPK gene or coding sequence may encode for an RNA molecule with more repeats and disclosed throughout this application. A DMPK human coding sequence is provided by Genbank Accession Number L19268, which is hereby incorporated by reference. A nucleic acid sequence for a wild-type, nonmutant DMPK human sequence is provided as SEQ ID NO:1 (a wild-type sequence would be any sequence with less than 40 repeats in the repeat region) and an example of a mutant sequence is SEQ ID NO:2 (a mutant sequence would be any sequence with greater than 40 repeats in the repeat region, in contrast to, for example, SEQ ID NO:1). Thus, any embodiment in the context of an RNA molecule with a nucleotide repeat sequence may be employed in the context of a DMPK transcript, and vice versa. Therefore, the embodiments with different repeat sequences may be applied to DMPK transcripts as well.

Furthermore, the present invention concerns host cells that contain vectors of the invention. It is contemplated that in some embodiments, host cells may have a plasmid with a nucleic acid sequence encoding an RNA molecule with an extensive nucleotide repeat region. In certain embodiments, the RNA molecule has 100 to 10,000 nucleotide repeats (or any of the repeat numbers or ranges, as well as nucleotides, discussed above), wherein the sequence is operatively connected to a promoter, which may or may not be heterologous with respect to the nucleic acid sequence. In further embodiments, the host cell is a eukaryotic cell. It is contemplated to be a mammalian cell in some embodiments. Moreover, the mammalian cell may be a muscle cell or an embryonic stem cell in additional embodiments. Alternatively, the host cell may be a prokaryotic cell. In some instances, the host cell is a bacteria cell, particularly one capable of replicating the plasmid. Accordingly, in some embodiments the plasmid is episomal in the cell, while in other embodiments, it becomes integrated into the host cell's genome. In the latter embodiment, it is further contemplated that such host cells may be used to generate transgenic animals.

Consequently, additional embodiments of the invention include a transgenic animal with a transgene encoding an RNA molecule having an extensive nucleotide repeat region. In certain embodiments, the RNA molecule is between 300 and 15000 residues in length or it may have between 100 and 5000 nucleotide repeats. It is contemplated that in some embodiments, the animal is a mammal. In further embodiments, the animal is a mouse. Additionally, some embodiments involve trinucleotide repeats. In certain cases, the trinucleotide repeat is a CUG or CAG.

As mentioned above, the present invention also concerns methods for producing plasmids encoding an RNA molecule having an extensive nucleotide repeat region. In certain embodiments, the RNA molecule is between 300 and 15000 residues in length or it may have between 100 and 5000 nucleotide repeats. Moreover, it is specifically contemplated that in some embodiments, the repeats may be trinucleotide repeats. In some cases, the repeat is a CAG or CUG trinucleotide repeat. Methods of the invention may involve growing bacteria having a plasmid containing a DNA sequence encoding the RNA molecule at a temperature range between about 8° C. and about 16° C., wherein the plasmid is replicated in the bacteria. The temperature at which the bacteria may be cultured and/or grown may be at least, at most, or the following temperatures: about 8, 9, 10, 11, 12, 13, 14, 15, or 16° C., or any range derivable therein. In particular embodiments, once bacteria contain a plasmid encoding an RNA molecule having an extensive nucleotide repeat region, they are not grown or cultured at a temperature greater than about 16° C.

Those of skill in the art are well informed about media and other culture conditions such as $CO_2$ concentrations for bacterial growth. It is contemplated that generally the bacteria maintain and replicate the plasmid while growing in that temperature range. In certain embodiments, it is contemplated that the bacteria may be grown in that temperature range for at least, at most, or within 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, and/or 5 weeks or more, or any range derivable therein. The bacteria may also be incubated at temperatures outside the specified range(s) so long as they are grown for some period of time within in range to replicate and maintain the plasmid. In certain embodiments, the bacteria are grown at the temperature range for at least or at most 2, 3, 4, 5, 6, 7, 8, 9, 10, 11, 12, 13, 14, 15 days or more.

In additional methods of producing a plasmid encoding an RNA molecule with an extensive nucleotide repeat region, the replicated plasmid may be isolated from the bacteria. Moreover, the isolated bacteria may then be used for other recombinant DNA methods, such as, but not limited to, transfection into a host cell or in vitro transcription.

The nucleic acids above were and may be used to identify and characterize mechanisms underlying the physiology of nucleotide repeat diseases and conditions. These nucleic acids provided distinct advantages because the length of the nucleotide repeat region more closely simulates physiological conditions of, for instance, DM1.

Therefore, the present invention provides methods of using nucleic acids with or encoding extensive nucleotide repeat regions.

Methods of the invention include methods for screening for a molecule involved in a disease or condition characterized by a mutation in a gene with a nucleotide repeat sequence comprising obtaining a cell with a recombinant expression region encoding RNA molecules having between 100 and 5000 nucleotide repeats and identifying any molecule that is sequestered by the RNA molecules expressed from the region, wherein the sequestered protein is potentially involved in the disease or condition. These methods concern identifying molecules that physically associate directly or indirectly with RNA molecules having a nucleotide repeat sequence. It is contemplated to be useful in the context of disease and/or conditions that are characterized by at least one gene that is considered mutant or mutated because of the number or length of nucleotide repeats in the gene. Such diseases and conditions are discussed further in this disclosure.

Other methods of the invention include methods of screening for a candidate therapeutic agent for the treatment of myotonic dystrophy type 1 (DM1) comprising: a) incubating a skeletrophin polypeptide with RNA molecules containing 100 to 5000 CUG or CAG trinucleotide repeats under conditions in which the skeletrophin polypeptide associates with the RNA molecules; b) incubating a candidate compound with the RNA molecules, skeletrophin polypeptide, or both; and c) determining whether the candidate compound disrupts or inhibits the association between the skeletrophin polypeptide and the RNA molecules, wherein a candidate compound that disrupts the association is a candidate therapeutic agent. The different embodiments discussed above and below can be specifically implemented in the context of this method of the invention.

In other embodiments of the invention there are methods for screening for a candidate therapeutic agents for a disease and/or condition involving a nucleic acid with a an extensive nucleotide repeat sequence comprising: a) obtaining recombinant RNA molecules containing a nucleotide repeat sequence between 300 and 1,500 residues in length; b) incubating the recombinant RNA molecules with a protein that is sequestered by the RNA molecules under conditions to allow sequestration of the protein; c) incubating a candidate compound with the recombinant RNA molecules, protein, or both; and d) assaying whether the candidate compound disrupts sequestration of the protein by the RNA molecules; wherein a candidate compound that disrupts sequestration is a candidate therapeutic agent.

In certain methods of the invention, a skeletrophin polypeptide is used as a protein that associates with an RNA molecule, such as a DMPK transcript, with an extensive nucleotide repeat sequence. In those embodiments, the skeletrophin polypeptide and the RNA molecules may be in a cell containing a recombinant expression region encoding the RNA molecules. Such a cell may have been transfected with a plasmid containing the expression region. DMPK transcripts are mutated (i.e., 40 repeats or more) in certain embodiments of the invention.

Some embodiments of the invention involve determining whether the candidate compound disrupts or inhibits the association between the skeletrophin polypeptide and the RNA molecules involves assaying for sequestration of the skeletrophin polypeptide, wherein a decrease in sequestration identifies the candidate compound as a candidate therapeutic agent. In other embodiments, determining whether the candidate compound disrupts or inhibits the association between the skeletrophin polypeptide and the RNA molecules involves assaying Notch activity, wherein a decrease in Notch activity identifies the candidate compound as a candidate therapeutic agent. The skilled person is aware of a number of assays for Notch activity. Additionally, in some embodiments, determining whether the candidate compound disrupts or inhibits the association between the skeletrophin polypeptide and the RNA molecules involves assaying for binding between the skeletrophin polypeptide and the RNA molecules, wherein a reduction or inhibition of binding identifies the candidate compound as a candidate therapeutic agent. Other ways to assay whether the candidate compound disrupts or inhibits sequestration of skeletrophin by the RNA molecules include assaying for E3 ubiquitin ligase activity by skeletrophin or by measuring Jagged2 and/or Notch1 expression levels.

The invention also includes methods for screening for a candidate therapeutic agents for a disease and/or condition involving a nucleic acid with a an extensive nucleotide repeat sequence comprising: a) obtaining recombinant RNA molecules containing a nucleotide repeat sequence between 300 and 1,500 residues in length; b) incubating the recombinant RNA molecules with a protein that is sequestered by the RNA molecules under conditions to allow sequestration of the protein; c) incubating a candidate compound with the recombinant RNA molecules, protein, or both; and d) assaying whether the candidate compound disrupts or inhibits sequestration of the protein by the RNA molecules; wherein a candidate compound that disrupts or inhibits sequestration is a candidate therapeutic agent.

In additional embodiments of the invention there are methods of screening for a candidate downregulator of Notch comprising: a) incubating a skeletrophin polypeptide with RNA molecules containing 100 to 5000 CUG or CAG trinucleotide repeats under conditions in which the skeletrophin polypeptide associates with the RNA molecule; b) incubating a candidate compound with the RNA molecules, skeletrophin polypeptide, or both; and c) determining whether the candidate compound disrupts or inhibits the association between the skeletrophin polypeptide and the RNA molecules; wherein a candidate compounds that disrupts the association is a candidate downregulator of Notch. The term "downregulator" in the context of Notch refers to an agent that reduces the amount of Notch activity compared to when that agent is absent. The reduction is contemplated in some embodiments to be the result of inhibition or prevention of Notch activation.

Other methods include a method of screening for a candidate downregulator of Notch comprising: a) exposing a candidate compound to DM1 cells having a Notch-responsive promoter operably connected to a reporter gene; b) comparing the level of expression of the reporter gene in the presence and absence of the candidate compound, wherein a compound that reduces Notch signaling is a candidate downregulator of Notch. Promoters that are affected by Notch activity and activation (Notch-responsive promoter) may be employed in embodiments of the invention. In some cases, the Notch-responsive promoter comprises one or more CBF1-Notch binding sites in the promoter of the reporter gene. In certain embodiments, the reporter gene is enzymatic (e.g., luciferase, chloramphenicol acetyl transferase), colorimetric (e.g., β-galactosidase), or fluorescent (e.g., green fluorescent protein). It is specifically contemplated that the DM1 cells used in this method of screening can be used with non-DM1 cells as well. In certain embodiments, the cells used are myocytes, osteoblasts, neuroblasts, myoblasts, or muscle cells. The cells may or may not reflect a disease state.

It is specifically contemplated that screening methods of the invention may further include a step of administering the candidate compound to a subject and assaying for muscle loss and/or wasting after administration. Moreover, in some embodiments, the subject has or is at risk for muscle loss or wasting. In certain embodiments, the subject has myotonic dystrophy (or some other muscular dystrophy), Type II Diabetes mellitus, cancer, AIDS, sepsis, Cushing Syndrome or muscle atrophy. The subject may be a human subject (patient) or a subject may also be an animal. The animal may represent an animal model for a disease state or condition, including those discussed above.

Another method of the invention is for inhibiting Notch activation in a DM1 cell comprising providing to the cell a skeletrophin agent. Notch is a protein that becomes activated under certain conditions. In particular contexts, it is desirable to prevent or inhibit Notch activation and the downstream effects of Notch activation. The term "skeletrophin agent" refers to a compound or substance that provides unsequestered—i.e., free—skeletrophin in a cell.

In some embodiments, the skeletrophin agent is skeletrophin protein. In particular cases, a cell is provided with skeletrophin protein by administering to the cell a nucleic acid encoding skeletrophin. In additional embodiments, a nucleic acid that encodes skeletrophin is provided to the cell or subject. The nucleic acid may be in a vector. In particular embodiments, the vector is a viral vector. In certain embodiments, the cell is provided with skeletrophin protein by administering to the cell a composition comprising purified skeletrophin protein. In other embodiments, the skeletrophin agent is a small molecule.

The term "providing" is used throughout this application according to its ordinary and plain meaning of to "supply or furnish for use," which means, for example, that a prodrug form of a skeletrophin agent can be administered to the cell or such an agent (or prodrug form) can be prescribed to a subject having such a cell.

Other methods of the invention include treating a patient with DM1 comprising providing to the patient an agent that inhibits Notch activation in muscle cells of the patient. Furthermore, the present invention concerns preventing or inhibiting muscle loss or wasting in a patient comprising providing to the patient an agent that inhibits Notch activation in muscle cells of the patient. It is specifically contemplated that these methods may also be implemented to inhibit Notch activation in myocytes, osteoblasts, neuroblasts, and/or myoblasts, in addition to or instead of muscle cells.

In all therapeutic methods of the invention, a step of identifying a subject in need of the therapy (treatment or prevention) may be included. In certain embodiments, the subject has, has been diagnosed with, and/or is at risk for Type II Diabetes mellitus, cancer, AIDS, sepsis, Cushing Syndrome, Huntington's Disease, or muscle disuse.

It is contemplated that "disrupt" is used throughout this application according to its ordinary and plain meaning of "to break apart." The term "inhibit" is used throughout this application according to its ordinary meaning of "to hinder, prevent, or stop."

The term "candidate therapeutic agent" refers to an agent for which there is some evidence of potential therapeutic efficacy. The term candidate compound refers to a compound that may or may not have been previously evaluated for any therapeutic application, particularly in the context of a disease or condition involving a nucleotide repeat sequence. Any candidate therapeutic agent or candidate compound may be implemented as the "agent" for achieving a particular physiological effect, as provided by methods of the invention.

The term "effective amount" may be introduced into any embodiment of the invention. In certain embodiments, methods involve providing an effective amount of a candidate therapeutic agent or other agent to achieve a particular goal. In some embodiments, the goal is a therapeutic benefit with respect to DM1 or a physiological benefit that results from inhibition of Notch or Notch activation or from upregulation or PGC-1α. Such physiological benefits include, but are not limited to, prevention and/or treatment of muscle loss, prevention and/or treatment of muscle wasting, enhancing mitochondrial biogenesis, enhancing oxidative capacity, enhancing fatty acid metabolism. Enhancing glucose metabolism, and/or blocking progressive muscle loss. The invention includes methods of achieving one or more of these physiological benefits.

In embodiments of the invention, a candidate compound is a small molecule, protein, or nucleic acid. Consequently, candidate therapeutic agents may also be a small molecule, protein, or nucleic acid. The present invention specifically includes such candidate compounds and candidate therapeutic agents, including those identified and/or characterized by screening methods or therapeutic methods of the invention. Such agents and compounds may be in a pharmaceutically acceptable formulation.

In particular embodiments, the candidate compound or candidate therapeutic agent is a protein that is a peptide or antibody. A peptide refers to amino acid molecule with 100 or fewer amino acid residues. In certain embodiments, the peptide has, has at least, or has at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids, or any range derivable therein. Particular embodiments concern a peptide that is between 5 and 100 residues in length and has at least 80% identity or similarity to an amino acid sequence of human skeletrophin, which has a protein sequence of GenBank Accession Number AK097106 (also NP543151.1), which is hereby incorporated by reference (nucleic acid sequence in SEQ ID NO:3 and protein sequence is SEQ ID NO:4). It is further contemplated that any peptide or protein in methods or compositions of the invention may have, have at least, or have at most 60, 65, 70, 75, 80, 85, 90, 95, 96, 97, 98, 99, 99.5% identity or similarity, or any range derivable therein, to an amino acid sequence within human skeletrophin. Moreover, polypeptides (which may be longer than 100 amino acids) that are identical or similar to human skeletrophin are also contemplated in the context of the present invention.

The term identity in the context of a percentage means that the protein has a sequence along its length that contains 80% of the amino acids of human skeletrophin along that same length. The term similarity means that in the context of a percentage number a protein has a sequence along its length in which 80% of the amino acids of it are identical to or represent exemplary substitutions of (Table 3 herein) the amino acids of human skeletrophin along that same length. In particular other embodiments, a protein (or a peptide) contains, contains at least, or contains at most 5, 10, 15, 20, 25, 30, 35, 40, 45, 50, 60, 70, 80, 90, 100, 110, 120, 130, 140, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000, 1005, 1110, or 1113 contiguous amino acids of human skeletrophin, or any range derivable therein. In particular embodiments of the invention, the protein or peptide has a contiguous amino acid sequence from the sequence HSNSCAGCRKEHIVMRWKCRVCLDY-DLCTQCYMHKHELAHAFDRY (SEQ ID NO:5).

In certain other embodiments, a candidate substance or candidate therapeutic agents may be an antibody such as a monoclonal or polyclonal antibody; moreover, it may be a humanized antibody, a single chain antibody, or a bi-specific antibody.

It is further contemplated that any embodiment involving a peptide or other protein may be implemented with a nucleic acid encoding the peptide or other protein, which may or may not be contained in a vector. Also, any embodiments involving a nucleic acid may generally be implemented using a vector. Such a vector may be a viral vector. Viral vectors include, but are not limited to, an adeno-associated virus vector, an adenovirus vector, an alphavirus vector, a herpesvirus vector, a lentivirus vector, a parvovirus vector, a picornavirus, a poxvirus vector, a retrovirus vector, Sindbis virus vector, or vaccinia virus vector. It may further contain vector embodiments also discussed herein.

Methods and compositions of the invention include a candidate substance or candidate therapeutic agent that inhibits γ-secretase, which is involved in Notch activation. Again, the substance or agent may be a small molecule, protein, or nucleic acid. As nucleic acid agent may be an siRNA that targets γ-secretase. In certain embodiments, substance or agent is a peptide that inhibits γ-secretase. Particular peptides include, but are not limited to, L-685, 458, or MDL-28170, which are commercially available, γ-secretase inhibitors I, II, III, IV, V and VI (available from EMD Biosciences), and γ-secretase inhibitors such as IX, X, XI, XII, XIII, XVI, XVII, XIX, XX and XXI. These γ-secretase inhibitors may also be referred to as arylsulfonamide (AS), a dibenzazepine (DBZ), or a benzodiazepine (BZ), which may be employed in treatment methods of the invention. Other Notch inhibitors that may be implemented in methods of the invention include Tetrahydroquinoline sulphonamide carbamate 3, Tetrahydroquinoline sulphonamide carbamate 4, Pyrrolidine-sulphonamide carbamate 6, MK-0752 (Merck).

Other candidate substances or candidate therapeutic agents may inhibit Jagged2, the Notch ligand, HES, HERP, mutant DMPK transcripts, or upregulators of PGC-1α. An "upregulator of PGC-1α" refers to an agent that increases the amount of PGC-1α activity compared to when that agent is absent. In certain embodiments, the PGC-1α upregulator is PGC-1α itself, either as an encoded nucleic acid or protein. Methods described herein regarding the use of nucleic acids and proteins in cells may be implemented with respect to PGC-1α upregulators. Therefore, embodiments of the invention include the use of a vector, such as those described herein, for administration to a cell. Viral vectors are specifically contemplated.

Methods involving RNA molecules with a nucleotide repeat sequence may further involve producing the RNA molecules prior to using them. In certain embodiments, producing the RNA molecules involves: growing bacteria with a plasmid containing an expression construct to express the RNA molecules at a temperature between about 8 and about 16° C.; and, isolating the plasmid from the bacteria. Additional embodiments regarding the production of the RNA molecules is provided in other parts of this disclosure.

Methods of the invention involving such RNA molecules may also include a step of either transcribing in vitro the RNA molecule using an isolated plasmid or transfecting the plasmid into cells prior to using the RNA molecule in a screening assay.

The different embodiments discussed above and below can be specifically implemented in the context of this method of the invention. For instance, in some embodiments, the different embodiments regarding RNA molecules is contemplated in the context of the present invention. In certain embodiments, for example, the nucleotide repeats are trinucleotide repeats, such as CUG or CAG repeats.

In certain other embodiments, methods involve a vector encoding an RNA molecule with a nucleotide repeat sequence. The vector will contain an expression region that encodes the RNA molecule. The expression region may include a heterologous promoter or other nucleic acids sequences that are heterologous to the host cell or expression region. The term "heterologous" is used relative to the context of the nucleic acid. A nucleic acid may be heterologous with respect to an adjacent sequence or with respect to a host cell.

It is contemplated that methods and compositions of the invention may include nucleic acid molecules, such as RNA molecules, that are isolated and/or recombinant. In certain embodiments, the RNA molecule is isolated, which means it may be separated from non-nucleic acids, from other nucleic acids, or from a cell. Moreover, it is contemplated the isolated RNA molecule may be isolated and capable of further use or manipulation. In additional embodiments, the RNA molecule is recombinant (the direct or replicated product of recombinant technology). The compositions of RNA molecules described above may be implemented in any method of the invention. These different RNA molecules are discussed above.

In certain embodiments, RNA molecules and a skeletrophin polypeptide are in a cell. Cells of the invention may be eukaryotic or prokaryotic. In certain embodiments, the cell is a muscle cell, such as a mammalian muscle cell. In even further embodiments, the cell is a DM1 cell. Such a cell may be in or from a transgenic animal, and further embodiments are discussed above. Additionally, cells that may be employed in methods of the invention include, but are not limited to, myocytes, osteoblasts, neuroblasts, myoblasts, and/or muscle cells. It is specifically contemplated that any method discussed in the context of muscle cells may be implemented with respect to myoblasts.

In some screening embodiments, methods may also include administering or providing the candidate therapeutic compound to an animal model for DM1 and evaluating the compound for a therapeutic effect. In additional embodiments, the animal model for DM1 comprises a transgene for expressing RNA molecules having at least 500 number of CAG or CUG trinucleotide repeats or any other RNA molecule discussed above. For instance, in some embodiments, the RNA molecules are DMPK transcripts.

Other embodiments of methods of the invention may also involve identifying a candidate therapeutic agent. This may be done, for instance, in the context of a high throughput screen or some other screen involving multiple compounds whose identity is not known at the time of the initial screen.

Further embodiments can involve manufacturing or producing the candidate therapeutic agent. In additional embodiments, screening methods may include validating the candidate therapeutic agent as a therapeutic agent, which means subjecting the candidate therapeutic agent to additional assays or tests to provide further evidence of its use as a therapeutic agent. Such assays or tests may concerns issues of efficacy as a therapy. In even further embodiments, screening methods may involve providing the therapeutic agent to a subject in need thereof or with the relevant physiology for evaluating the agent.

Other methods of the invention include methods of treating a patient with DM1 comprising providing to the patient an agent that inhibits Notch activation in muscle cells of the patient.

Additional embodiments include methods of treating a patient with DM1 comprising providing to the patient an agent that inhibits Notch activation in muscle cells of the patient.

An agent may be any candidate therapeutic agent discussed above that has been validated. Such agents may be a nucleic acid, protein, or small molecule. In certain embodiments, the agent is a skeletrophin agent. In other embodiments, the agent is a Notch inhibitor and/or PGC-1α upregulator.

Embodiments of the invention may involve providing or directly administering a candidate substance or a candidate therapeutic agent to a cell. In certain embodiments, the cell may be in a subject, including a human patient. Substances and agents may be provided to a cell or subject by administering it or a prodrug form intramuscularly, orally, intravenously, or subcutaneously.

Other methods of the invention include screening for a candidate compound that counteracts Notch activation comprising a) assessing PGC-1α expression in cells exposed to a substance and b) comparing PGC-1α expression to PGC-1α expression in a cell not exposed to the substance, wherein the substance is a candidate compound If PGC-1α expression is increased in the cell exposed to the substance. In further embodiments, methods include contacting cells with the candidate compound and evaluating Notch activity. It is contemplated that the same or different cells may be evaluated for PGC-1α expression and Notch activity. Moreover, comparisons may be made to a control that is evaluated at the same time as the candidate compound or to a reference level previously generated.

In some embodiments, PGC-1α expression is assessed by measuring expression of one or more PGC-1α target genes or of PGC-1α. Such target genes are known to those of skill in the art and they may be ones discussed in the Examples. In some embodiments, expression is measured by assaying for RNA, while in others expression is measured by assaying for protein. It is contemplated that PGC-1α RNA or protein may be assayed directly. In addition, in some embodiments, PGC-1α expression is assessed by measuring expression of a reporter gene operably connected to a promoter sequence from PGC-1α or a PGC-1α target gene. It is contemplated that cells used in this screening method may be, but are not limited to, myocytes, osteoblasts, neuroblasts, myoblasts, or muscle cells.

Furthermore, the invention provides a method of treating or preventing muscle loss or wasting in a subject comprising administering to the subject an effective amount of a PGC-1α upregaulator or a Notch inhibitor, wherein an muscle loss or wasting is treated or prevented.

Any embodiment discussed with respect to one aspect of the invention applies to other aspects of the invention as well. The embodiments in the Examples section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Schematic diagram showing the probable gain-of-function of CUG RNA in DM muscle defects. Short to moderate CUG RNA can form a hairpin structure; sequester MBNLs and cause muscle myotonia and milder DM syndrome. Long interrupted CUG RNA can adopt more complex secondary and high conformation structure in vivo, which can sequester additional RNA binding proteins and thus can establish complex structural and functional abnormalities in skeletal muscle. The CCUG can adopt hairpin and other distinct RNA structure and sequester different sets of proteins; muscle-blind being the common ones.

FIGS. 2A-B. The identification of long CUG RNA binding protein, skeletrophin from mouse muscle extract. FIG. 2A shows the domain structure of human skeletrophin. Human skeletrophin contains two mib/herc2 domains; one Zinc finger ZZ type domain that present in dystrophin, one CBP/ p300; five ankyrin repeats that mediate protein-protein interactions in very diverse families of proteins and one C-terminal RING-finger domain, a specialized type of Zn-finger of 40 to 60 residues that binds two atoms of zinc and probably involved in mediating protein-protein interactions. FIG. 2B shows the areas of significant similarity (>80% homolog) of skeletrophin between human and mouse.

FIGS. 3A-B. The schematic diagram showing the essential features of the transgenic constructs being used for this study. (FIGS. 3A and 3B) The human α-actin promoter (approximately 2.2 kb) is cloned upstream of the β-galactosidase gene. The CTG and CCTG duplexes are cloned at the SwaI site located downstream of the β-galactosidase and upstream of the BGH poly-A sequences such that CTG and CCTG sequences are transcribed into RNA but not translated into protein. After an SfiI restriction digest of the transgenic plasmids encoding greater than 3 kb of CTG (lane 1) and CCTG sequences an agarose gel showed the presence of approximately 5 kb of CTG and CCTG repeats marked with arrows. A Southern blot of the tail-clip DNA isolated from the founder animals confirmed the presence of the approximately 12 kb transgene.

FIGS. 4A1-4A3. Figure showing the different transgenic constructs to determine the functional significance of sequence-interruptions within CTG sequences: (FIG. 4A1) Schematic diagram of the transgenic construct wherein 3.2 kb SacI-XhoI fragment that encompass the human DMPK exon 15 and part of SIX5 exon 1 was cloned downstream of the human α-actin promoter and upstream of BGH-polyA sequences. Uninterrupted synthetic CTG duplexes were cloned into the BsmI site that lie in the CTG expansion locus. (FIG. 4A2) Schematic diagram showing the transgene wherein the expanded CTG repeats (approximately 1200 CTG repeats) from the DM1 patients DNA was first PCR amplified and then cloned into the same locus. (FIG. 4A3) Schematic diagram of the transgenic constructs wherein the PCR amplified DM1 locus encoding 1200 interrupted CTG were cloned into the 3' UTR of β-galactosidase gene.

FIG. 5. Figure showing expression of skeletrophin in bacteria. Panel A: Shows the schematic diagram of the plasmid wherein the skeletrophin cDNA was cloned into pET22b protein expression vector.

FIGS. 6A-B. Expression of Skeletrophin in different embryonic days and adult tissue. (FIG. 6A) The expression of mouse skeletrophin transcripts in developmental stages in mouse was examined by Northern blot analysis as shown in the upper panel. The relative loading and integrity of total RNA on each lane were shown in the lower panel. (FIG. 6B) Mouse mRNA tissue distribution of skeletrophin. A Northern blot of mRNA isolated from mouse tissues was probed with cDNA containing the coding region of mouse skeletrophin.

FIGS. 7A-G. Strategies to develop mice encoding either a targeted deletion of skeletrophin or an inducible deletion of skeletrophin in skeletal muscle: (FIG. 7A) Schematic diagram showing mouse skeletrophin genomic sequences. (FIG. 7B) Schematic diagram of the skeletrophin targeting vector. The Pgk-neo represents a cassette in which the neomycin resistance gene is under the control of the phosphoglycerate kinase promoter. The Pgk-HSV-TK represents a cassette in which the Herpes simplex virus thymidine kinase gene (HSV-TK) is under the transcriptional control of the phosphoglycerate kinase promoter. HSV-TK allows selection against cells that take up DNA by random integration. The 5' and 3' genomic DNA arms, which facilitate the homologous recombination are shown in red. (FIG. 7C) Recombination between the targeting vector with the genomic sequences will result in the deletion of skeletrophin exon 3 to 10. (FIGS. 7D-G) The strategy for inducible deletion of skeletrophin in muscle. (FIG. 7D) The schematic diagram of the targeting vector which will be used for inducible deletion of the skeletrophin. One additional lox sequence will be introduced between exon 2 and 3. The lox sites are shown in red boxes. (FIG. 7E) Recombination between the inducible targeting vector and the genomic sequences will result in the targeted allele as shown. ES cells in which lox sites flank skeletrophin exon 3 and 4 will be used to generate floxed skeletrophin mouse strain as shown in figure. (FIG. 7F) Expression of the Cre recombinase under the control of α-actin promoter will result in the deletion of the exon 3 and 4 of skeletrophin specifically in skeletal muscle resulting in skeletrophin deleted allele (FIG. 7G).

FIG. 8. The schematic diagram showing the essential features of the transgenic constructs being used for this study: The human prion (PrP) promoter (~3.5 kb) is cloned upstream of the β-galactosidase gene. The CTG duplexes are cloned downstream of the β-galactosidase and upstream of the BGH poly-A sequences.

FIG. 9. Downregulation of skeletrophin in C2C12 inhibit muscle differentiation: Expression of long CUG RNA or inactivation of skeletrophin in C2C12 cells causes increase in Notch receptor Jagged2. C2C12 cells were transiently transfected with either vector control (lane 1), short CTG repeats (CTG20) (lane 2), long CTG repeats (CTG1500) (lane 3), or skeletrophin Si-RNA (lane 4).

FIGS. 10A-D. Notch-activity is hyper activated in DM1 cells: (FIG. 10A) Skeletrophin levels are unaltered in normal and DM1 fibroblasts. (FIG. 10B) Sequestration of skeletrophin by expanded CUG RNA results in significant increases of Jagged2 in DM1 fibroblasts. (FIG. 10C) Increased amount of Notch 1 receptor in DM1 fibroblasts reflects hyper-activation of Notch signaling. Lane 1: Normal fibroblasts GM03377; lane 2: Normal fibroblasts GM08402; Lane 3: DM1 fibroblasts GM03132; Lane 4: DM1 fibroblasts GM03759. (FIG. 10D) CBF1-dependent Notch-activity is up-regulated in DM1 fibroblasts. Normal and DM1 fibroblasts were transiently transfected with Notch signaling reporter vectors containing either 8 CBF1 (8×wtCBF1Luc) or mutant CBF1 (8×mtCBF1Luc)-binding sites.

FIGS. 11A-C. The expression of Jagged2 is downregulated in C2C12 cells when co-cultured with DM1 fibroblast. (FIG. 11A) This shows that Jagged2 level is decreased in normal fibroblasts co-cultured with C2C12 cells compare to DM1 fibroblasts co-culturing. (FIG. 11B) Increased expression of muscle differentiation marker myogenein in fibroblasts co-cultured C2C12 cells. C. Downregulation of Notch 1 receptor in normal fibroblasts co-cultured with C2C12 cells compared to DM1 fibroblasts co-culturing. Samples 1. C2C12 co-cultured with DM1 fibroblasts—6 days diff. 2. C2C12 co-culture with normal fibroblasts—6 days diff. (FIG. 11C) CBF1-dependent Notch signaling is up-regulated in DM1 fibroblasts co-cultured with C2C12 cells compare to normal fibroblasts co-culturing. Normal (#2) and DM1 fibroblasts (#1) were co-cultured with C2C12 cells and transiently transfected with Notch signaling reporter vectors containing eight CBF1 (8×wtCBF1Luc)-binding sites.

FIG. 12. Figure showing the up-regulation of both Jagged2 and Notch activity upon Si-RNA-mediated down-regulation of skeletrophin in human normal fibroblasts.

FIG. 13. Development of skeletrophin knockout and conditional knockout vectors: Figure showing the schematic diagram of the conventional targeting vector (top) and the conditional knockout vector (bottom). For conventional knockout vectors, a 3.9 kb of the skeletrophin genomic DNA sequence was cloned (as the 5' region of homology) into the pPNTlox targeting vector and then 4 kb fragment spanning exon 11-19 (3' region of homology) was cloned into the targeting vector to obtain final targeting vector pKO-Stro. For the development of conditional knockout vector, a 4.6 kb genomic region from skeletrophin genomic clone spanning from the second intron to exon 4 (5' region of homology) was cloned into the targeting vector pPNTlox. One LoxP site was introduced into the BamHI site located in the second intron in proper orientation. The 3.3 kb genomic region spanning exon 3-10 (3' region of homology) was cloned at the BamHI/KpnI site of the targeting vector in proper orientation to obtain the final conditional targeting vector pcKO-Stro.

DESCRIPTION OF ILLUSTRATIVE EMBODIMENTS

Figure 14:
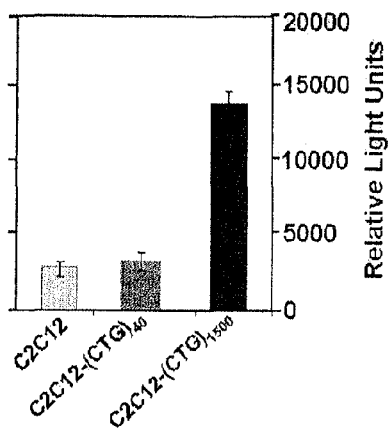
FIG. 14. Expanded CUG RNA upregulates Notch activity in C2C12 cells: Bar diagram showing RBP-Jκ-dependent Notch signaling is ~2 to 3-fold higher in C2C12 cells expressing longer (CUG)n (black bar) compared to control C2C12 cells (white bar) and C2C12 cells that express shorter repeats (grey bar). (n=5 for each measurement and each construct).

There are numerous conditions, disorders, and diseases associated with or characterized by nucleic acids with repeat sequences. The present invention provides methods and compositions for identifying compounds that may be used to prevent or treat these medical problems, in addition to compositions and methods for preventing and treating them.

I. Conditions, Diseases and Disorders Involving Repeats in Nucleotide Sequences Since 1991, a number of genetic disorders have been identified to be caused by the inter- or intragenic presence of long stretches of nucleotide repeats. Although the number of these repeats in the normal population is typically polymorphic, the presence of an excessive number can disrupt gene expression or cause dominant, gain-of-function, mutations leading to the genetic disorder.

Many of these nucleotide repeat disorders were also initially characterized by a phenomenon termed anticipation—the increasing severity of the disease in successive generations coupled with earlier onset. In many of the disorders studied an increasing number of repeats in an individual correlates with increasing severity or earlier onset, suggesting that proliferation or expansion of the repeat in successive generations causes the anticipation phenomenon.

While most of the identified nucleotide repeat disorders occur as trinucleotides, repeats of four, five, or even 33 nucleotides have also been identified.

The present invention concerns any conditions, diseases and disorders involving a nucleotide repeat sequence. In specific embodiments, it concerns DM1, while in others it concerns DM2. DM1 has been discussed above. DM2 patients have relatively milder phenotypes compared to DM1 and the progression of disease phenotypes is slower in DM2 (Harper, 2001; Machuca-Tzili et al., 2005; Liguori et al., 2001). There have been no reports of gastrointestinal tract involvement or congenital defects in DM2, which are common in DM1. The cardiac, CNS and ocular involvement in DM2 are milder than that of DM1, but arrhythmias are frequently detected in DM2 (Day and Ranum, 2005; Ranum and Day, 2004). In DM2, some endocrine abnormalities, such as testicular dysfunctions and insulin resistance are common but milder than DM1. Frontal executive dysfunctions are reported, but the social and cognitive abilities are typically mild and hypersomnolence and mental retardation are not prominent phenotypes in DM2. The presence of severe muscle and joint pain and calf muscle hypertrophy in DM1 further differentiate DM2 from DM1 (Harper, 2001; Machuca-Tzili et al., 2005; Day and Ranum, 2005; Ranum and Day, 2004).

The expanded CCTG tetranucleotide repeat in the first intron of the ZNF9 gene in DM2 is transcribed into a CCUG repeat, but the expanded CCUG repeats are not translated into protein (Liguori et al., 2001). The normal function of the ZNF9 protein is unknown although it is known to be capable of binding both DNA and RNA. Mice completely deficient for Znf9 is embryonic lethal with gross disruption of forebrain development. Around 40% of heterozygous Znf9 deficient mice are also born with abnormal forebrain development and craniofacial abnormalities, and die within a few hours of birth while the remaining 60% develop normally into adulthood or with mild eye and skeletal defects and these effects are obviously not related to the classic myotonic dystrophy phenotype. Therefore, haploinsufficiency of ZNF9 in pathogenic role in DM2 is most unlikely (Chen et al., 2003). In addition to similarities in clinical phenotypes, significant similarities between DM1 and DM2 have also been demonstrated in the molecular mechanism of the disease at the RNA level (Ranum and Day, 2002). The muscle-blind proteins accumulate in the nuclear foci where RNA with CCUG repeats are deposited (Mankodi et al., 2003a; Fardaei et al., 2002; Mankodi et al., 2003b), and CLC-1 and IR mis-splicing is also observed in DM2 patients (Mankodi et al., 2002; Savkur et al., 2004).

A. Trinucleotide Repeat Disorders

Nucleotide repeat expansion was first identified as a cause of a human genetic disorders in two disorders: fragile X syndrome and spino-bulbar muscular atrophy (SBMA). Fragile X syndrome is one of the most common forms of inherited mental retardation. Most cases of fragile X syndrome are caused by expansion of a CGG repeat in the 5' untranslated region of the fragile X mental retardation 1 gene (FMR1). The expansion to more than 500 repeats results in the transcriptional silencing of the FMR1 gene and loss of the FMR1 protein product. (Gatchel and Zoghbi).

In contrast to the transcriptional silencing seen in fragile x syndrome, repeats may also be located in the coding regions of genes and cause abnormality when the protein including the repeats is expressed. Spino-bulbar muscular atrophy (SBMA) is caused by expansion of a trinucleotide, CAG, in the coding region of an androgen receptor gene. (La Spada et al.). Individuals with SBMA typically have 40 or more CAG repeats, and presence of the repeats appears to cause a gain-of-function mutation in the expressed androgen receptor.

Like SBMA, Huntington disease is caused by expansion of a CAG-triplet repeat in an exon of the HD gene. (MacDonald et al.). The CAG repeat is translated into a stretch of polyglutamine residues which, when there are too many repeats, can self associate leading to an aggregation of huntingtin protein. The presence of more than 40 CAG repeats will cause Huntington disease within a normal lifespan, and greater numbers of repeats cause earlier onset.

Myotonic dystrophy is the most common form of muscular dystrophy in adults and can be caused by two different mutations, both involving nucleotide repeat expansion. In type-1 myotonic dystrophy (DM1) the expanded CTG repeat is located in both the 3' untranslated region of the dystrophia myotonic-protein kinase gene (DMPK) and the promoter region of an adjacent homeodomain gene, SIX5. The varied symptoms of DM may be caused additively by the effect of the repeat on expression of both genes, as well as the nuclear accumulation of RNA transcript containing the CTG repeat. (Tapscott).

Other types of trinucleotide repeat disorders include: Fragile X syndrome, E-subtype (CCG); Jacobsen syndrome (CGG); Spinocerebellar ataxia (SCA) type 1 (CAG); SCA 2 (CAG); Machado-Joseph disease (CAG); SCA6 (CAG), SCAT (CAG), SCA 8 (CTG); SCA 12 (CAG); dentatorubral pallidoluysian atrophy (CAG); Friedreich ataxia (AAG); Huntington disease-like 2 (CTG); oculopharyngeal muscular dystrophy (GCG); multiple epiphyseal dysplasia (GAC); cleidocraial dysplasia (GCN); and synpolydactyly (GCN).

B. Other Nucleotide Repeat Disorders

Although trinucleotide repeats disorders are the most frequently identified, repeats of other lengths may also lead to disease.

Type-2 myotonic dystrophy (DM2), an autosomal dominant disorder, is caused by expansion of a tetranucleotide, CCTG, in an intron of a zinc-finger protein, ZNF9. The largest number of repeats found in individuals with DM2 is over 11,000, while in normal individuals there were typically fewer than 30 repeats. (Liguori et al.). Although ZFN9 is thought to be an RNA-binding protein, the protein does not seem to be directly implicated in DM2. Instead, expressed ZFN9 mRNA, containing the tetranucleotide repeat expansion, accumulates in the nucleus, where it may contribute to disruptions in RNA splicing and cellular metabolism (Liguori et al.).

Spinocerebellar ataxia type 10 (SCA10) is an autosomal dominant disorder characterized by cerebellar ataxia and seizures. Expansion of a pentanucleotide repeat in an intron of the SCA10 gene, in some cases up to 22.5 kb, causes the disorder. (Matsuura et al.).

Expansion of a dodecamer (12-mer) repeat was identified to cause the autosomal recessive neurodegenerative disease progressive myclonus epilepsy (EPM1). (Lalioti et al.). The repeat is located about 70 nucleotides upstream of the transcription start site of the cysteine proteinase inhibitor gene, cystatin B (CSTB). While normal alleles of the gene contain 2 or 3 copies of the repeat, mutant alleles contain more than 60 such repeats. (Lalioti et al.). Expansion of the repeat, although outside of the transcriptional unit, appears to reduce the expression of the CSTB gene. (Lalioti et al.).

Expansion of 33-mer repeat has also been identified as the basis of a non-folate sensitive fragile site, FRA16B. (Yu et al.).

II. Nucleic Acids

The present invention concerns a number of different types of nucleic acid molecules that can be used in a variety of ways. In some embodiments of the invention the nucleic acid is a recombinant nucleic acid. The term "recombinant" is used according to its ordinary and plain meaning to refer to the product of recombinant DNA technology, i.e., genetically engineered DNA prepared in vitro by cutting up DNA molecules and splicing together specific DNA fragments, which may or may not be from different organisms. Things that have or are from a genetically engineered DNA are similarly recombinant; this includes replicated or duplicated products based on the initially engineered DNA. In particular embodiments, the nucleic acid is an RNA transcript with nucleotide repeats, such as a CUG or CAG trinucleotide repeat. The number of repeats may be indicative or related to a mutant transcript that has physiological effects.

In other embodiments, the nucleic acid molecule is a DNA molecule, for example, a DNA molecule whose expression gives rise to the RNA transcript. Alternatively, the DNA molecule may be used in a screening method or therapeutic method of the invention or the molecule may encode an RNA transcript or polypeptide that is used in such methods. These different DNA molecules may or may not be in an expression construct such as a vector or in a host cell. Further details are provided below.

The present invention concerns polynucleotides, isolatable from cells, that are free from total genomic DNA and that are capable of expressing all or part of an RNA molecule, RNA transcript, protein or polypeptide. The polynucleotide may be an RNA molecule or transcript with multiple nucleotide repeats and/or encode a peptide or polypeptide containing all or part of an amino acid sequence with repeated amino acids. Alternatively, a polynucleotide may encode a peptide or polypeptide having all or part of the amino acid sequence of a modulator of a nucleic acid or protein associated with a repeat sequence.

Embodiments of the invention concern isolated and/or recombinant polynucleotides. An isolated polynucleotide refers to a polynucleotide that is separated from a cell and its non-nucleic acid contents, and more specifically, may be separated from other nucleic acid sequences. A recombinant polynucleotide refers to a genetically engineered nucleic acid molecule or products of such a molecule (either through duplication, replication, or expression).

In certain embodiments, the polynucleotide is a nucleic acid having nucleotide repeats sequences. Such polynucleotides may be wild-type, mutant, or polymorphic. In the context of diseases and conditions that are characterized and/ or caused by repeat sequences in the subject's genome, "mutant" refers to a sequence associated with the disease or condition or symptoms of the disease or condition. Included within the term "nucleic acid" are a polynucleotide, segments smaller than a polynucleotide (oligonucleotide), and recombinant vectors, including, for example, plasmids, cosmids, phage, viruses, and the like. Embodiments of the invention concern a nucleic acid that is recombinant in embodiments of the invention. In other embodiments, the nucleic acid is isolated and/or purified.

As used in this application, the term "transcript" refers to an ribonucleic acid molecule (RNA) that in some embodiments of the invention is generated from a recombinant DNA molecule. In particular embodiments, polynucleotides of the invention concern a DMPK transcript, which may or may not be mutant (mutant is characterized by more than 40 repeats).

The term "cDNA" is intended to refer to DNA prepared using messenger RNA (mRNA) as template. In many embodiments of the invention the nucleic acid is a cDNA or cDNA sequence. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a particular RNA molecule or transcript from a given species may be represented by natural variants that have slightly different nucleic acid sequences but, nonetheless, encode what is considered a wild-type sequence. DMPK has a trinucleotide repeat region that is characterized by a variable number of repeats. 40 repeats or fewer is generally understood to be associated with a wild-type phenotype; consequently, a nucleic acid with 40 or fewer repeats will be considered a wild-type sequence with respect to the trinucleotide repeat region.

A nucleic acid encoding all or part of a wild-type or mutant transcript or polypeptide may contain a contiguous nucleic acid sequence encoding all or a portion of such a transcript or polypeptide of the following lengths: about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more residues. This pertains to any gene, transcript, peptide or polypeptide sequence discussed herein, including any GenBank accession numbers or SEQ ID NOs.

It is contemplated that nucleic acid molecules encoding RNA molecules with a nucleotide repeat region may be used in method and compositions of the invention. Furthermore, candidate substances or compounds, candidate therapeutic agents, or other agents may be employed as nucleic acids, including recombinant nucleic acids in compositions and methods of the invention.

In other embodiments, the invention concerns isolated nucleic acid molecules and recombinant vectors incorporating DNA sequences that encode a polypeptide or peptide that includes within its amino acid sequence a contiguous amino acid sequence in accordance with, or essentially corresponding to the polypeptide.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

It is contemplated that the nucleic acid constructs of the present invention may encode part or all (full-length) of transcripts or polypeptides from any source. Alternatively, a nucleic acid sequence may encode an RNA or polypeptide with additional heterologous sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a sequence that is not the same from the same source as other sequences.

In a non-limiting example, one or more nucleic acid constructs may be prepared that include a contiguous stretch of nucleotides identical to or complementary to the a particular nucleic acid sequence, such as the human DMPK gene (SEQ ID NO:1—or other wild-type variations thereof—or mutant version thereof, such as SEQ ID NO:2). A nucleic acid construct may be at least 20, 30, 40, 50, 60, 70, 80, 90, 100, 110, 120, 130, 140, 150, 160, 170, 180, 190, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 50,000, 100,000, 250,000, 500,000, 750,000, to at least 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values).

In certain other embodiments, the invention concerns isolated DNA segments and recombinant vectors that include within their sequence a contiguous nucleic acid sequence from those shown in SEQ ID NO:1 (or other wild-type variations, or mutants variations thereof, such as SEQ ID NO:2), or SEQ ID NO:3. This definition is used in the same sense as described above and means that the nucleic acid sequence substantially corresponds to a contiguous portion of that shown in SEQ ID NO:1 (or other wild-type variations, or mutants thereof, such as SEQ ID NO:2), or SEQ ID NO:3 and has relatively few codons that are not identical, or functionally equivalent, to the codons of SEQ ID NO:1 (or other wild-type variations, or mutants thereof, such as SEQ ID NO:2), or SEQ ID NO:3, respectively. The term "functionally equivalent codon" is used herein to refer to codons that encode the same amino acid, such as the six codons for arginine or serine, and also refers to codons that encode biologically equivalent amino acids. See Table 1 below, which lists the codons preferred for use in humans, with the codons listed in decreasing order of preference from left to right in the table (Wada et al., 1990). Codon preferences for other organisms also are well known to those of skill in the art (Wada et al., 1990, included herein in its entirety by reference).

TABLE 1

Preferred Human DNA Codons

| Amino Acids | | | Codons |
|---|---|---|---|
| Alanine | Ala | A | GCC GCT GCA GCG |
| Cysteine | Cys | C | TGC TGT |
| Aspartic acid | Asp | D | GAC GAT |
| Glutamic acid | Glu | E | GAG GAA |
| Phenylalanine | Phe | F | TTC TTT |
| Glycine | Gly | G | GGC GGG GGA GGT |
| Histidine | His | H | CAC CAT |
| Isoleucine | Ile | I | ATC ATT ATA |
| Lysine | Lys | K | AAG AAA |
| Leucine | Leu | L | CTG CTC TTG CTT CTA TTA |

TABLE 1-continued

Preferred Human DNA Codons

| Amino Acids | | | Codons |
|---|---|---|---|
| Methionine | Met | M | ATG |
| Asparagine | Asn | N | AAC AAT |
| Proline | Pro | P | CCC CCT CCA CCG |
| Glutamine | Gln | Q | CAG CAA |
| Arginine | Arg | R | CGC AGG CGG AGA CGA CGT |
| Serine | Ser | S | AGC TCC TCT AGT TCA TCG |
| Threonine | Thr | T | ACC ACA ACT ACG |
| Valine | Val | V | GTG GTC GTT GTA |
| Tryptophan | Trp | W | TGG |
| Tyrosine | Tyr | Y | TAC TAT |

It also will be understood that this invention is not limited to the particular nucleic acid and amino acid sequences of SEQ ID NO:1 (or mutant thereof, such as SEQ ID NO:2), SEQ ID NO:3, SEQ ID NO:4, or SEQ ID NO:5.

The DNA segments of the present invention encompass biologically functional equivalent DMPK transcripts. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein.

A number of additional embodiments in the context of nucleic acids are discussed below.

A. Vectors

RNA molecules, peptides and polypeptides may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., (1989) and Ausubel et al., 1996, both incorporated herein by reference. A targeting molecule is one that directs the modified polypeptide to a particular organ, tissue, cell, or other location in a subject's body.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of RNA molecules used in methods of the invention. Expression vectors can contain a variety of "control sequences," which refer to nucleic acid sequences necessary for the transcription and possibly translation of an operably linked coding sequence in a particular host organism. For instance, in some embodiments of the invention, there may sequences to allow for in vitro transcription of a sequence. In particular embodiments, the expression vector may contain an Sp6, T3, or T7 promoter. In addition to control sequences that govern transcription and translation, vectors and expression vectors may contain nucleic acid sequences that serve other functions as well and are described infra.

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

In certain embodiments of the invention, a vector may also include one or more of: an ATG initiation signal, internal ribosome binding sites, multiple cloning site (MCS), splicing site, termination signal, polyadenylation signal, origin of replication, or selectable or screenable marker (drug resistance marker, enzymatic marker, colorimetric marker, fluorescent marker).

In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

Viral vectors that may be used include, but are not limited to, adenovirus, adeno-associated virus, lentivirus, retrovirus, herpesvirus, papilloma virus, vaccinia virus, or hepatitis virus.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. Such a host cell would be considered recombinant if the heterologous nucleic acid sequence was the product of recombinant DNA technology. A host cell can, and has been, used as a recipient for vectors. A host cell may be "transfected" or "transformed," which refers to a process by which exogenous nucleic acid, such as a modified protein-encoding sequence, is transferred or introduced into the host cell. A transformed cell includes the primary subject cell and its progeny.

Host cells may be derived from prokaryotes such as bacteria or eukaryotes, including yeast cells, insect cells, and mammalian cells, depending upon whether the desired result is replication of the vector or expression of part or all of the vector-encoded nucleic acid sequences. In certain embodiments, the cell is an embryonic stem cell, such as from a mouse.

Numerous cell lines and cultures are available for use as a host cell, and they can be obtained through the American Type Culture Collection (ATCC), which is an organization that serves as an archive for living cultures and genetic materials (World Wide Web at atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include but are not limited to XL-10-Gold and SURE 2 (Stratagene), which have been employed in the Examples. Additional bacterial cells are DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

D. Introduction of Nucleic Acids

DNA constructs of the present invention are generally delivered to a cell, in certain situations, the nucleic acid to be transferred is non-infectious, and can be transferred using non-viral methods. Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

E. Antisense Molecules, Ribozymes, and siRNA

In some embodiments of the invention, agents or compounds are nucleic acid molecules with complementarity to target molecules. Such nucleic acids include antisense molecules, ribozymes, and siRNAs that are targeted to particular sequences based on the desired goal. In certain embodiments, for instance, a Notch may be inhibited or inactivated using an siRNA that targets a component of the Notch activation pathway, such as γ-secretase. Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs may include regions complementary to intron/exon splice junctions. Thus, antisense constructs with complementarity to regions within 50-200 bases of an intron-exon splice junction may be used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

The use of ribozymes is claimed in the present application. The following information is provided in order to compliment the earlier section and to assist those of skill in the art in this endeavor.

Ribozymes are RNA-protein complexes that cleave nucleic acids in a site-specific fashion. Ribozymes have specific catalytic domains that possess endonuclease activity (Kim and Cech, 1987; Gerlack et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990; Sioud et al., 1992). Recently, it was reported that ribozymes elicited genetic changes in some cell lines to which they were applied; the altered genes included the oncogenes H-ras, c-fos and genes of HIV. Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Several different ribozyme motifs have been described with RNA cleavage activity (reviewed in Symons, 1992). Examples that would be expected to function equivalently for the down regulation of AR include sequences from the Group I self splicing introns including tobacco ringspot virus (Prody et al., 1986), avocado sunblotch viroid (Palukaitis et al., 1979 and Symons, 1981), and Lucerne transient streak virus (Forster and Symons, 1987). Sequences from these and related viruses are referred to as hammerhead ribozymes based on a predicted folded secondary structure.

Other suitable ribozymes include sequences from RNase P with RNA cleavage activity (Yuan et al., 1992, Yuan and Altman, 1994), hairpin ribozyme structures (Berzal-Herranz et al., 1992; Chowrira et al., 1993) and hepatitis δ virus based ribozymes (Perrotta and Been, 1992). The general design and optimization of ribozyme directed RNA cleavage activity has been discussed in detail (Haseloff and Gerlach, 1988, Symons, 1992, Chowrira, et al., 1994, and Thompson, et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A, C or U; Perriman, et al., 1992; Thompson, et al., 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. The identification of operative and preferred sequences for use in targeted ribozymes is simply a matter of preparing and testing a given sequence, and is a routinely practiced "screening" method known to those of skill in the art.

An RNA molecule capable of mediating RNA interference in a cell is referred to as "siRNA." Elbashir et al. (2001) discovered a clever method to bypass the anti viral response and induce gene specific silencing in mammalian cells. Several 21-nucleotide dsRNAs with 2 nucleotide 3' overhangs were transfected into mammalian cells without inducing the antiviral response. The small dsRNA molecules (also referred to as "siRNA") were capable of inducing the specific suppression of target genes.

In the context of the present invention, siRNA directed against γ-secretase, Jagged2, the Notch ligand, HES, HERP, and mutant DMPK transcripts are specifically contemplated. The siRNA can target a particular sequence because of a region of complementarity between the siRNA and the RNA transcript encoding the polypeptide whose expression will be decreased, inhibited, or eliminated.

An siRNA may be a double-stranded compound comprising two separate, but complementary strands of RNA or it may be a single RNA strand that has a region that self-hybridizes such that there is a double-stranded intramolecular region of 7 basepairs or longer (see Sui et al., 2002 and Brummelkamp et al., 2002 in which a single strand with a hairpin loop is used as a dsRNA for RNAi). In some cases, a double-stranded RNA molecule may be processed in the cell into different and separate siRNA molecules.

In some embodiments, the strand or strands of dsRNA are 100 bases (or basepairs) or less, in which case they may also be referred to as "siRNA." In specific embodiments the strand or strands of the dsRNA are less than 70 bases in length. With respect to those embodiments, the dsRNA strand or strands may be from 5-70, 10-65, 20-60, 30-55, 40-50 bases or basepairs in length. A dsRNA that has a complementarity region equal to or less than 30 basepairs (such as a single stranded hairpin RNA in which the stem or complementary portion is less than or equal to 30 basepairs) or one in which the strands are 30 bases or fewer in length is specifically contemplated, as such molecules evade a mammalian's cell antiviral response. Thus, a hairpin dsRNA (one strand) may be 70 or fewer bases in length with a complementary region of 30 basepairs or fewer.

Methods of using siRNA to achieve gene silencing are discussed in WO 03/012052, which is specifically incorporated by reference herein. Designing and testing siRNA for efficient inhibition of expression of a target polypeptide is a process well known to those skilled in the art. Their use has become well known to those of skill in the art. The techniques described in U.S. Patent Publication No. 20030059944 and 20030105051 are incorporated herein by reference. Furthermore, a number of kits are commercially available for generating siRNA molecules to a particular target, which in this case includes AR, NF-κB, and TNF-α. Kits such as Silencer™ Express, Silencer™ siRNA Cocktail, Silencer™ siRNA Construction, MEGAScript® RNAi are readily available from Ambion, Inc.

F. Nucleic Acid Detection

In some embodiments, detection of a nucleic acid is involved in methods of the invention. For instance, in screening methods inhibition or disruption of an association between an RNA molecule with a nucleotide repeat region and a skeletrophin polypeptide may involve nucleic acid detection techniques. Such methodology may include using a probe contacted with the RNA molecule under hybridization conditions (e.g., stringent conditions: relatively low salt and/or high temperature conditions, such as provided by about 0.02 M to about 0.10 M NaCl at temperatures of about 50° C. to about 70° C.; a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C.). Hybridization conditions can be readily manipulated depending on the desired results. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

Other methods may involve, for instance, primer(s) in amplification techniques. Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641.

Polymerase chain reaction methodologies are well known in the art. Representative methods of RT-PCR are described in U.S. Pat. No. 5,882,864.

Alternative methods for amplification of target nucleic acid sequences that may be used in the practice of the present invention are disclosed in U.S. Pat. Nos. 4,883,750, 5,843,650, 5,846,709, 5,846,783, 5,849,546, 5,849,497, 5,849,547, 5,858,652, 5,866,366, 5,912,148, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

G. Transgenic Animals

It is contemplated that transgenic animals are part of the present invention. A transgenic animal of the present invention may involve an animal having a transgene that expresses an RNA molecule with a wild-type or mutant nucleotide repeat region, such as an extensive nucleotide repeat region. It is also contemplated that the transgene may be expressed in a different tissue type or in a different amount or at a different time than the endogenously expressed version of the transgene.

In a general aspect, a transgenic animal is produced by the integration of a given transgene into the genome in a manner that permits the expression of the transgene, or by disrupting the wild-type gene, leading to a knockout of the wild-type gene. Methods for producing transgenic animals are generally described by Wagner and Hoppe (U.S. Pat. No. 4,873,191; which is incorporated herein by reference), Brinster et al. (1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

U.S. Pat. No. 5,639,457 is also incorporated herein by reference to supplement the present teaching regarding transgenic pig and rabbit production. U.S. Pat. Nos. 5,175,384; 5,175,385; 5,530,179, 5,625,125, 5,612,486 and 5,565,186 are also each incorporated herein by reference to similarly supplement the present teaching regarding transgenic mouse and rat production. Transgenic animals may be crossed with other transgenic animals or knockout animals to evaluate phenotype based on compound alterations in the genome.

III. Proteinaceous Compositions

In certain embodiments, the present invention concerns compositions comprising at least one proteinaceous molecule, such as skeletrophin peptide or polypeptide, such as an antibody against a Notch activator. As used herein, a "proteinaceous molecule," "proteinaceous composition," "proteinaceous compound," "proteinaceous chain" or "proteinaceous material" generally refers, but is not limited to, a protein molecule containing at least one polypeptide with multiple amino acids. The protein may contain more than one polypeptide, such as a dimer or trimer or other tertiary structure. In some embodiments, a protein refers to a polypeptide that has 3 amino acids or more or to a peptide of from 3 to 100 amino acids. All the "proteinaceous" terms described above may be used interchangeably herein. In the case of a protein composed of a single polypeptide, the terms "polypeptide" and "protein" are used interchangeably.

In certain embodiments the size of the at least one proteinaceous molecule may comprise, or be at most or at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600 or greater amino molecule residues, and any range derivable therein. Moreover, it may contain such lengths of contiguous amino acids from a polypeptide provided herein, such as a human skeletrophin polypeptide sequence.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to those shown on Table 2 below.

TABLE 2

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |

TABLE 2-continued

Modified and Unusual Amino Acids

| Abbr. | Amino Acid | Abbr. | Amino Acid |
|---|---|---|---|
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In certain embodiments the proteinaceous composition comprises at least one protein, polypeptide or peptide. In further embodiments the proteinaceous composition comprises a biocompatible protein, polypeptide or peptide. As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (on the World Wide Web at ncbi.nlm.nih.gov/). The coding regions for these known genes may be amplified and/or expressed using the techniques disclosed herein or as would be know to those of ordinary skill in the art. Alternatively, various commercial preparations of proteins, polypeptides and peptides are known to those of skill in the art.

In certain embodiments a proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

In certain embodiments, the proteinaceous composition may comprise at least one antibody, for example, an antibody against skeletrophin, which may be used to determine whether it is sequestered. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Harlow et al., 1988; incorporated herein by reference).

It is contemplated that virtually any protein, polypeptide or peptide containing component may be used in the compositions and methods disclosed herein. However, it is preferred that the proteinaceous material is biocompatible. In certain embodiments, it is envisioned that the formation of a more viscous composition will be advantageous in that will allow the composition to be more precisely or easily applied to the tissue and to be maintained in contact with the tissue throughout the procedure. In such cases, the use of a peptide composition, or more preferably, a polypeptide or protein composition, is contemplated. Ranges of viscosity include, but are not limited to, about 40 to about 100 poise. In certain aspects, a viscosity of about 80 to about 100 poise is preferred.

In certain embodiments, a peptide or polypeptide may contain an amino acid sequence that is identical or similar to a reference sequence or a particular region of the reference sequence. In certain embodiments a peptide or polypeptide has at least or most 60, 65, 70, 75, 80, 85, 90, 95, 96, 97, 98, 99, 99.5, 100% identity with respect to the amino acid sequence of a particular polypeptide or within a region of the particular polypeptide. For instance, in some embodiments of the invention, there are peptides derived from skeletrophin. The term "derived from" means that at least 50% of the amino acid sequence of the peptide is identical or similar to skeletrophin across the length of the peptide.

In the case of similar amino acids, certain amino acids can be substituted for one another with minimal effect on protein function. Amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include those in the table below.

TABLE 3

| Original Residue | Exemplary Substitutions |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |
| Tyr | Trp; Phe |
| Val | Ile; Leu |

Accordingly, sequences that have between about 70% and about 80%, between about 81% and about 90%; or between about 91% and about 99%; of amino acids that are identical or functionally equivalent to the amino acids of a reference polypeptide sequence are included as part of the invention.

Another embodiment for the preparation of polypeptides according to the invention is the use of peptide mimetics. Mimetics are peptide-containing molecules that mimic elements of protein secondary structure. See e.g., Johnson (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of the original protein, but with altered and even improved characteristics.

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals or transmembrane regions.

A. Protein Purification

In some embodiments, it may be desirable to purify a protein, for example, skeletrophin (or a derived peptide) or a candidate substance, or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide or polypeptide are filtration, ion-exchange chromatography, exclusion chromatography, polyacrylamide gel electrophoresis, affinity chromatography, or isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

B. Antibodies

Another embodiment of the present invention are antibodies, which can be used in the context of the present invention as a candidate substance or to determine the effect of a candidate substance. In some cases, a human monoclonal antibody immunoreactive with the polypeptide sequence of skeletrophin may be employed to evaluate whether skeletrophin is sequestered by an RNA molecule having a nucleotide repeat region. It is also understood that antibodies can be used for inhibiting or modulating Notch activation. The antibody also may be useful in the screening of expressed DNA segments or peptides and proteins for the discovery of related antigenic sequences. In addition, the antibody may be useful in passive immunotherapy for cancer. All such uses of the said antibody and any antigens or epitopic sequences so discovered fall within the scope of the present invention.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified polypeptide, peptide or domain, be it a wild-type or mutant composition. The immunizing composition is administered in a manner effective to stimulate antibody producing cells.

Antibodies may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, antibody fragments encompassed by the present invention can be synthesized using an automated peptide synthesizer.

It also is contemplated that a molecular cloning approach may be used to generate antibodies.

"Humanized" antibodies are also contemplated, as are chimeric antibodies from mouse, rat, or other species, bearing human constant and/or variable region domains, bispecific antibodies, recombinant and engineered antibodies and fragments thereof. The techniques for producing humanized immunoglobulins are well known to those of skill in the art. For example U.S. Pat. No. 5,693,762 discloses methods for producing, and compositions of, humanized immunoglobulins having one or more complementarity determining regions (CDR's). When combined into an intact antibody, the humanized immunoglobulins are substantially non-immunogenic in humans and retain substantially the same affinity as the donor immunoglobulin to the antigen, such as a protein or other compound containing an epitope. Examples of other teachings in this area include U.S. Pat. Nos. 6,054,297; 5,861,155; and 6,020,192, all specifically incorporated by reference. Methods for the development of antibodies that are "custom-tailored" to the patient's disease are likewise known and such custom-tailored antibodies are also contemplated.

As discussed, in some embodiments, the present invention concerns immunodetection methods for binding, purifying, removing, quantifying and/or otherwise detecting biological components such as antigenic regions on polypeptides and peptides. The immunodetection methods of the present invention can be used to characterize a peptide, polypeptide, or protein that has therapeutic implications.

Immunodetection methods include enzyme linked immunosorbent assay (ELISA), radioimmunoassay (RIA), immunoradiometric assay, fluoroimmunoassay, chemiluminescent assay, bioluminescent assay, and Western blot, though several others are well known to those of ordinary skill. The steps of various useful immunodetection methods have been described in the scientific literature, such as, e.g., Doolittle et al., 1999; Gulbis et al., 1993; De Jager et al., 1993; and Nakamura et al., 1987, each incorporated herein by reference.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277, 437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected. Another known method of immunodetection takes advantage of the immuno-PCR (Polymerase Chain Reaction) methodology.

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections or cells is also particularly useful. However, it will be readily appreciated that detection is not limited to such techniques, and/or western blotting, dot blotting, FACS analyses, and/or the like may also be used.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

The antibodies of the present invention may also be used in conjunction with both fresh-frozen and/or formalin-fixed, paraffin-embedded tissue blocks prepared for study by immunohistochemistry (IHC). For example, immunohistochemistry may be utilized to characterize skeletrophin in a cell. The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

IV. Screening Methods

The present invention comprises methods for screening for candidate therapeutic agents for downregulating Notch, to act as a skeletrophin agent, or to effect a therapeutic effect with respect to a disease or condition characterized by a nucleic acid with nucleotide repeat region, such as DM1. These assays may comprise random screening of large libraries of candidate substances; alternatively, the assays may be used to focus on particular classes of compounds selected with an eye towards structural attributes that are believed to make them more likely to modulate the function of Notch activation or nucleic acids with a nucleotide repeat region.

By function, it is meant, for instance, that one may assay for a measurable effect on Notch activation and/or activity. Alternatively, one may evaluate for an effect on the ability of a nucleic acid with an extensive nucleotide repeat region to bind or sequester another molecule, such as a polypeptide.

To identify such modulator, one generally will determine the activity or level of the relevant nucleic acid or protein in the presence and absence of the candidate substance, wherein a modulator is defined as any substance that alters these characteristics. For example, a method generally comprises:

(a) providing a candidate substance;
(b) admixing the candidate substance with an isolated compound or cell expressing the compound;
(c) measuring one or more characteristics of the compound or cell in step (b); and
(d) comparing the characteristic measured in step (c) with the characteristic of the compound or cell in the absence of the candidate substance,
wherein a difference between the measured characteristics indicates that the candidate modulator is, indeed, a modulator of the compound or cell.

Assays may be conducted in cell free systems, in isolated cells, or in organisms including transgenic animals. Such cells may be recombinant as well.

It will, of course, be understood that all the screening methods of the present invention are useful in themselves notwithstanding the fact that effective candidates may not be found. The invention provides methods for screening for such candidates, not solely methods of finding them.

A. Modulators

As used herein the term "candidate substance" refers to any molecule that may be a "candidate therapeutic agent", i.e., potentially affect Notch activity, directly or indirectly or a nucleic acid with an extensive nucleotide repeat region that is associated with a condition, disease, or disorder. In other embodiments, the candidate substance may be a skeletrophin agent. Such a substance increases the amount of available skeletrophin, which may be the result of direct or indirect action. An example of a substance that works directly is skeletrophin itself or a substance with skeletrophin activity. An example of indirect action is where the skeletrophin agent inhibits the ability of an RNA molecule with an extensive nucleotide repeat region to sequester skeletrophin.

A candidate substance may be a downregulator of Notch, which is a compound that overall effects an inhibition of Notch activity, which may be accomplished by inhibiting Notch activation (for instance, by inhibiting a Notch activator, such as γ-secretase, or by inhibiting Jagged2, the Notch ligand, HES, HERP, and mutant DMPK transcripts), translocation or transport, function, expression, post-translational modification, location, half-life, or more directly by preventing its activity, such as by binding Notch and preventing signal transduction.

A modulator may be a "modulator of a nucleotide repeat region nucleic acid," which inhibits or enhances the function of a nucleic acid with a nucleotide repeat region, by increasing or reducing, for example, its ability to sequester a protein that it binds to or associates with, such as skeletrophin in DM1. The modulator may also affect expression, translocation or transport, function, expression, post-translational modification, location, half-life, or more directly the nucleic acid's activity.

Any modulator described in methods and compositions herein may be an inhibitor or an enhancer.

The candidate substance may be a protein or fragment thereof, a small molecule, or even a nucleic acid molecule. It also is possible to use antibodies either as candidate substances or to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, siRNA, and antibodies (including single chain antibodies), each of which would be specific for the target molecule. Such compounds are well known to those of skill in the art. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

B. In Vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

Another assay may involve cell extracts, such as an electrophoretic mobility shift assay (EMSA), DNase footprinting or other nuclease protection assay, in vitro transcription assay, Western blotting, Southwester blotting, Southern assay, PCR (including real-time PCR and RT-PCR), etc.

A technique for high throughput screening of compounds is described in WO 84/03564. Large numbers of small peptide test compounds are synthesized on a solid substrate, such as plastic pins or some other surface. Bound polypeptide is detected by various methods.

C. Cell Culture Assays

In some embodiments of the invention, assays are conducted using cells, including cells grown in tissue culture. It is contemplated that the cells may be recombinant, such as by containing a transgene or an integrated or episomal vector or expression construct. In certain embodiments, the cells are recombinant because molecule involved in the assay is recombinant; while in others a molecule that is a candidate substance is recombinant.

In particular embodiments, cultured cells are used in transcription assays to evaluate the level of transcription using a reporter gene. In certain examples, the transcription assay is used to measure any change in transcription levels based on any change in Notch activation due to a candidate substance. A promoter with binding sites for transcription factors that are affected by Notch activation may be employed. Such transcription factors and their binding sites are well known to those of skill in the art, for instance, Hsieh et al., 1996, which is hereby incorporated by reference.

V. Therapeutic and Preventative Methods

A. Pharmaceutical Formulations, Delivery, and Treatment Regimens

In an embodiment of the present invention, there are methods for effecting a physiological result, such as downregulation of Notch or increased availability of skeletrophin. In certain embodiments of the invention, there are methods of achieving a therapeutic effect, such as treatment of DM1 or treatment of a condition, disease, or disorder characterized by Notch activation or a nucleic acid with a nucleotide repeat region.

An effective amount of the pharmaceutical composition, generally, is defined as that amount sufficient to detectably and repeatedly to ameliorate, reduce, minimize or limit the extent of the disease or its symptoms. More rigorous definitions may apply, including elimination, eradication or cure of disease.

To effect a physiological or therapeutic effect using the methods and compositions of the present invention, one would generally contact a cell with the therapeutic compound or candidate therapeutic agent, such as a protein or an expression construct encoding a protein. The routes of administration will vary, naturally, with the location and nature of the lesion, and include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation.

To effect a therapeutic benefit with respect to a nucleotide repeat disease, condition, or disorder, one would contact a cell having the relevant nucleic acids and exhibiting the unwanted phenotype with the therapeutic compound. Any of the formulations and routes of administration discussed with respect to the treatment or diagnosis of cancer may also be employed with respect to such diseases and conditions.

Continuous administration also may be applied where appropriate. Delivery via syringe or catherization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention.

Treatment regimens may vary as well, and often depend on disease progression, and health and age of the patient. Obviously, certain conditions, disorders, or diseases will require more aggressive treatment, while at the same time, certain patients cannot tolerate more taxing protocols. The clinician will be best suited to make such decisions based on the known efficacy and toxicity (if any) of the therapeutic formulations.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of plaque forming units (pfu) or viral particles (vp) for a viral construct. Unit doses range from $10^3$, $10^4$, $10^5$, $10^6$, $10^7$, $10^8$, $10^9$, $10^{10}$, $10^{11}$, $10^{12}$, $10^{13}$ pfu or vp and higher. Alternatively, depending on the kind of virus and the titer attainable, one will deliver 1 to 100, 10 to 50, 100-1000, or up to about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, or $1\times10^{15}$ or higher infectious viral particles (vp) to the patient or to the patient's cells. Alternatively, in the case of other substances, such as proteins, the amount administered may be expressed in terms of It is specifically contemplated that the candidate substance, candidate therapeutic agent, or skeletrophin is administered to the subject over a period of time of about, of at least about, or at most about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96 hours or more, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more, 1, 2, 3, 4, 5, 6, 7, 8, 9, 10, 11, 12 weeks or more, 1, 2, 3, 4 months or more, or any range derivable therein.

In other embodiments, methods involve administering a dose or dosage of a compound or agent to the subject. It will be understood that the amount given to the subject may be dependent on the weight of the subject and this may be reflected in the the amount given in a day (i.e., a 24-hour period). In some embodiments, a subject is given about, less than about, or at most about 0.005, 0.05, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 100, 110, 120, 130, 140, 150 nM/kg/day, or any range derivable therein. Alternatively, the amount of compound or agent that is administered can be expressed in terms of nanogram (ng). In certain embodiments, the amount given is about, less than about, or at most about 0.005, 0.05, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 ng/kg/day, or any range derivable therein.

B. Injectable Compositions and Formulations

Pharmaceutical compositions disclosed herein may alternatively be administered parenterally, intravenously, intradermally, intramuscularly, transdermally or even intraperitoneally as described in U.S. Pat. No. 5,543,158; U.S. Pat. No. 5,641,515 and U.S. Pat. No. 5,399,363 (each specifically incorporated herein by reference in its entirety).

Injection of nucleic acid, small molecules, or proteins may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

In certain embodiments, the agent or substance may be administered to the subject in prodrug form, meaning that it will become the active agent or substance once it has entered the subject's body, or a certain body cavity or cell.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

In certain embodiments, the present invention concerns compositions comprising one or more lipids associated with a nucleic acid, an amino acid molecule, such as a peptide, or another small molecule compound. A lipid is a substance that is characteristically insoluble in water and extractable with an organic solvent. Compounds than those specifically described herein are understood by one of skill in the art as lipids, and are encompassed by the compositions and methods of the present invention. A lipid component and a non-lipid may be attached to one another, either covalently or non-covalently.

It is contemplated that a liposome/Fortilin modulator composition may comprise additional materials for delivery to a tissue. For example, in certain embodiments of the invention, the lipid or liposome may be associated with a hemagglutinating virus (HVJ). This has been shown to facilitate fusion with the cell membrane and promote cell entry of liposome-encapsulated DNA (Kaneda et al., 1989). In another example, the lipid or liposome may be complexed or employed in conjunction with nuclear non-histone chromosomal proteins (HMG-1) (Kato et al., 1991). In yet further embodiments, the lipid may be complexed or employed in conjunction with both HVJ and HMG-1.

In certain embodiments, it may be advantageous to employ an agent that reduces the toxicity of a lipid-based compound. It has been reported that the use of an anti-inflammatory drug such as celecoxib reduces toxicity when administered prior to the lipid.

C. Combination Treatments

The compounds and methods of the present invention may be used in the context of diseases/conditions including myotonia. In order to increase the effectiveness of a treatment with the compositions of the present invention, it may be desirable to combine these compositions with other agents effective in the treatment of those diseases and conditions. For example, the treatment of a DM1 or other myotonia may be implemented with therapeutic compounds of the present invention and other therapies. Such therapies may include mexilitene, gabapentin, nonsteroidal anti-inflammatory medications, low-dose thyroid replacement, low-dose steroids, and/or tricyclic antidepressants. When used as part of a comprehensive pain management program, low-dose analgesics may provide relief in conjunction with an agent or compound of the present invention.

Administration of the therapeutic agent or substance of the present invention to a patient will follow general protocols for the administration of that particular secondary therapy, taking into account the toxicity, if any, of the treatment. It is expected that the treatment cycles would be repeated as necessary. It also is contemplated that various standard therapies, as well as surgical intervention, may be applied in combination with the described therapy.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Generation of Constructs of Moderate Expanded CTG (500-700 Repeats) and Longer CTG, CCTG Repeats (>1000) Under T7 Promoter In order to generate in vitro transcribed CUG and CCUG RNA, the long CTG, CCTG repeats were placed under the T7 promoter for in vitro transcription of repeats RNA. A unique methodology was developed to clone different length of CTG and CCTG repeat sequences in plasmid DNA and propagate them in bacteria (Sarkar et al., 1998). The 1.5 kb-2.0 kb and >3.0 kb of uninterrupted pure CTG, >4.0 kb of pure CCTG duplexes were ligated into a modified pcDNA3.1/Hygro(+) (Invitrogen) vector (pSS333) linearized by restriction digested with EcoR V. The ligated product was transformed into E. coli SURE strain (Stratagene) and grown according to the protocol described previously (Sarkar et al., 1998). The resulting clones were digested with Nhe I and PspOMI that flanked the repeat sequences to evaluate the length of cloned repeat sequences.

Example 2

Generation of Long (>3 KB) Single-Stranded RNA Encoding CUG and CCUG

The generation of single-stranded CUG and CCUG RNA repeats is the most important step to achieve the objectives proposed in this study. However, cloning longer repeat sequences has been difficult mainly because the repeat sequences show high degree of instability when grown in bacteria (Hashem et al., 2002a; Hashem et al., 2002b). A unique methodology to clone and stabilize longer CTG and CCTG repeat sequences in bacteria has been developed (Sarkar et al., 1998). Using this methodology, clones of 3 to 5 kb of CTG and CCTG repeats in plasmid DNA can be achieved. A clone of >3 kb of CTG and CCTG repeat in pSS333 to generate plasmid pSS333-CTG and pSS333-CCTG has been produced. These plasmids were designed in a way such that the cloned repeat sequences are flanked by T3 and T7 promoters. The vector encoding larger than 3 kb of CTG and CCTG repeat sequences were linearized with PspOMI and then the biotin-labeled CUG RNA was produced by using Riboprobe® T7 in vitro transcription System (Promega) with biotinylated NTPs.

The biotin-labeled single-stranded CUG and CCUG RNA were treated with DNase to remove the DNA contaminations from the reaction product, and then purified and used as bait to isolate and identify the CUG and CCUG repeats specific binding proteins from mouse muscle extract.

Example 3

Identification of Skeletrophin, a Protein Sequestered by Long CUG RNA from Skeletal Muscle To identify proteins that are sequestered by expanded CUG RNA, nuclear extracts from skeletal muscle were made using NE-PER Nuclear and Cytoplasmic Extract Reagents (Pierce). Vendor's instructions were followed to obtain protein extracts wherein the native structure and activity of the extracted proteins remain unperturbed. In order to identify the CUG and CCUG RNA binding proteins, the protein extract from muscle was first incubated with the RNA encoding single-stranded but structured CUG RNA. In vitro transcribed long biotin-labeled CUG RNA and control RNA (single-stranded lacZ RNA) was incubated with magnetic beads. Nuclear extracts from mouse skeletal muscle was added to the mixture of biotin labeled RNA and magnetic beads and then incubated at 4° C. for overnight. The unbound proteins were washed by RNA wash buffer. The remaining proteins that are bound with CUG-RNA were eluted out by boiling the beads with 1×SDS-PAGE loading buffer and the eluted proteins were loaded on a 4-20% SDS-PAGE. The protein bands that are additional compared to the proteins present in controls RNA were identified, the bands were cut out, trypsin digested and finally analyzed using MALDI-TOF assay at Bio-Molecular Resource Facility Mass Spectrometry Core at UTMB. The protein sequences were identified by a search of the rodent protein database. Each experiment was done for four times with five different protein extracts isolated from four different animals. Skeletrophin was identified as a sequestered protein. FIGS. 2A-B provides information of skeletrophin, the novel CUG RNA binding protein.

Example 4

Skeletrophin Co-Localizes with the Long CUG RNA Nuclear FOCI

In DM1 and DM2, RNA encoding CUG and CCUG RNA are produced in tissues and the repeat RNA sequester MBNLs in vivo. The sequestration of muscle-blind proteins is an important step in DM pathogenesis but Mbnl1 knockout mice do not develop dystrophic muscle defects indicating that expanded CUG RNA may sequester proteins in addition to the muscle-blind proteins.

In order to determine whether skeletrophin indeed binds and co-localizes with expanded CUG RNA in cells expressing long CUG, co-localization experiment were carried out by co-transfecting pSS333-CTG and GFP-skeletrophin fusion construct into C2C12 myoblasts. The transfected cells were fixed and further hybridized with Cy3-labeled $(CAG)_{10}$ riboprobe. The green fluorescence from the fusion-protein and red fluorescence from the CAG riboprobe were detected using a Zeiss LSM 510 UV META Laser Scanning Confocal Microscope. Based on these experiments, it was observed that skeletrophin indeed co-localizes with the expanded CUG RNA in vivo. Skeletrophin mRNA was expressed in normal skeletal muscle, and to a lesser extent in heart and brain (Mankodi et al., 2000; Mankodi et al., 2002). These results suggest that sequestration of skeletrophin may play crucial role in DM pathogenesis.

In order to understand whether the cellular localization of skeletrophin is altered in DM1 cells, the inventors first constructed a GFP-skeletrophin fusion protein. The EcoRI-BglII fragment of the human skeletrophin was purified and then cloned in-frame with GFP into EcoRI-BamHI digested pEGFP-C1 vector (Clonetech). The plasmid encoding GFP-skeletrophin was transfected into normal and CUG-expressing muscle cells. The transfected cells were counter-stained with TO-PRO-3 and photographed under fluorescent microscope. The preliminary results show that in normal cells, skeletrophin is primarily present in the cytoplasm but in DM1 cells skeletrophin is sequestered in the nuclei.

Example 5

Identification of Long CUG RNA Interacting Proteins, LCUG-IP1 and LCUG-IP2 from Muscle and Co-Localization of CUG RNA FOCI with them By using biotin-labeled long CUG-RNA as bait, another two novel CUG RNA interacting proteins, LCUG-IP1 and LCUG-IP2 were identified in muscle. In order to determine whether LCUG-IP1 and LCUG-IP2 indeed binds and co-localizes with expanded CUG RNA foci, co-localization experiments were carried out. Nucleic acid with CUG repeats was co-transfected with GFP-LCUG-IP1 and GFP-LCUG-IP2 constructs into C2C12 cells respectively. The transfected cells were then fixed and further hybridized with Cy-3-labeled (CAG)10 riboprobe. The green fluorescence from the fusion-protein and red fluorescence from the CAG riboprobe were detected under fluorescent microscope. Images using confocal microscopy showed that LCUG-IP1 and LCUG-IP2 indeed co-localizes with the expanded CUG RNA in vivo respectively. Those data suggest that sequestration of LCUG-IP1 and LCUG-IP2 may also play a crucial role in DM pathogenesis.

The long CTG and CCTG repeats were stabilized in the plasmids by the following process. The CTG and CCTG duplexes were PCR amplified from genomic DNA isolated from DM1 or DM2 patients. The PCR products were then ligated with plasmid DNA by standard ligation procedure (T4 DNA ligase). The ligated product was transformed into XL10Gold or SURE bacterial strain (Stratagene) and plated on LB Agar plate and the plated were incubated at room temperature for 2 to 3 days. The bacterial colonies were inoculated in LB and grown at 12-16° C. for 7 to 8 days. The plasmid DNA was isolated and the repeat lengths in the plasmids were measured by restriction analyses and 30 to 40% of the colonies carried repeat DNA sequences as large as 5 kb. This modified procedure allowed the cloning of longer (3 to 5 kb) of CTG or CCTG repeat sequences.

CUG and CCUG RNA sequences were able to be generated by transcribing the repeats by T3 or T7 RNA polymerase promoter and able to develop the novel RNA binding assay, and identified several proteins associated with long CUG RNA repeats. These techniques will allow researchers to further isolate and identify the complete spectrum of the long CUG, CCUG RNA specific binding proteins in different tissues in order to understand the RNA gain of function in the multi-systemic nature of myotonic dystrophies as well as the phenotypic differences between DM1 and DM2. Moreover, these techniques can be employed in the context of other diseases and conditions characterized by or involving long repeat sequences.

Example 6

Development of Transgenic Mice with Long Repeat Construct

In order to develop the transgenic models for DM1 and DM2, the backbone of the transgenic vectors was first constructed. In the first sets of transgenic constructs, a 2.2 kb fragment of human α-actin promoter (Mankodi et al., 2003; Frauli et al., 2003) was cloned upstream of the β-galactosidase gene. A rabbit β-globin intron (approximately 0.8 kb) was cloned downstream of the α-actin promoter for the proper transcription and transport of the transgene (Tang et al., 1993). Transgenic plasmid vector was digested with SwaI and linearized vector DNA was gel purified (Qiagen). The uninterrupted pure CTG and CCTG duplexes were ligated with the linearized vector. The ligated product was transformed into *E. Coli* SURE strain (Stratagene) and grown according to the protocol described previously (Sarkar et al., 1998). The resulting clones were digested with SfiI that flanked the repeat sequences to evaluate the length of cloned repeat sequences. To develop DM2 transgenic models, the CCTG duplexes were cloned in the 3' un-translated region of β-galactosidase gene and upstream of BGH polyA sequences (FIGS. 2A-B). In both cases, the human α-actin promoter cloned upstream drives the expression of the transgene and the repeat sequences in skeletal muscle.

In the second set of transgenic constructs, first the 3.2 kb SacI-XhoI fragment encoding the human DMPK exon 15 and part of Exon 1 of Six5 was cloned downstream of the human α-actin promoter and upstream of BGH polyA sequences (FIG. 3B). A polylinker was introduced at the BsmI site at the CTG expansion locus. The CTG expansion loci encoding expanded CTG sequences (3 to 5 kb) were PCR amplified with the flanking primers. The amplified PCR products encoding 3 to 5 kb of the CTG sequences were cloned into the EcoRV site of the transgenic plasmid vector (within exon 15 of DMPK) as shown in FIGS. 4A1-4A3. The transgenic plasmid encoding the CTG sequences was propagated as described previously (Sarkar et al., 1998).

The transgenic plasmids were digested with NheI and SexA1, which flank the entire transgene and the digested DNA was run on agarose gel. The 12 kb DNA band that represents the entire functional transgene was purified from agarose gel using gel extraction kits (Qiagen). Purified transgene fragments were transfected into mouse myoblast C2C12 cells to check the integrity and proper expression of the repeat sequences. The transgenic constructs (FIGS. 3A-B) were then injected into the pro-nuclei of fertilized mouse eggs. The injected eggs were grown in culture and embryos were implanted in the uterus of pseudo-pregnant females. The founder animals encoding the entire transgene were identified by both PCR and Southern blotting.

Example 7

Sequence Interruptions within the Expanded CTG Repeats Play Important Role in their Ability to Form RNA-Protein Complexes A large body of experimental evidences suggest that in DM1, the DMPK transcripts encoding expanded CUG RNA form strong intra-nuclear RNA-protein complexes and the RNA-protein complexes appear as bright nuclear foci when hybrididized with fluorescent-labeled CAG riboprobes (Mankodi and Thornton, 2002; Mankodi et al., 2003; Amack and Mahadevan, 2001; Fardaei et al., 2001; Fardaei et al., 2002). Interestingly, preliminary results using FISH analysis showed that uninterrupted CTG repeat tracts (1 to 3 kb) do not form intra-nuclear RNA-protein complexes rather form cytoplasmic RNA-protein complexes.

To understand whether the 3' UTR of DMPK determines the cellular locations of RNA-protein complexes, a 3.2 kb SacI-XhoI fragment of the DM1 locus was cloned downstream of the α-actin promoter as shown in FIGS. 4A1-4A3. Approximately 3 kb of synthetic uninterrupted CTG duplexes within the DMPK 3' UTR was cloned as shown in FIGS. 4A1-4A3. Importantly, these CTG sequences when expressed along with the DMPK 3'UTR sequences also formed strong cytoplasmic complexes. This result suggests that the 3'UTR does not play major role in determining the localization of RNA-protein complexes. A preliminary sequence analysis of the expanded DM1 locus show that CTT interruptions commonly occur within the expanded CTG sequences. The interrupted CTG sequences when expressed either from the DM1 locus or from context-independent locus were found to form strong intra-nuclear RNA-protein complexes. Taken together, these results suggest that interruptions within the expanded CTG sequences act as a cis-regulatory element that determines cellular localization of RNA-protein complexes. At present the nature of these two different classes of complexes are not known. To understand the functional significance of sequence interruptions within the expanded CTG repeat sequences a second series of transgenic vector was constructed as shown in FIGS. 4A1-4A3 to develop transgenic mice expressing interrupted CTG sequences amplified from DM1 genomic DNA (see Example 7). These mice can be used to evaluate the role of the sequence interruptions in modulating the disease severity and complexity.

Example 8

Longer $(CTG)_n$ Sequences Show Higher Degree of Instability Compared to the $(CCTG)_n$ Sequences Plasmid DNA encoding approximately 5 kb of CTG and CCTG duplexes were transformed into *E. coli* SURE® strain (Stratagene). Several colonies were grown in LB media and were grown according to the protocol described previously (Mankodi et al., 2002). The plasmid DNA isolated from each bacterial culture was digested with SfiI sites which flank the repeat sequences and the digested product was run on agarose gel. The gel showed that the (CCTG)n repeats sequences are more stable in bacteria compared to the CTG sequences under identical growth conditions. Higher degree of instability of CTG sequences suggest that expanded CTG sequences may adopt a more complex structure in vivo compared to the CCTG repeats. The transcribed CUG RNA may thus form more complex three-dimensional structures compared to the CCUG RNA and complex CUG-RNA may thus sequester multiple proteins establishing more complex muscle phenotypes in DM1.

Example 9

Loss of Skeletrophin Inhibits Differentiation of Mouse Myoblast C2C12 Cells

Sequestration of muscle-blind proteins by long CUG RNA has been shown to be an important pathogenic mechanism to develop DM phenotypes. The double-stranded CUG RNA complexes with muscle-blind proteins and depletion of muscle-blind proteins alter the splicing pattern of a number of transcripts (Ho et al., 2004). The change in splicing pattern is an important mechanistic step to cause myotonia and muscle structural abnormalities characteristic of DM. To determine the consequence of the loss of skeletrophin in the maintenance of muscle cell the inventors inactivated skeletrophin by SiRNA, siGENOMET™ SMARTpool® skeletrophin siRNA (Dharmacon). SiRNA specific for skeletrophin was transfected into C2C12 mouse myoblast cells using Lipofectamine 2000 (Invitrogen). Results showed that siRNA-mediated inactivation of skeletrophin in C2C12 mouse myoblast cells inhibits proper myogenesis of myoblast cells when differentiation was induced.

Example 10

Expression and Purification of Skeletrophin in Bacteria

In order to understand the expression pattern of skeletrophin in normal and DM tissues the ability to obtain pure active protein to study the RNA-binding properties of skeletrophin is important. The human skeletrophin cDNA was PCR amplified with specific primers which encode NdeI and XhoI restriction sites. The entire coding region of skeletrophin was PCR amplified from its cDNA and the purified PCR product was digested with XhoI and NdeI and then cloned into XhoI-NdeI digested pET bacterial expression vector (pET22b) (Novagen). The identity of the resulting expression vector was checked by restriction analysis and by sequencing. Protein expression was confirmed using protein extracts prepared with and without IPTG induction. Over-expressed his-tagged skeletrophin was identified on an SDS-PAGE gel stained with Coomassie Blue.

Example 11

Northern Blot Analysis of Skeletrophin

In order to determine the expression pattern of skeletrophin in various tissues we carried out Northern blot analysis of the total RNA isolated from various adult tissues as well from embryos at different developmental stages. Northern blot analysis shows that skeletrophin is highly expressed in muscle, heart and brain with predominant expression in the skeletal muscle. The human and mouse skeletrophin cDNA was radio-labeled with $\alpha$-32-P-dCTP and the membrane containing human and mouse total RNA, isolated from different tissues was hybridized with the radio-labeled cDNA probe using Expresshyb® (Clonetech) hybridization buffer. The membrane was washed twice with 2×SSC containing 0.1% SDS to remove non-specific hybridization signals and then exposed to X-ray film. Northern analysis indicates that skeletrophin is highly expressed in skeletal muscle, heart and brain with detectable expression in other tissues (FIGS. 6A-B).

Example 12

Development of Transgenic Mice Expressing >3 KB of CUG RNA Sequences in Brain In DM1, large CTG repeat expansion is associated with psychiatric illness, developmental defects and mental retardation (Harper, 2001; Groenen and Wieringa, 1998; Mankodi and Thornton, 2002; Amack and Mahadevan, 2004; Machuca-Tzili et al., 2005; Monckton and Ashizawa, 2004; Nagamitsu and Ashizawa, 2002). To determine the mechanism by which longer (greater than 3 kb) CUG RNA cause CNS defects transgenic mice expressing greater than 3 kb of CUG sequences were developed. The mouse prion promoter (PrP) (approximately 3.5 kb) was cloned upstream of the $\beta$-galactosidase to achieve predominantly CNS-specific expression of the reporter gene and the CUG repeats. Bovine Growth Hormone (BGH) polyadenylation sequences were cloned downstream of the reporter gene to achieve proper polyadenylation of the transcripts. CTG duplexes were cloned at the SwaI site located downstream of $\beta$-galactosidase gene and upstream of the BGH polyA sequences to develop CUG transgenic mouse models. FIG. 8 represent the transgenic construct for DM1. These clones encoding greater than 3 kb kb CTG were digested with flanking restriction enzymes (Sfi I) and the approximately 13 kb transgene was purified from agarose gel. The purified DNA fragment was microinjected into fertilized mouse eggs. PCR analysis of tail-clip DNA with lacZ-specific primers confirmed the presence of a 750 bp band in founder animals.

Example 13

Identification of Novel Proteins Sequestered by Long CUG RNA from Brain

To identify proteins sequestered by long CUG RNA (>3.0 kb), nuclear extracts from brain was made using NE-PER Nuclear and Cytoplasmic Extract Reagents (Pierce). In order to identify the CUG RNA binding proteins, the protein extract from brain was first incubated with the RNA encoding single-stranded CUG RNA. In vitro transcribed biotin-labeled CUG RNA and control RNA (single-stranded lacZ RNA) was incubated with magnetic beads. Nuclear extracts from mouse brain extract was added to the mixture of biotin labeled RNA and magnetic beads and then incubated at 4° C. for overnight. The unbound proteins were washed by RNA wash buffer. The remaining proteins that are bound with CUG-RNA were eluted out by boiling the beads with 1×SDS-PAGE loading buffer and the eluted proteins were loaded on a 4-20% SDS-PAGE. The protein bands that are additional compared to the proteins present in controls RNA were identified, the bands were cut out, trypsin digested and finally analyzed using MALDI-TOF assay. The protein sequences were identified by a search of the rodent protein database. Each experiment was done for four times with five different protein extracts isolated from four different animals.

Skeletrophin was observed to specifically bind CUG RNA, but not control RNA, using biotin-labeled RNA binding assay followed by mass spectroscopy.

Example 14

Skeletrophin Co-Localizes with CUG RNA-Protein Aggregates in PC12 Cells

Using biotin-labeled CUG RNA, skeletrophin was found to form a complex with longer CUG RNA. To determine whether skeletrophin indeed binds and co-localizes with the expanded CUG RNA in DM cells, the GFP-tagged skeletrophin fusion construct was transfected into PC12 cells (and C2C12 cells described above) expressing 1500 repeats of CUG RNA. The transfected cells were fixed and further hybridized with Cy-3-labeled $(CAG)_{10}$ riboprobe. The green fluorescence from the fusion-protein and red fluorescence from the CAG riboprobes were detected under fluorescent microscope. Using this methodology, skeletrophin was observed to co-localize with CUG RNA in vivo.

Example 15

Skeletrophin Co-Localizes with CUG RNA Nuclear FOCI in DM1 Fibroblasts

In the previous experiment it was demonstrated that skeletrophin co-localizes with the CUG RNA in PC12 cells expressing 3 kb of CUG RNA. In order to determine whether skeletrophin co-localizes with the CUG RNA in vivo, the GFP-skeletrophin fusion construct was transfected into DM1 fibroblast cells by Nucleofector technology using the normal human adult dermal fibroblasts (NHDF-adult) kit (Amaxa).

Transfected cells were fixed and further hybridized with Cy-3-labeled $(CAG)_{10}$ riboprobe. TOPRO-3 was used for nuclear staining. Green fluorescence from the fusion-protein and red fluorescence from the CAG riboprobe were detected under fluorescent microscope, showing that skeletrophin co-localize with the expanded CUG RNA in vivo in DM1 fibroblasts.

Example 16

Loss of Skeletrophin Inhibits Differentiation of C2C12 Cells

SKELETROPHIN is the ortholog of Drosophila mindbomb, a novel E3 ubiquitin ligase for Jagged2, the ligand for Notch, the signaling receptor (Takeuchi et al., 2005; Artavanis-Tsakonas et al., 1999; Blaschuk and Ffrench-Constant, 1998). The ubiquitination and subsequent degradation of Jagged2 plays a crucial role in modulating Notch signaling. Notch gene-family encodes transmembrane receptors critical for various cell-fate decisions during all stages of development (Artavanis-Tsakonas et al., 1999). One important function of Notch is to control the divergent programs of differentiation among spatially proximal groups of equipotent progenitor cells. Activation of Notch receptors results in inhibition of differentiation which can transduce signals to the neighboring cells (Artavanis-Tsakonas et al., 1999). To determine the consequence of the loss of function of skeletrophin, skeletrophin was inactivated using mouse siRNAs from Dhamacon in C2C12 cells. 24 h after transfection of the siRNAs, cells were switched to differentiation medium for 6 days. The results showed that the differentiation of C2C12 was significantly reduced upon inactivation of skeletrophin based on visual observation of the cells. To determine whether inhibition of C2C12 differentiation results from the upregulation of Jagged2 the expression level of Jagged 2 was measured after treating the cells with siRNA. Jagged2 level was increased in C2C12 cells when skeletrophin was inactivated (FIG. 9). Similar increase in Jagged2 levels were also observed in C2C12 cells expressing long CUG RNA (FIG. 9). These results indicate that the loss of function of skeletrophin may play important role in initiating an aberrant Notch signaling disrupting differentiation in DM1.

Example 17

The Notch-Signaling is Up-Regulated in DM1 Fibroblasts

In the previous experiment it was demonstrated that either the inactivation of skeletrophin or the expression of CUG RNA in C2C12 cells up-regulates Jagged2 (FIG. 9). This result indicates that the sequestration of skeletrophin may trigger Notch hypersignaling in DM1 cells causing aberrant differentiation. In order to establish whether Notch signaling is indeed hyper-activated in DM1 cells a comparison was made between the expression levels of Jagged2 and Notch 1 receptor in DM1 fibroblasts with normal fibroblasts. Interestingly, approximately a 60% increase in Jagged2 expression and 2-3 folds increase in Notch 1 were observed in DM1 fibroblasts whereas skeletrophin levels remained unaltered (FIGS. 10A-D). To determine whether transcriptional activity of the downstream target genes are increased as the result of enhanced Notch-signaling the inventors transfected the Notch-signaling-luciferase reporter vector (8×wtCBF1Luc) (Hsieh et al., 1996) into DM1 fibroblasts. Measurement of luciferase levels suggest a significant increase in Notch signaling in DM1 fibroblasts compared to the normal fibroblasts (FIG. 10D). These data support the proposition that Notch-signaling is indeed hyper-activated in DM1 cells.

Example 18

Notch Hyper-Signaling in DM1 Fibroblasts Inhibits Differentiation of C2C12 when Co-Cultured Experimental evidences show that co-culture of fibroblasts expressing Jagged2 with C2C12 myoblasts inhibit myogenic differentiation, accompanied by increased Notch 1 and Notch 3 (Luo et al., 1997). The upregulation of both Jagged2 and Notch in DM1 fibroblasts may be responsible for establishing a dysfunctional myogenesis and neurogenesis. To establish a correlation between aberrant Notch signaling in DM1 fibroblast and its influence in differentiation of the neighboring cells, C2C12 cells were co-cultured with DM1 and normal fibroblasts and their differentiation after 6 days of co-culture was observed. The differentiation of C2C12 cells was significantly inhibited in presence of DM1 fibroblast whereas the differentiation was enhanced in presence of normal fibroblast.

It is possible that Notch hyperactivity in DM1 cells may transduce signal to the neighboring C2C12 cells inhibiting their differentiation. Western blot analysis of the C2C12 cell extract showed significant downregulation of Jagged-2 and its receptor Notch in C2C12 cells when co-cultured with DM1 fibroblast with respect to the control (FIGS. 11A and 11C). Reduced expression of myogenin in cell extract isolated from the co-culture indicates dysfunctional myogenesis of the C2C12 cells (FIG. 11B). These data suggest that loss-of-skeletrophin results in increased Jagged2 and Notch activity in DM1 fibroblast which can potentially inhibit differentiation. Similarly, the hyperactivation of the Notch signaling in DM1 cells can inhibit neurogenesis and cause developmental defects in the entire central nervous system.

Example 19

Down-Regulation of Skeletrophin in DM1 Up-Regulate the Notch Signaling

To determine whether up-regulated Notch signaling in DM1 results from the down-regulation of active skeletrophin by its sequestration into the CUG RNA foci, human skeletrophin-specific siRNA was transfected into normal human fibroblasts. The human siRNA was purchased from Dharmacon and the human fibroblasts were purchased from Cell Applications. As expected, both Notch signaling ligand Jagged2 and Notch1 were indeed up-regulated when skeletrophin was inactivated (FIG. 12). This result suggests that sequestration of skeletrophin plays a causal role in DM1 pathogenesis by up-regulating Notch signaling inhibiting neurogenesis and myogenesis.

Example 20

Development of Knockout Vector for Targeted Deletion of Skeletrophin

The development of skeletrophin-deficient mouse lines is important to delineate the mechanism by which sequestration of skeletrophin causes aberrant neurogenesis and brain development in DM1. We have subcloned the genomic arms (5, and 3, regions of homology) and have completed the construction of the final targeting vectors for developing both traditional and conditional knockout mice as shown in FIG. 13.

Example 21

CUG RNA Upregulates Notch in C2C12 Cells

To establish that sequestration of skeletrophin is the primary mechanism of Notch hyperactivity, we expressed different lengths of CUG RNA in C2C12 cells. Western blotting showed that C2C12 cells expressing longer (2 and 3 kb) (CUG)n sequences had increased Jagged2 (lane 3 and 4) compared to shorter (0.3 and 0.6 kb) (CUG)n sequences. Additionally, expression of long CUG RNA recreated Notch hyperactivity (FIG. 14).

Example 22

Figure 15:
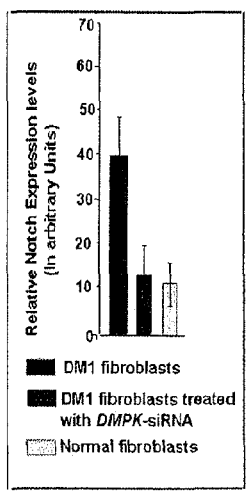
FIG. 15. Disruption of the CUG-foci in DM1 cells rescues Notch hyperactivity: Histogram showing the relative Notch levels in DM1 fibroblasts (black), DMPK-siRNA-treated DM1 fibroblasts (blue) and control-siRNA-treated normal fibroblasts (grey).

Disruption of the RNA-Protein Complexes in DM1 Fibroblasts Rescues Notch Hyperactivity in DM1 Fibroblasts To further confirm that sequestration of skeletrophin by expanded CUG RNA is the primary cause for Notch hyperactivation, mutant DMPK was inactivated by siRNA and the results showed that Notch hyperactivity is rescued upon inactivation of mutant DMPK transcripts. A Western blot showed that Notch levels in DM1 fibroblasts was higher and downregulated when treated with DMPK-siRNA. All the siRNA were purchased from Dharmacon. Notch expression in siRNA-DMPK-treated cells was similar to that of normal fibroblasts or control siRNA-treated fibroblasts (FIG. 15). Moreover, disruption of (CUG)n-RNA complexes in DM1 cells restores Notch hyperactivity which no longer blocks differentiation. This was also shown in an experiment involving C2C12 cells differentiated into myotubes when cocultured with DM1 fibroblasts, a co-culture of DMPK-siRNA-treated DM1 fibroblasts and C2C12 cells, and a co-culture of normal human fibroblasts and C2C12.

Example 23

Figure 16:
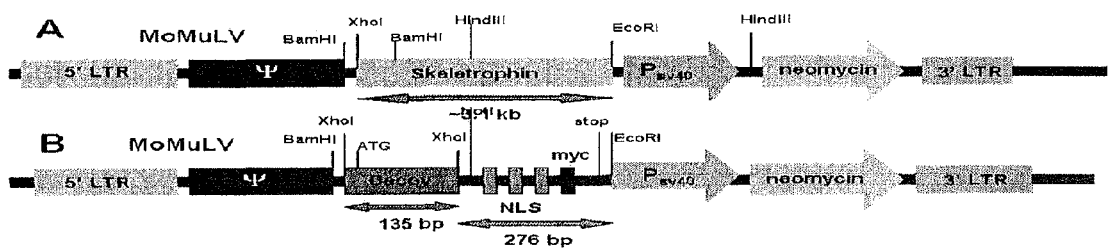
FIGS. 16A-B. Retroviral Vectors: The schematic diagram showing the essential elements of the retroviral vectors expressing skeletrophin cDNA (FIG. 16A) and the skeletrophin Zn-finger decoy peptide (FIG. 16B). C. The restriction digestion of the retroviral vector pLXSN-STRo-decoy with XhoI (lane 2), Lane 1 1 kb DNA marker and D. The HindIII (lane 2) and EcoRI/XhoI (lane 3) digestion of the retroviral construct encoding skeletrophin cDNA, pLXSN-STRo.

Retroviral Constructs Being Used for Rescuing Notch Hyperactivity in DM1 Muscle Cells Retroviral viral constructs have been made (FIGS. 16A-B) that will be used to determine whether Notch hyperactivity can be rescued in DM1 muscle cells.

Example 24

Diminished Skeletrophin Activity Promotes Proliferation of DM1 Myoblasts

Recent studies revealed that, apart from the well-established role of NOTCH in inhibiting differentiation, activated NOTCH promotes proliferation in a wide variety of cell types (Go et al, 1998, Conboy et al, 2002; Takeuchi et al, 2006) and downregulation of SKELETROPHIN results in NOTCH activation and progression of melanoma invasion (Takeuchi et al, 2006). Since there is a marked attenuation of SKELETROPHIN activity and activation of Notch signaling in DM1, we tested whether SKELETROPHIN activity influences the proliferation of DM1 myoblasts. Bromo-uridine (BrdU) incorporation was assessed in proliferating DM1 myoblasts. Fifty to 60% of the DM1 myoblasts incorporate BrdU whereas only 10 to 15% of the control myoblasts incorporated BrdU under identical conditions (n=2; $P<0.0003$). SKELETROPHIN in normal myoblasts was then targeted with siRNA and assessed the BrdU incorporation. The result shows that >50% of the targeted myoblasts incorporate BrdU; in contrast, targeting myoblasts with control siRNA does not influence their BrdU incorporation. These data support that diminished SKELETROPHIN activity favors proliferation and inhibits differentiation, thus skewing the reciprocal balance between proliferation and differentiation in DM1.

Example 25

Targeted Inactivation of Mutant DMPK Transcripts in DM1 Myoblasts Diminishes JAGGED2 and NOTCH1 Activities, and Favors Differentiation The above findings supported the possibility that a significant amount of SKELETROPHIN remained bound with the mutant DMPK transcripts within DM1 nuclei, which results in diminished SKELETROPHIN activity in DM1. The attenuated SKELETROPHIN activity then manifests with an increase in JAGGED2 activity, leading to chronic activation of Notch signaling in DM1. Based on these findings we hypothesize that the activated Notch attenuates the ability of DM1 myoblasts to progress toward myogenic lineage, while facilitating their proliferation. To more critically test this idea, DMPK transcripts were targeted in DM1 myoblasts using siRNA and JAGGED2 and NOTCH1 expression was measured, in addition to an assessment of the cells' myogenic properties. DMPK transcripts were targeted to minimize interactions of SKELETROPHIN with CUG RNA, thereby increasing SKELETROPHIN activity. A marked reduction of the mutant DMPK transcripts was observed and confirmed by FISH analysis, which shows a drastic reduction of the number as well as the intensity of the CUG foci in the siRNA-treated DM1 myoblasts. JAGGED2 and NOTCH1 levels were measured in the DMPK-siRNA-treated cells. Both JAGGED2 and NOTCH1 expression levels were reduced to basal level which was accompanied by a marked increase in myogenin when incubated in differentiation media. Importantly, NOTCH1 in normal myoblasts remained unaltered when treated with either DMPK or control siRNA, indicating that DMPK dosage per se does not influence Notch activity or the myogenic fate of DM1 myoblasts. These results support that mutant DMPK transcripts play a causal role in eliciting aberrant SKELETROPHIN, JAGGED2 and NOTCH1 activities in DM1. When transferred to differentiation media, a large number of these DMPK-siRNA-treated DM1 myoblasts formed multinucleated myotubes and showed pronounced myogenin expression. In contrast, DM1 myoblasts treated with control siRNA formed fewer and shorter myotubes as well as basal myogenin expression under identical conditions.

The BrdU incorporation into DM1 myoblasts suggested the possibility that activated Notch favors proliferation. To obtain more direct evidence, the number of DM1 myoblasts that incorporate BrdU after treatment with DMPK siRNA was assessed. Only 10 to 15% of the DM1 myoblasts incorporated BrdU after treating with DMPK siRNA; in contrast, 50 to 60% of the DM1 myoblasts treated with control siRNA show positive BrdU incorporation, indicating that the mutant DMPK transcripts regulates proliferation rate of the DM1 myoblasts. Importantly, BrdU incorporation in normal myoblasts remained unaltered when treated with DMPK siRNA under identical conditions, indicating that DMPK activity per se does not influence proliferation. Collectively, these observations establish a mechanistic link between mutant DMPK transcripts, Notch signaling and myogenic properties of DM1 myoblasts, supporting our interpretation that mutant DMPK transcripts play an important causal role in eliciting Notch hyperactivity and in determining the myogenic fate of DM1 myoblasts.

Example 26

Attenuating Notch Signaling Ameliorates the Myogenic Potential of DM1 Myoblasts

Whether attenuating Notch signaling improves the myogenic potential of DM1 myoblasts was assessed. To achieve this goal, JAGGED2 was targeted in DM1 myoblasts with siRNA. A Western blot demonstrated that targeting JAGGED2 resulted in >90% reduction of JAGGED2 and NOTCH1. Interestingly, DM1 myoblasts with attenuated JAGGED2 and NOTCH1 exhibited a higher propensity to form multinucleated myotubes when cultured in differentiation media. In addition to producing multi-nucleated myotubes, there was a marked upregulation of MyoD and myogenin in the JAGGED2-siRNA-treated DM1 myoblasts, corroborating the hypothesis that chronically activated Notch impairs the efficacy of myogenic differentiation in DM1.

The above results support the idea that diminished SKELETROPHIN activity results in elevated Notch signaling and activated Notch impairs the efficacy of myoblast differentiation in DM1. To obtain more direct evidence for this interpretation, SKELETROPHIN was overexpressed in DM1 myoblasts and the Notch activity and their myogenic properties were assessed. Overexpression of SKELETROPHIN resulted in a significant reduction of NOTCH1 as well as Notch signaling (n=4; P=0.0031). Importantly, a large number of these myoblasts differentiated and showed pronounced myogenin expressions, demonstrating that forced SKELETROPHIN expression ameliorates the myogenic potential of DM1 myoblasts.

To investigate whether the myogenic potential of DM1 myoblasts was ameliorated by attenuating Notch signaling, γ-secretase activity was blocked with L-685458, a synthetic aspartyl protease transition-state analog that specifically inhibits γ-secretase activity and Notch signaling (Shearman et al, 2000). The pharmacological inhibition of γ-secretase resulted in a dose-dependent reduction of NOTCH1. Importantly, a large number of the drug-treated DM1 myoblasts exhibited a higher propensity to form multi-nucleated myotubes despite the presence of distinct nuclear foci. The progression of myogenesis was quantified by monitoring the expression of myogenic markers, myogenin and MyoD. The increase of myogenin and myoD and a higher propensity of DM1 myoblasts to form myotubes suggest that pharmacological attenuation of Notch signaling facilitates the progression of DM1 myoblasts towards myogenic lineage. In contrast, untreated DM1 myoblasts show reduced myogenin and MyoD even after prolonged incubation in differentiation media.

Example 27

Expressions of PGC-1α is Significantly Downregulated in DM1 Skeletal Muscle

The studies above showed that the expanded CUG sequences encoded in the mutant DMPK transcripts complex with skeletrophin and that depletion of skeletrophin activity results in chronic activation of Notch signaling in DM1 skeletal muscle. The activated Notch intracellular domain (NICD) has been shown to complex with the MADS-box transcription factor MEF2C, specifically blocking the DNA-binding by MEF2C, which results in drastic downregulation of MEF2C activity and expressions of the genes regulated by MEF2C. The ankyrin domain of the activated Notch has been shown to bind with the 12-amino acid region immediately next to the DNA-binding domain of MEF2C (which is unique to this MEF2 isoform), blocking transcriptional activities of MEF2C. The MEF2 proteins, specifically the MEF2C isoform binds upstream CTA(A/T)$_4$TAG/A (SEQ ID NO:6) consensus sequences in the control region of several genes including PGC-1α and activate their transcription. Since Notch signaling is chronically activated in DM1 skeletal muscle, experiments were conducted to determine whether that activated Notch is sufficient to downregulate PGC-1α expression. Notch1 and PGC-1α expression was measured in DM1 skeletal muscles and the Western blot results showed that Notch1 expression is 2- to 3-fold elevated in DM1 skeletal muscle whereas the PGC-1α is 50 to 60% lower in DM1 compared to the controls; the MEF2C expressions are not significantly different in DM1 skeletal muscle compared to the controls. These results provide evidence that constitutively activated Notch signaling results in diminished PGC-1α expressions.

Example 28

Activation of Notch Signaling Results in Significant Downregulation of PGC-1α Expression Since MEF2C regulates PGC-1α transcription, whether activated Notch is sufficient to downregulate PGC-1α expression was investigated. In order to recreate elevated Notch signaling, normal human myoblasts were introduced with skeletrophin siRNA and Western blotting was done to measure Notch1 and PGC-1α expression. Consistent with previous observations, the targeted inactivation of skeletrophin resulted in a stark decrease of uncleaved Notch1 (120 kD), but significant upregulation of cleaved Notch1 (65 kD) and concomitant decrease in PGC-1α expression Importantly, targeting skeletrophin did not change the MEF2C levels in normal myoblasts. Because Notch signaling is chronically activated in DM1 skeletal muscle, these findings provided the basis for investigating whether this diminished PGC-1α regulates mitochondrial integrity, function and oxidative capacity of DM1 skeletal muscle.

Example 29

Expression of the Nuclear DNA-Encoded Genes that Constitute the Mitochondrial Oxidative Phosphorylation Chain are Markedly Downregulated in DM1

PGC-1α functions as a key regulator of mitochondrial biogenesis and respiration in both skeletal and cardiac muscle. PGC-1α, in collaboration with the nuclear respiratory factor 1 (NRF-1), binds upstream of several nuclear genes such as nuclear DNA-encoded GA-binding protein (GABPα), several subunits of the Oxidative Phosphorylation Chain subunits, mitochondrial assembly and transport proteins, and mitochondrial transcription stimulatory factors (Tfam, TBF1M and TBF2M). The nuclear DNA-encoded mitochondrial transcription stimulatory factors Tfam, TBF1M and TFB2M facilitate mtRNA-polymerase activity to initiate transcription of the mtDNA-encoded genes such as several subunits of the OxPhos subunits, tRNA and rRNA genes, essential for mitochondrial integrity, function and mitochondrial DNA replication. PGC-1α and the NRF-1 thus coordinately regulate the expressions of both nuclear and mitochondrial Oxphos and genes that govern mitochondrial biogenesis, integrity and function.

Since PGC-1α is markedly diminished in DM1 skeletal muscle, the expression levels of several of the PGC-1α target genes such as Cytochrome C, Cytochrome C Oxidase (COX) IV, Tfam, and TFB2M were evaluated in DM1 skeletal muscle by Western blotting. The results showed that expression of COX IV is 50 to 60%, Tfam is 40 to 50% and TFB2M is 50 to 60% diminished in DM1. In contrast, expression of cytochrome C is not significantly different in DM1 compared to the controls. The Western blot results showed that the NRF-1 expression in DM1 is not altered in DM1, whereas NRF-2 (GABPα) expression is starkly (>70%) diminished Together, these results showed that steady state levels of several of the mtDNA-coded PGC-1α target proteins that play a key role in determining the oxidative capacity are significantly and consistently diminished in DM1 skeletal muscle compared to the age-matched controls.

Example 30

Expressions of the Mitochondrial DNA-Encoded Genes that Constitute the Oxidative Phosphorylation Chain and Govern Mitochondrial Functions are Diminished in DM1

Recent evidence suggests that the mitochondrial DNA-encoded proteins such as mtTFA (Tfam), TBF1M and TBF2M bind enhancer sequences upstream of the bidirectional mitochondrial promoters, facilitating the mtRNA polymerase function to activate transcription of mtDNA-encoded polypeptides that constitute several subunits of the mitochondrial OXPHOS chain. These genes include Cytochrome C Oxidase (COX) I, COX II, COX III, ATP synthetases etc. Since the above findings indicated that Tfam and TBF2M expressions were significantly diminished in DM1 myoblasts and skeletal muscle, the expression levels of the mitochondrial genes were evaluated in DM1 skeletal muscle by Western blotting. The results show that the expression level of COX I is 50 to 70% downregulated whereas the expression level of ATP synthetase α is 20 to 30% diminished in DM1 skeletal muscle compared to the controls. Interestingly, despite significant decreases in Tfam and TBF2M expression, the Western blot results showed that the mtDNA-encoded COX II and ATP synthetase β expressions were not significantly different in DM1 skeletal muscle compared to the controls. Collectively these findings demonstrate that several of the nuclear- as well as mtDNA-encoded proteins that are integral part of the mitochondrial oxidative phosphorylation chain and dictate the efficacy of oxidative phosphorylation and oxidative capacity of skeletal muscle are significantly diminished in DM1 skeletal muscle.

Example 31

Expression of Expanded CUG RNA is Sufficient to Downregulate the Expression of PGC-1α and its Target Genes As shown above, expanded CUG RNA complexed with skeletrophin and thus depletion of skeletrophin function resulted in chronic activation of Notch signaling in DM1. Because expanded CUG RNA was sufficient to activate Notch signaling when expressed in C2C12 myoblasts, experiments were conducted to determine whether CUG-RNA-mediated activation of Notch signaling is sufficient to downregulate PGC-1α expressions and its target genes. To achieve this goal, C2C12 myoblasts were transfected with plasmids that express 40, 700 and 1500 CUG repeats and the expression level of PGC-1α and its target genes were assessed by Western blotting. The results showed that PGC-1α levels were significantly (>70%) lower in cells expressing expanded CUG RNA sequences compared to the cells that express 40 or no repeats. Importantly, the MEF2C levels in cells expressing expanded CUG repeats remained unaltered compared to the control. These results provide evidence that CUG RNA that activates Notch signaling is sufficient to downregulate PGC-1α expressions.

Example 32

The Type I Myofiber-Specific Proteins that Determines the Oxidative Capacity of Skeletal Muscle are Markedly Downregulated in DM1 Skeletal Muscle Skeletal muscles differ in fiber composition, contractile function, mitochondrial content, oxidative capacity as well as metabolic properties. Slow-twitch (type I) myofibers contain a high concentration of mitochondria, and use oxidative metabolism as a primary energy producing mechanism; in contrast, fast-twitch myofibers (Type IIb) generate energy mainly by glycolysis. The different fiber types also express distinct arrays of contractile proteins, enzymes involved in metabolism, and regulatory proteins that act together to maintain a specific fiber phenotypes. External stimulus such as repeated mechanical overload, endurance training and electrical stimulation of motor nerves results in marked conversion of type II glycolytic muscle fibers into type I oxidative fibers. In addition to the expression of particular myofibrillar proteins, type I fibers are much higher in mitochondrial content and more dependent on oxidative metabolism than the type II fibers.

Recent evidence shows that PGC-1α in collaboration with MEF2 transcription factors regulates the expression of genes that determines muscle fiber type composition and oxidative capacity of skeletal muscle. Consistent with this hypothesis, transgenic mice expressing PGC-1α in type II fiber-enriched muscle results in dramatic fiber type switching: type II fiber-enriched muscle show higher amount of mitochondria, become more oxidative and express proteins characteristic of type I fibers, such as troponin I (slow) and myoglobin. In addition, these mice show increased resistance to electrically stimulated fatigue, characteristic of type I fiber-enriched muscles. These studies support the idea that PGC-1α plays a key role in regulating muscle fiber type compositions and oxidative capacity. DM1 skeletal muscle is characterized by progressive atrophy of type 1 oxidative myofibers and the ability to produce mechanical force is seriously blunted in DM1 skeletal muscle, and manifested with the development of progressive muscle weakness and fatigue. The mechanism by which expansion of CTG repeats results in progressive atrophy of type I myofibers is unknown. Since PGC-1α is downregulated in DM1, it would be interesting to know whether expression of type I-fiber-specific proteins are diminished in DM1 skeletal muscle. The Western blot results showed that expression of troponin I (slow) and myoglobin were markedly downregulated in DM1 skeletal muscle compared to age-matched controls. Together, these results substantiate that expression of proteins that constitute and specify type I myofibers in skeletal muscle are significantly low in DM1 skeletal muscle.

Example 33

Diminished PGC-1α Activity Stimulates FOXO3 Action and Promotes Skeletal Muscle Atrophy-Specific Genes and Progressive Muscle Loss in DM1 Skeletal Muscle

Recent evidence shows that in addition to the IGF-1-stimulated signaling, PGC-1α plays a key role in maintaining muscle mass as well as oxidative capacity of skeletal muscle. In addition to stimulating mitochondrial biogenesis and function, PGC-1α represses transcriptions mediated by transcription factor FOXO3, and thus prevents activation of the FOXO3 target genes in skeletal muscle. The FOXO3 target genes encode novel ubiquitin ligases such as atrigin-1, Murf-1 and Cathepsin L (known as atrogenes), which ubiquitinate and promote the degradation of muscle-specific proteins; thus PGC-1α prevents muscle loss by inhibiting the binding of FOXO3 to its promoter sequences, repressing the FOXO3-dependent transcription of the atrogenes. Conversely, diminished PGC-1α activity promotes the FOXO3-mediated induction of the atrophy-related atrogenes, facilitating muscle atrophy and wasting.

Since PGC-1α activity is decreased in DM1, studies were conducted to evaluate whether diminished PGC-1α is sufficient to stimulate atrogin-1 and Murf-1 in DM1. The RNA analysis showed that FOXO3 expression was not altered whereas its target genes, atrogin-1 and Murf-1, were significantly elevated in DM1 skeletal muscle that had shown signs of muscle wasting. These results support the idea that diminished PGC-1α activity is sufficient to activate transcription of the atrogenes in DM1 skeletal muscle. The current results provide evidence that chronically activated Notch diminishes PGC-1α activity and that diminished PGC-1α facilitates the activation of the ubiquitin-proteosome pathway in DM1 skeletal muscle.

Example 34

Attenuating Notch Signaling Rescues PGC-1α and its Target Gene Expressions

Based on the current experimental results, experiments were conducted to evaluate whether chronically activated Notch signaling is the principal regulatory mechanism that diminishes the oxidative capacity of DM1 skeletal muscle. To obtain more direct evidence, Notch activity was blocked in DM1 myoblasts with Jagged2 siRNA to observe whether the expression of PGC-1α and its target genes could be rescued. The Western blotting results showed that the DM1 myoblasts treated with Jagged2-siRNA showed greater than 50% reduction of Notch1 expressions. Moreover, DM1 myoblasts with attenuated Notch1 exhibited marked upregulation of PGC-1α. These results not only support the idea that Notch signaling determines PGC-1α expressions but also demonstrate that diminished PGC-1α activity in DM1 can be significantly ameliorated by attenuating Notch signaling. The Western blot results also show that the Tfam and TBF2M levels were also significantly elevated in the Jagged2-treated DM1 myoblasts.

Collectively these results corroborate the idea that the oxidative capacity of DM1 myoblasts as well as DM1 skeletal muscle can be significantly ameliorated by attenuating Notch signaling.

VII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,683,195
U.S. Pat. No. 4,683,202
U.S. Pat. No. 4,800,159
U.S. Pat. No. 4,873,191
U.S. Pat. No. 4,883,750
U.S. Pat. No. 5,175,384
U.S. Pat. No. 5,175,385
U.S. Pat. No. 5,279,721
U.S. Pat. No. 5,354,855
U.S. Pat. No. 5,399,363
U.S. Pat. No. 5,466,468
U.S. Pat. No. 5,530,179
U.S. Pat. No. 5,543,158
U.S. Pat. No. 5,565,186
U.S. Pat. No. 5,612,486
U.S. Pat. No. 5,625,125
U.S. Pat. No. 5,639,457
U.S. Pat. No. 5,641,515
U.S. Pat. No. 5,693,762
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,225
U.S. Pat. No. 5,846,233
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,486
U.S. Pat. No. 5,849,497
U.S. Pat. No. 5,849,546
U.S. Pat. No. 5,849,547
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,155
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,882,864
U.S. Pat. No. 5,900,481
U.S. Pat. No. 5,905,024
U.S. Pat. No. 5,910,407

U.S. Pat. No. 5,912,124
U.S. Pat. No. 5,912,145
U.S. Pat. No. 5,912,148
U.S. Pat. No. 5,916,776
U.S. Pat. No. 5,919,626
U.S. Pat. No. 5,919,630
U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 6,020,192
U.S. Pat. No. 6,054,297
U.S. Patent Pubn. 20030059944
U.S. Patent Pubn. 20030105051
Abbondanzo et al., *Breast Cancer Res. Treat.*, 16:182(151), 1990.
Allred et al., *Arch. Surg.*, 125(1):107-113, 1990.
Amack and Mahadevan, *Dev. Biol.*, 265(2):294-301, 2004.
Amack J. D. et al., *J Cell Biol.*, 159, 419-429, 2002.
Amack and Mahadevan, *Hum. Mol. Genet.*, 10(18):1879-1887, 2001.
Artavanis-Tsakonas et al., *Science*, 284(5415):770-776, 1999.
Ausubel et al., In: *Current Protocols in Molecular Biology*, John, Wiley & Sons, Inc, New York, 1996.
Baichwal and Sugden, In: *Gene Transfer*, Kucherlapati (Ed.), NY, Plenum Press, 117-148, 1986.
Baron M., *Seminars in Cell Dev Biol.* 14, 113-119, 2003.
Barsi J. C. et al., *Mech Dev.* 22, 1106-1117, 2005.
Bellus, *J. Macromol. Sci. Pure Appl. Chem.*, A31(1): 1355-1376, 1994.
Berzal-Herranz et al., *Genes Dev*, 6(1):129-134, 1992.
Blaschuk and ffrench-Constant, *Curr. Biol.*, 8(10):R334-337, 1998.
Brinster et al., *Proc. Natl. Acad. Sci. USA*, 82(13):4438-4442, 1985.
Brook et al., *Cell*, 68(4):799-808, 1992.
Brown et al. *Immunol. Ser.*, 53:69-82, 1990.
Brummelkamp et al., *Science*, 296(5567):550-553, 2002.
Brunner et al., *J. Med. Genet.*, 29(11):791-793, 1992.
Capaldi et al., *Biochem. Biophys. Res. Comm.*, 74(2):425-433, 1977.
Cech et al., *Cell*, 27(3 Pt 2):487-496, 1981.
Chen and Okayama, *Mol. Cell. Biol.*, 7(8):2745-2752, 1987.
Chen et al., *Development*, 130(7):1367-1379, 2003.
Chowrira et al., *Biochemistry*, 32(4):1088-1095, 1993.
Chowrira et al., *J. Biol. Chem.*, 268:19458-62, 1993.
Chowrira et al., *J. Biol. Chem.*, 269(41):25856-25864, 1994.
Coupar et al., *Gene*, 68:1-10, 1988.
Conboy I. M. et al., *Developmental Cell* 3, 397-409, 2002.
Conboy I. M. et al., *Science*, 302, 1575-1577, 2005.
Cui L, et al., *Cell*, 127, 59-69, 2006.
Day and Ranum, *Neuromuscul. Disord.*, 15(1):5-16, 2005.
Day et al., *Neurology*, 60(4):657-664, 2003.
Day et al., *Neuromuscul. Disord.*, 9(1):19-27, 1999.
De Jager et al., *Semin. Nucl. Med.*, 23(2):165-179, 1993.
Doolittle and Ben-Zeev, *Methods Mol Biol*, 109:215-237, 1999.
Elbashir et al., *Genes Dev.*, 5(2):188-200, 2001.
Fardaei et al., *Hum. Mol. Genet.*, 11(7):805-814, 2002.
Fardaei et al., *Nucleic Acids Res.*, 29(13):2766-2771, 2001.
Farkas-Bargeton et al., *J. Neurol. Sci.*, 83:145-159, 1988.
Fechheimer, et al., *Proc Natl. Acad. Sci. USA*, 84:8463-8467, 1987.
Forster and Symons, *Cell*, 49(2):211-220, 1987.
Fraley et al., *Proc. Natl. Acad. Sci. USA*, 76:3348-3352, 1979.
Frauli et al., *Med. Sci. Monit.*, 9(2):BR78-84, 2003.
Friedmann, *Science*, 244:1275-1281, 1989.
Fu et al., *Science*, 255:1256-1258, 1992.
Furling et al., *Neuromuscul Disord* 11, 728-735, 2001.
Gatchel and Zoghbi, *Nat. Rev. Genetics*, 6:743-755, 2005.
GB Appln. 2 202 328
Gerlack et al., *Nature (London)*, 328:802-805, 1987.
Go et al., *Development* 125, 2031, 1998.
Gopal, *Mol. Cell Biol.*, 5:1188-1190, 1985.
Graham and Van Der Eb, *Virology*, 52:456-467, 1973.
Groenen and Wieringa, *Bioessays*, 20(11):901-912, 1998.
Gulbis and Galand, *Hum. Pathol.*, 24(12):1271-1285, 1993.
Harland and Weintraub, *J. Cell Biol.*, 101(3):1094-1099, 1985.
Harlow and Lane, In: *Antibodies: A Laboratory Manual*, Cold Spring Harbor Laboratory, Cold Spring Harbor, N.Y., 346-348, 1988.
Harper, In: *Myotonic Dystrophy*, 3$^{rd}$ Ed., Saunders, London, 2001.
Haseloff and Gerlach, *Nature*, 334(6183):585-591, 1988.
Hashem et al., *Mutat. Res.*, 502(1-2):25-37, 2002a.
Hashem et al., *Mutat. Res.*, 502(1-2):39-46, 2002b.
Hermonat and Muzycska, *Proc. Natl. Acad. Sci. USA*, 81:6466-6470, 1984.
Ho et al., *EMBO J.*, 23(15):3103-3112, 2004.
Hogan et al., In: Manipulating the Mouse Embryo: A Laboratory Manual, 2nd ed., Cold Spring Harbor Laboratory Press, 1994.
Horwich et al. *J. Virol.*, 64:642-650, 1990.
Hsieh et al., *Mol. Cell. Biol.*, 16, 952-959, 1996.
Innis et al., *Proc. Natl. Acad. Sci. USA*, 85(24):9436-9440, 1988.
Itoh et al., *Dev. Cell.* 4, 67-82, 2003.
Jiang et al., *Hum. Mol. Genet.*, 13(24):3079-3088, 2004.
Johnson et al., In: *Biotechnology And Pharmacy*, Pezzuto et al. (Eds.), Chapman and Hall, NY, 1993.
Joyce, *Nature*, 338:217-244, 1989.
Kanadia et al., *Science*, 302(5652):1978-1980, 2003.
Kaneda et al., *Science*, 243:375-378, 1989.
Kato et al, *J. Biol. Chem.*, 266:3361-3364, 1991.
Kim and Cech, *Proc. Natl. Acad. Sci. USA*, 84(24):8788-92, 1987.
Koo et al., *J Biol Chem.* 280, 22335-22342, 2005.
La Spada et al., *Nature*, 352:77-79, 1991.
Lalioti et al., *Nature*, 386:847-851, 1997.
Le Borgne et al., *Development* 132, 1751-1762, 2005.
Lenard et al., *Neuropadiatrie.*, 8(1):42-52, 1977.
Lieber and Strauss, *Mol. Cell Biol.*, 15(1):540-551, 1995.
Lindsell et al., *Cell*, 80, 909-917, 1995.
Liguori et al., *Science*, 293:864-867, 2001.
Luo et al., *Mol. Cell Biol.*, 10:6057-6067, 1997.
MacDonald et al., *Cell*, 72:971-983, 1993.
Machuca-Tzili et al., *Muscle Nerve*, 32(1):1-18, 2005.
Mahadevan et al., *Science*, 255:1253-1255, 1992.
Mankodi and Thornton, *Curr. Opin. Neurol.*, 15(5):545-552, 2002.
Mankodi et al., *Ann. Neurol.*, 54(6):760-768, 2003.
Mankodi et al., *Mol. Cell*, 10(1):35-44, 2002.
Mankodi et al., *Science*, 289(5485):1769-1773, 2000.

Matsuura et al., *Nature Genetics*, 26:191-194, 2000.
Michel and Westhof, *J. Mol. Biol.*, 216:585-610, 1990.
Miller et al. *EMBO J* 19, 4439-4448, 2000.
Monckton and Ashizawa, In: *Myotonic dystrophy: present management and future therapy*, Harper et al. (Eds.), Myotonic. Oxford: Oxford University Press, 2004.
Nagamitsu and Ashizawa, *Adv. Neurol.*, 88:293-314, 2002.
Nakamura et al., In: *Handbook of Experimental Immunology* (4$^{th}$ Ed.), Weir et al. (Eds.), 1:27, Blackwell Scientific Publ., Oxford, 1987.
Nicolas and Rubinstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nofziger et al., *Development*, 126, 1689-1702, 1999.
Palukaitis et al., *Virology*, 99:145-151, 1979.
PCT Appln. PCT/US89/01025
PCT Appln. WO 03/012052
PCT Appln. WO 84/03564
PCT Appln. WO 90/07641
Perriman et al., *Gene*, 113:157-163, 1992.
Perrotta and Been, *Biochemistry*, 31(1):16-21, 1992.
Potter et al., *Proc. Natl. Acad. Sci. USA*, 81:7161-7165, 1984.
Prody et al., *Science*, 231:1577-1580, 1986.
Ranum and Day, *Curr. Neurol. Neurosci. Rep.*, 2(5):465-470, 2002.
Ranum and Day, *Trends Genet.*, 20(10):506-512, 2004.
Reinhold-Hurek and Shub, *Nature*, 357:173-176, 1992.
Remington's Pharmaceutical Sciences" 15th Edition, pages 1035-1038 and 1570-1580, 1990.
Ridgeway, In: *Vectors: A Survey of Molecular Cloning Vectors and Their Uses*, Rodriguez et al. (Eds.), Stoneham: Butterworth, 467-492, 1988.
Rippe, et al., *Mol. Cell Biol.*, 10:689-695, 1990.
Ronnblom et al., *Eur. J. Clin. Invest.*, 32(8):570-574, 2002.
Ronnblom et al., *J. Intern. Med.*, 245(4):91-97, 1999.
Sahgal et al., *J. Neurol. Sci.*, 59:47-55, 1983.
Sambrook et al., In: *Molecular cloning: a laboratory manual*, 2$^{nd}$ Ed., Cold Spring Harbor Laboratory Press, Cold Spring Harbor, N.Y., 1989.
Sarkar et al., *Cell*, 95(4):531-540, 1998.
Sarnat and Silbert, *Arch. Neurol.*, 33:466-474, 1976.
Sarver et al., *Science*, 247:1222-1225, 1990.
Savkur et al., *Am. J. Hum. Genet.*, 74(6):1309-1313, 2004.
Scanlon et al., *Proc. Natl. Acad. Sci. USA*, 88:10591-10595, 1991.
Shawber et al., *Development* 122, 3765-3773, 1996.
Shearman et al, *Biochemistry* 39, 8698-8704, 2000.
Sioud et al., *J. Mol. Biol.*, 223:831-835, 1992.
St-Pierre J et al., *Cell*, 127, 397-408, 2006.
Sui et al., *Proc. Natl. Acad. Sci. USA*, 99(8):5515-5520, 2002.
Symons, *Annu. Rev. Biochem.*, 61:641-671, 1992.
Symons, *Nucl. Acids Res.*, 9(23):6527-6537, 1981.
Takeuchi et al., *Am. J. Pathol.*, 166(6):1817-1826, 2005.
Takeuchi et al., *Oncogene*, 25, 7059-7069, 2006.
Tang et al., *J. Biol. Chem.*, 268(13):9522-9525, 1993.
Tapscott, *Science*, 289:1701-1702, 2000.
Temin, In: *Gene Transfer*, Kucherlapati (Ed.), NY, Plenum Press, 149-188, 1986.
Thompson et al., *Nature Medicine*, 1:277-278, 1995.
Tur-Kaspa et al., *Mol. Cell Biol.*, 6:716-718, 1986.
Wada et al., *Nucleic Acids Res.* 18:2367-2411, 1990.
Wilson-Rawls et al., *Mol Cell Biol.* 19(4):2853-62, 1999.
Wu and Wu, *Biochemistry*, 27: 887-892, 1988.
Wu and Wu, *J. Biol. Chem.*, 262:4429-4432, 1987.
Yang and Russell, *Proc. Natl. Acad. Sci. USA*, 87:4144-4148, 1990.
Yu et al., *Cell*, 88:367-374, 1997.
Yuan and Altman, *Science*, 263:1269-1273, 1994.
Yuan et al., *Proc. Natl. Acad. Sci. USA*, 89:8006-8010, 1992.

The invention claimed is:

1. A method of screening for a candidate therapeutic agent for the treatment of myotonic dystrophy type 1 (DM1) comprising:

(a) incubating a skeletrophin polypeptide with RNA molecules containing 100 to 5000 CUG trinucleotide repeats under conditions in which the skeletrophin polypeptide associates with the RNA molecules;

(b) incubating a candidate compound with the RNA molecules, skeletrophin polypeptide, or both; and (c) determining whether the candidate compound disrupts or inhibits the association between the skeletrophin polypeptide and the RNA molecules;

wherein a candidate compound that disrupts or inhibits the association is a candidate therapeutic agent for the treatment of DM1.

2. The method of claim 1, wherein the RNA molecules are dystrophia myotonica protein kinase (DMPK) transcripts.

3. The method of claim 1, wherein determining whether the candidate compound disrupts or inhibits the association between the skeletrophin polypeptide and the RNA molecules involves assaying for sequestration of the skeletrophin polypeptide, wherein a decrease in sequestration identifies the candidate compound as a candidate therapeutic agent.

4. The method of claim 3, wherein determining whether the candidate compound disrupts or inhibits the association between the skeletrophin polypeptide and the RNA molecules involves assaying Notch activity, wherein a decrease in Notch activity identifies the candidate compound as a candidate therapeutic agent.

5. The method of claim 1, wherein determining whether the candidate compound disrupts or inhibits the association between the skeletrophin polypeptide and the RNA molecules involves assaying for binding between the skeletrophin polypeptide and the RNA molecules, wherein a reduction or inhibition of binding identifies the candidate compound as a candidate therapeutic agent.

* * * * *